United States Patent
Yue et al.

(10) Patent No.: US 7,888,136 B2
(45) Date of Patent: Feb. 15, 2011

(54) UNSYMMETRICAL CYANINE DIMER COMPOUNDS AND THEIR APPLICATION

(75) Inventors: Stephen Yue, Eugene, OR (US);
Ching-Ying Cheung, San Ramon, CA (US)

(73) Assignee: Life Technologies Corporation, Carlsbad, CA (US)

(*) Notice: Subject to any disclaimer, the term of this patent is extended or adjusted under 35 U.S.C. 154(b) by 173 days.

(21) Appl. No.: 12/099,020

(22) Filed: Apr. 7, 2008

(65) Prior Publication Data

US 2008/0199875 A1    Aug. 21, 2008

Related U.S. Application Data

(63) Continuation of application No. 10/911,423, filed on Aug. 2, 2004, now abandoned.

(60) Provisional application No. 60/491,783, filed on Jul. 31, 2003.

(51) Int. Cl.
   *G01N 33/53* (2006.01)
   *B01L 3/00* (2006.01)
   *C12Q 1/68* (2006.01)
   *C07H 19/04* (2006.01)

(52) U.S. Cl. .................... 436/800; 536/26.6; 435/6; 422/61

(58) Field of Classification Search ................ 436/800; 536/26.6; 435/6; 422/61
   See application file for complete search history.

(56) References Cited

U.S. PATENT DOCUMENTS 4,711,955 A    12/1987   Ward et al.
4,883,867 A    11/1989   Lee et al.
4,957,870 A    9/1990    Lee et al.

(Continued)

FOREIGN PATENT DOCUMENTS

JP    63-132688    6/1988

(Continued)

OTHER PUBLICATIONS

Stratagene CATALOG 1988, p. 39.*

(Continued)

*Primary Examiner*—Jezia Riley
(74) *Attorney, Agent, or Firm*—Life Technologies Corporation; James K. Blodgett

(57) ABSTRACT

Embodiments of the present invention provide methods and nucleic acid reporter molecules for the detection of nucleic acid in a sample. The nucleic acid reporter molecule comprises two unsymmetrical cyanine monomer moieties, which may be the same or different, that are covalently attached by a linker comprising at least one aromatic, heteroaromatic, cyclic or heterocyclic moiety comprising 3-20 non-hydrogen atoms selected from the group consisting of O, N, S, P and C. The linker may be rigid, relatively flexible or some degree thereof. The unsymmetrical cyanine monomer moieties comprise a substituted or unsubstituted benzazolium moiety and a substituted or unsubstituted pyridinium or quinolinium moiety that is connected by a methine bridge that is monomethine, trimethine or pentamethine. The linkers form the cyanine dimer compounds by attaching to the pyridinium or quinolinium moiety of the monomer moieties. The present nucleic acid reporter molecules find utility in forming a nucleic acid-reporter molecule complex and detecting the nucleic acid. In particular, present nucleic acid reporter molecules with a rigid linker and monomer moieties with a monomethine bridge find utility in detecting RNA in the presence of DNA.

35 Claims, 10 Drawing Sheets

U.S. PATENT DOCUMENTS

| | | | |
|---|---|---|---|
| 5,047,519 | A | 9/1991 | Hobbs et al. |
| 5,314,805 | A | 5/1994 | Haugland et al. |
| 5,352,803 | A | 10/1994 | Mattingly |
| 5,362,628 | A | 11/1994 | Haugland et al. |
| 5,410,030 | A | 4/1995 | Yue et al. |
| 5,436,134 | A | 7/1995 | Haugland et al. |
| 5,534,416 | A | 7/1996 | Millard et al. |
| 5,545,535 | A | 8/1996 | Roth et al. |
| 5,573,904 | A | 11/1996 | Mattingly |
| 5,582,977 | A | 12/1996 | Yue et al. |
| 5,658,751 | A | 8/1997 | Yue et al. |
| 5,714,327 | A | 2/1998 | Houthoff et al. |
| 5,863,753 | A | 1/1999 | Haugland et al. |
| 5,929,227 | A | 7/1999 | Glazer et al. |
| 5,963,753 | A | 10/1999 | Ohtani et al. |
| 6,428,667 | B1 | 8/2002 | Glazer et al. |
| 6,579,718 | B1 | 6/2003 | Yue et al. |
| 6,664,047 | B1 | 12/2003 | Haugland et al. |

FOREIGN PATENT DOCUMENTS

| | | |
|---|---|---|
| JP | 02084383 | 3/1990 |
| JP | 2000-319260 | 11/2000 |
| WO | WO-93/06482 | 4/1993 |
| WO | WO-00/66664 | 11/2000 |
| WO | WO-2005/012579 | 2/2005 |

OTHER PUBLICATIONS

Bunkenborg et al. Bioconjugate Chem. 2000, 11, 861-867.*

U.S. Appl. No. 10/911,423, "Office Action mailed Sep. 17, 2007".

U.S. Appl. No. 10/911,423, "Office Action mailed Dec. 21, 2007".

U.S. Appl. No. 10/911,423, "Response to Sep. 17, 2007 Office Action", Filed Oct. 17, 2007.

U.S. Appl. No. 10/911,423, "Response to Rest. Req. Filed Jul. 9, 2007".

U.S. Appl. No. 10/911,423, "Restriction Req. mailed Jun. 8, 2007".

Brinkley, Michael, "A Brief Survey of Methods for Preparing Protein Conjugates with Dyes, Haptens, and Cross-Linking Reagents", *Bioconjugate Chem.*, vol. 3, No. 1 1992, 2-13.

Bunkenborg, Jakob et al., "Concerted intercalation and minor groove recognition of DNA by a homodimeric thiazole orange dye", *Bioconjugate Chemistry* vol. 11, No. 6 Nov. 2000, 861-867.

Furniss, Brian S. et al., "Resolution of Racemates", *Vogel's Textbook of Practical Organic Chemistry* Fifth Ed, Longman Group UK Ltd., Essex 1989, 809-823.

Gaugain, Bernard, "DNA Bifunctional Intercalators 2. Fluorescence Properties and DNA Binding Interaction of an Ethidium Homodimer and an Acridine Ethidium Heterodimer", *Biochemistry* vol. 17 No. 24 1978, 5078-5088.

Gaugain, Bernard et al., "DNA bifunctional intercalators. 1. Synthesis and conformational properties of an ethidium homodimer and of an acridine ethidium heterodimer", *Biochemistry* vol. 17, No. 24 1978, 5071-5078.

Haugland, Richard P., "Molecular Probes Handbook of Fluorescent Probes and Research Products", *9th Edition, 2002 (CD-Rom Format), Molecular Probes 2002.*

Heller, A., "Electrical Wiring of Redox Enzymes", *Acc. Chem. Res.* vol. 23, No. 5 1990, 128-134.

Hickman, David T. et al., "Kinetically selective binding of single stranded RNA over DNA by a pyrrolidine-amide oligonucleotide minic (POM)", *Nucleosides Nucleotides & Nucleic Acids* vol. 20, No. 4-7 2001, 1169-1172.

Markovits, J et al., "Dynamic Structure of DNA Complexes. Fluorometric Measurement of Hydrogen-Deuterium Exchange Kinetics of DNA-bound Ethidium Dimer and Acridine-Ethidium Dimer", *Biochemistry* vol. 22, No. 13 1983, 3231-3237.

Markovits, Judith et al., "Effect of B-Z transition and nucleic add structure on the conformational dynamics of bound ethidium dimer measured by hydrogen deuterium exchange kinetics", *Nucl. Acids Res.* 13 1985, 3773-3788.

Markovits, et al., "Ethidium Dimer: A New Reagent for the Fluorimetric Determination of Nucleic Acids", *Analytical Biochemistry* vol. 94 1979, 259-269.

Rye, Hays S. et al., "High-sensitivity two-color detection of double-stranded DNA with a confocal fluorescence gel scanner using ethidium homodimer and thiazole orange", *Nucleic Acids Res* vol. 19 No. 2 1990, 327-333.

Sandler, Stanley R. et al., "Organic Functional Group Preparations", vol. 3, *New York: Academic Press* 1972, 5-7.

Singh, Tara et al., "Antimalarials. Distal Hydrazine derivatives of 7-chloroquinoline", *Journal of medicinal chemistry* vol. 14, No. 6 1971, 532-5.

Staerk, Dan et al., "Bisintercalation of homodimeric thiazole orange dyes in DNA: Effect of modifying the linker", *Bioconjugate Chemistry* vol. 8, No. 6 Nov. 1997, 869-877.

Stratagene Catalog 1988, "Stragagene Cloning Systems: Tools and Technology for Life Sciences", *Gene Characterization Kits* 1988, 39.

Timtcheva, I. et al., "Homodimeric monomethine cyanine dyes as fluorescent probes of biopolymers", *Journal of Photochemistry and Photobiology B Biology* vol. 58, No. 2-3 Nov. 2000, 130-135.

Yamana, Kazushige et al., "Bis-pyrene-labeled oligonucleotide: sequence specificity of excimer and monomer fluoescence changes upon hybridization with DNA", *Bioconjug Chem* vol. 13, No. 6 2002, 1266-73.

Yamana, Kazushige et al., "Fluorescence Detection of Specific RNA Sequence Using 2'-Pyrene-Modified Oligoribonucleotides", *Angewandte Chemie International Edition in English* vol. 40 No. 6 2001, 1104-1106.

WO 2005/012579, "International Report on Patentability", Feb. 6, 2006.

WO 2005/012579, "PCT ISR", Sep. 15, 2005.

WO 2005/012579, "Written Opinion of the International Searching Authority", Jan. 31, 2006.

* cited by examiner

1: Buffer only
2: DNA Calf thymus
3: DNA Type XI, Micrococcus lysodeikticus
4: DNA Type XII, Clostridium perfringens
5: DNA Typr VIII, E. coli strain B
6: RNA, ribosomal
7: RNA Type III, Baker's yeast
8: RNA Type XX, E. coli strain W 1: Buffer only
2: DNA Calf thymus
3: DNA Type XI, Micrococcus lysodeikticus
4: DNA Type XII, Clostridium perfringens
5: DNA Typr VIII, E. coli strain B
6: RNA, ribosomal
7: RNA Type III, Baker's yeast
8: RNA Type XX, E. coli strain W

UNSYMMETRICAL CYANINE DIMER COMPOUNDS AND THEIR APPLICATION

CROSS-REFERENCE TO RELATED APPLICATIONS

This application is a continuation of U.S. patent application Ser. No. 10/911,423, filed Aug. 2, 2004, which claims priority to U.S. Patent Application No. 60/491,783, filed Jul. 31, 2003, which disclosures are herein incorporated by reference.

FIELD OF THE INVENTION

The present invention relates to unsymmetrical cyanine dimer compounds that provide a detectable fluorescent signal when complexed with nucleic acid polymers. The invention has applications in fields such as molecular biology, cell biology and fluorescence based assays.

BACKGROUND OF THE INVENTION

The detection of nucleic acid is used in a wide variety of assay formats to obtain both qualitative and quantitative information about the nucleic acid content of a sample. Fluorescent dyes that complex with DNA and in turn produce a detectable signal have increased the sensitivity and quality of information gained from such experiments. However, there still remains no fluorescent dye that is capable of detecting RNA in the presence of DNA for easy and direct detection of RNA.

Currently there exists fluorescent hybridization methods for detection of RNA in the presence of DNA wherein a dye is covalently attached to a nucleic acid hybridization probe (Micklefield, et al. Nucleosides, Nucleotides and Nucleic Acids (2001) 20(4-7), 1169, Yamana, et al. Angew. Chem. Int. Ed. (2001) 40(6), 1104 and Yamana, et al. Bioconjugate Chemistry (2002) 13, 1266). However, this method is synthetically inconvenient and requires many steps to accomplish the desired results. The current invention overcomes the restrictions of the old methods by providing a simple and efficient means of selective hybridization that requires less time and less expertise to accomplish the same or better results. Herein we report novel dimer compounds that are capable of selectively detecting RNA and which can also be used for the detection of DNA.

Dimers that are known for the detection of nucleic acid include dimers of unsymmetrical cyanine dyes, (U.S. Pat. Nos. 5,410,030; 5,582,977; 6,664,047 and WO 93106482) ethidium dimers (U.S. Pat. No. 5,314,805), acridine dimers and acridine-ethidium heterodimers (U.S. Pat. No. 6,428,667 and Rye, et al. Nucleic Acids Research (1990) 19(2), 327). The following references describe DNA intercalating fluorescent dimers and their physical characteristics: Gaugain et al., Biochemistry (1978) 17:5071-5078; Gaugain et al., Biochemistry (1978) 17:5078-5088; Markovits et al., Anal. Biochemistry (1979) 94:259-269; Markovits et al. Biochemistry (1983) 22: 3231-3237; and Markovits et al., Nucl. Acids Res. (1985) 13:3773-3788. The present dimers that are described herein are not only different in structure from other dimer compounds, but differ in spectral properties, binding affinities, intracellular properties and binding kinetics.

The present invention overcomes the limitations of the known nucleic acid reporter molecules by providing reporter molecules that are capable of detecting RNA in the presence of DNA. These novel dimer compounds are attached by a linker that contains at least one aromatic, heteroaromatic, cyclic or heterocyclic moiety. The rigidity of this moiety is one factor that allows for the ability to selectively detect RNA. In addition, the present invention also provides reporter molecules that have utility for detecting DNA.

SUMMARY OF THE INVENTION

Embodiments of the present invention provide nucleic acid reporter molecules that are dimers of unsymmetrical cyanine dyes covalently attached by a linker that contains at least one aromatic, heteroaromatic, cyclic or heterocyclic moiety. The linker comprises 3-20 non-hydrogen atoms selected from the group consisting of O, N, S, P and C. The linkers may be flexible, rigid or some degree thereof. The present nucleic acid reporter molecules find utility in detecting nucleic acid polymers wherein the dimer compounds complex with nucleic acid and provide a detectable signal. These nucleic acid polymers are single, double, triple or quadruple stranded DNA or RNA. Typically the DNA is single or double stranded and the RNA is single stranded. In one aspect of the present invention, the nucleic acid reporter molecules detect RNA in the presence of DNA by producing a fluorescent intensity signal that is greater on RNA than on DNA.

The linkers are typically represented by Formula (I) — $(Y)_r-(CH_2)_m-T_q-(CH_2)_n-E-(CH_2)_n-T_q-(CH_2)_m-(Y)_r-$ and Formula (II) $-(CH_2)_n-T_q-(CH_2)_n-E-(CH_2)_n-T_q-(CH_2)_n-$ wherein Formula (II) typically represents rigid linkers. According to formula (I) and (II), when present, Y is a linear or branched moiety comprising 1-20 non-hydrogen atoms selected from the group consisting of C, N, O, P and S; H is a heteroatom; E is an aromatic, heteroaromatic, cyclic or heterocyclic moiety comprising 3-20 non-hydrogen atoms selected from the group consisting of O, N, S, P and C; m is 0-6 and r, n and q are independently 0 or 1. Rigid linkers comprise an aromatic, heteroaromatic, cyclic or heterocyclic moiety that is either directly bonded to the cyanine monomers or contains an additional 1-6 non-hydrogen atoms that directly connect the moiety to the cyanine monomers.

In an exemplary embodiment, the present compounds are according to the formula:

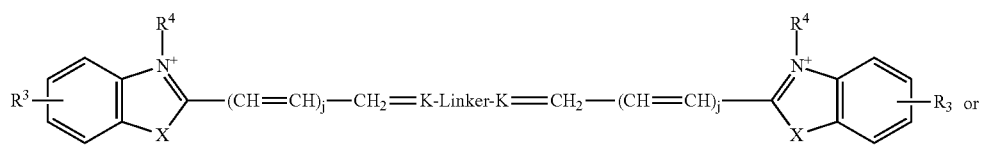

-continued

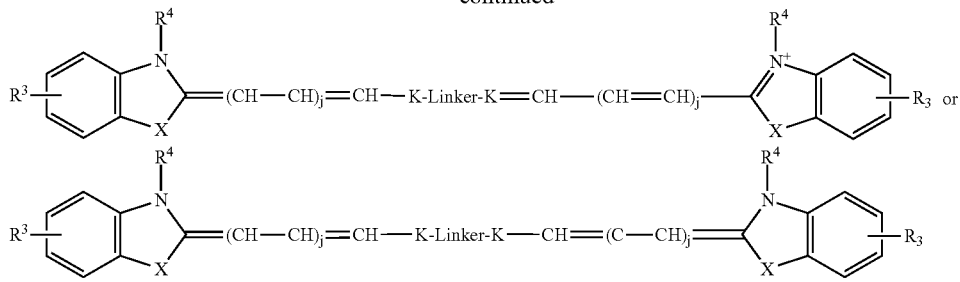

wherein each $R^3$ is independently hydrogen, unsubstituted $C_1$-$C_6$ alkyl substituted $C_1$-$C_6$ alkyl unsubstituted $C_1$-$C_6$ alkoxy, substituted $C_1$-$C_6$ alkoxy, unsubstituted fused benzene, substituted fused benzene, unsubstituted trifluoromethyl, substituted trifluoromethyl, unsubstituted halogen, substituted halogen, unsubstituted reactive group, substituted reactive group, unsubstituted carrier molecule, substituted carrier molecule, unsubstituted solid support or substituted solid support;

each $R^4$ is independently a unsubstituted $C_1$-$C_6$ alkyl substituted $C_1$-$C_6$ alkyl unsubstituted reactive group, substituted reactive group, unsubstituted carrier molecule, substituted carrier molecule, unsubstituted solid support or substituted solid support;

X is O, S, or $CR^6R^7$ wherein each $R^6$ and $R^7$ are independently a unsubstituted $C_1$-$C_6$ alkyl substituted $C_1$-$C_6$ alkyl unsubstituted reactive group, substituted reactive group, unsubstituted carrier molecule, substituted carrier molecule, unsubstituted solid support, substituted solid support or $R^6$ and $R^7$ taken together form a 5- or 6-membered saturated ring;

j is 0, 1, or 2;

linker is a series of stable covalent bonds comprising 1-30 nonhydrogen atoms selected from the group consisting of C, N, O, S and P; and, K is substituted pyridinium, unsubstituted pyridinium, substituted quinolinium, or unsubstituted quinolinium.

While unsymmetrical cyanine monomer moieties are well recognized for their ability to complex with and detect DNA, the formation of dimer compounds with particular cyanine monomer moieties and certain rigid linkers according to Formula (II) results in unexpected advantages wherein these reporter molecules are capable of detecting RNA in the presence of DNA. For these RNA reporter molecules, the cyanine monomers typically comprise a monomethine bridge and the linker is typically selected from the group consisting of:

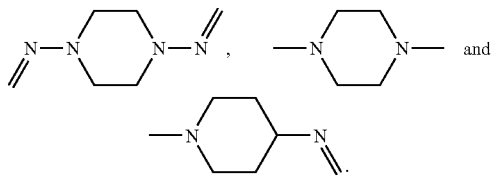

Thus, in one aspect of the invention, these RNA reporter molecules are intensely fluorescent when associated with RNA and only dimly or not at all fluorescent when associated with DNA. Therefore, the present cyanine dimer compounds comprising a linker according to Formula (I) and (II) are useful for detecting single, double, triple or quadruple stranded nucleic acid whereas a subset of these reporter molecules are particularly useful for selectively detecting RNA in the presence of DNA. Alternatively, a subset of these reporter molecules, at certain concentrations, are particularly useful for selectively detecting mitochondrial DNA.

Additional embodiments of the present invention provide kits for the detection of nucleic acid, wherein the kit comprises any compound of the present invention. In a further embodiment, the kits comprise instructions for the detection of nucleic acid, particularly instructions for the detection of intracellular RNA. In yet another further embodiment, the kits comprises at least one component that is a sample preparation reagent, a buffer agent, an organic solvent or an addition nucleic acid reporter molecule.

BRIEF DESCRIPTION OF THE FIGURES

FIG. 2 is an overlay of three graphs with the concentration of RNA 0-150 ng/mL, the concentration of DNA 150-0 ng/mL (along the same axis) and the concentration of RNA+DNA wherein the combined concentration is always 150 ng/mL where the individual concentration of RNA and DNA depends on the corresponding concentration indicated on the axis. In this way the concentrations were combined in the following format: RNA+DNA respectively, 0 ng/mL+150 ng/mL, 25 ng/mL+125 ng/mL, 50 ng/mL+100 ng/mL, 75 ng/mL+75 ng/mL, 100 ng/mL+50 ng/mL, 125 ng/mL+25 ng/mL and 150 ng/mL+0 ng/mL. These results indicate that in solution Compound 11 either does not bind DNA or binds DNA with little to no fluorescent signal intensity which is confirmed with a near zero fluorescence with DNA alone and the same fluorescence intensity signal for the RNA+DNA as for the corresponding RNA concentration. See, Example 36

DETAILED DESCRIPTION OF THE INVENTION

Definitions

Figure 1A:
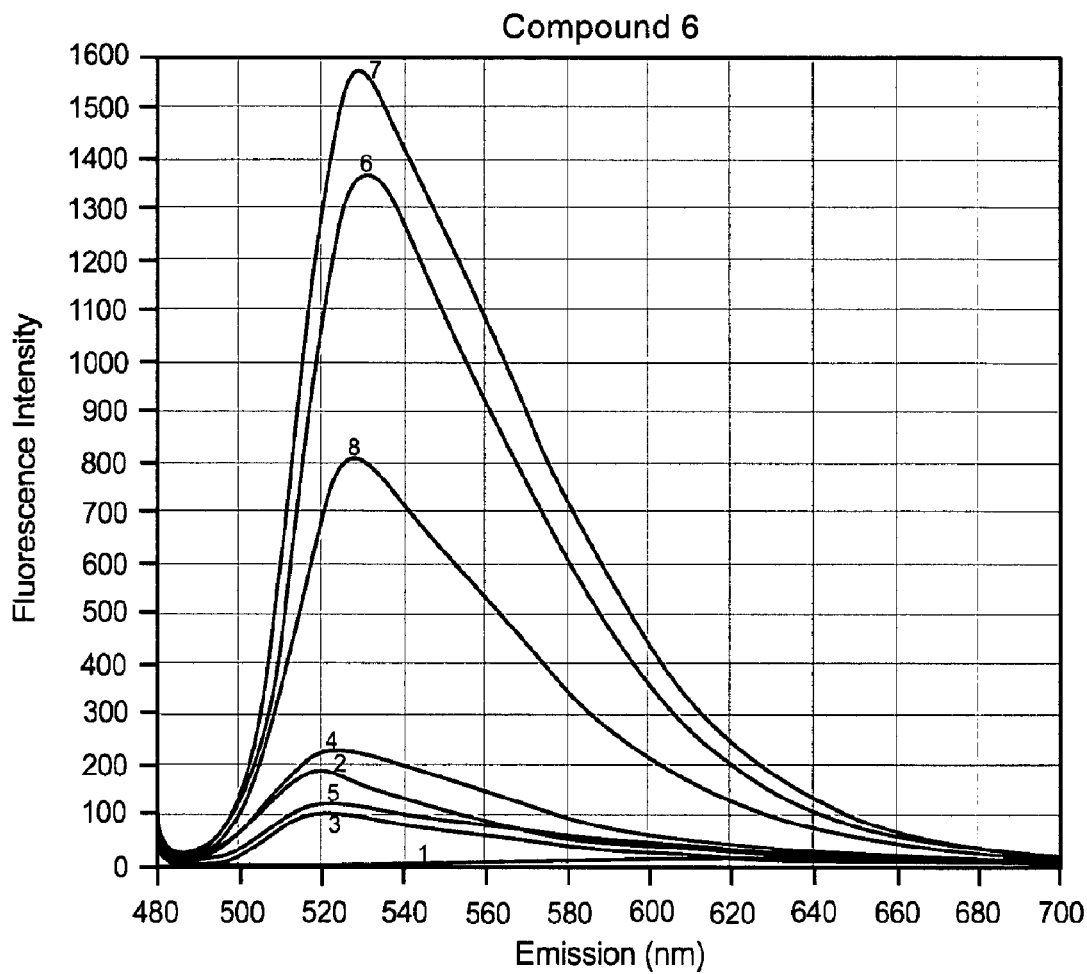
FIG. 1: Shows the intensity of the fluorescent signal from Compound 6 [1-2 µM] (FIG. 1A) and Compound 19 [1-2 µM] (FIG. 1B) bound to RNA or DNA in solution. Both compounds demonstrated a 4- to 8-fold increase in signal intensity when bound to RNA compared to DNA. See, Example 35.

Before describing the present invention in detail, it is to be understood that this invention is not limited to specific compositions or process steps, as such may vary. It must be noted that, as used in this specification and the appended claims, the singular form "a", "an" and "the" include plural referents unless the context clearly dictates otherwise. Thus, for example, reference to "a nucleic acid" includes a plurality of nucleic acids and reference to "a reporter molecule" includes a plurality of compounds and the like.

Unless defined otherwise, all technical and scientific terms used herein have the same meaning as commonly understood by one of ordinary skill in the art to which this invention is related. The following terms are defined for purposes of the invention as described herein.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

The compounds of the invention may be prepared as a single isomer (e.g., enantiomer, cis-trans, positional, diastereomer) or as a mixture of isomers. In a preferred embodiment, the compounds are prepared as substantially a single isomer. Methods of preparing substantially isomerically pure compounds are known in the art. For example, enantiomerically enriched mixtures and pure enantiomeric compounds can be prepared by using synthetic intermediates that are enantiomerically pure in combination with reactions that either leave the stereochemistry at a chiral center unchanged or result in its complete inversion. Alternatively, the final product or intermediates along the synthetic route can be resolved into a single stereoisomer. Techniques for inverting or leaving unchanged a particular stereocenter, and those for resolving mixtures of stereoisomers are well known in the art and it is well within the ability of one of skill in the art to choose an appropriate method for a particular situation. See, generally, Furniss et al. (eds.), VOGEL'S ENCYCLOPEDIA OF PRACTICAL ORGANIC CHEMISTRY $5^{TH}$ ED., Longman Scientific and Technical Ltd., Essex, 1991, pp. 809-816; and Heller, *Acc. Chem. Res.* 23: 128 (1990).

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

Where substituent groups are specified by their conventional chemical formulae, written from left to right, they equally encompass the chemically identical substituents, which would result from writing the structure from right to left, e.g., —CH$_2$O— is intended to also recite —OCH$_2$—.

The term "affinity" as used herein refers to the strength of the binding interaction of two molecules, such as a nucleic acid polymer and an intercalating agent or a positively charged moiety and a negatively charged moiety.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "alkyl" as used herein refers to a straight, branched or cyclic hydrocarbon chain fragment containing between about one and about twenty five carbon atoms (e.g. methyl, ethyl and the like). Straight, branched or cyclic hydrocarbon chains having eight or fewer carbon atoms will also be referred to herein as "lower alkyl". In addition, the term "alkyl" as used herein further includes one or more substitutions at one or more carbon atoms of the hydrocarbon chain fragment. Such substitutions include, but are not limited to: aryl; heteroaryl; halogen; alkoxy; amine (—NR'R"); carboxy and thio.

The term "amino" or "amine group" refers to the group —NR'R" (or NRR'R") where R, R' and R" are independently selected from the group consisting of hydrogen, alkyl, substituted alkyl, aryl, substituted aryl, aryl alkyl, substituted aryl alkyl, heteroaryl, and substituted heteroaryl. A substituted amine being an amine group wherein R' or R" is other than hydrogen. In a primary amino group, both R' and R" are hydrogen, whereas in a secondary amino group, either, but not both, R' or R" is hydrogen. In addition, the terms "amine" and "amino" can include protonated and quaternized versions of nitrogen, comprising the group —NRR'R" and its biologically compatible anionic counterions.

The term "aryl" as used herein refers to cyclic aromatic carbon chain having twenty or fewer carbon atoms, e.g., phenyl, naphthyl, biphenyl, and anthracenyl. One or more carbon atoms of the aryl group may also be substituted with, e.g., alkyl; aryl; heteroaryl; a halogen; nitro; cyano; hydroxyl, alkoxyl or aryloxyl; thio or mercapto, alkyl-, or arylthio;

amino, alkylamino, arylamino, dialkyl-, diaryl-, or arylalkylamino; aminocarbonyl, alkylaminocarbonyl, arylaminocarbonyl, dialkylaminocarbonyl, diarylaminocarbonyl, or arylalkylaminocarbonyl; carboxyl, or alkyl- or aryloxycarbonyl; aldehyde; aryl- or alkylcarbonyl; iminyl, or aryl- or alkyliminyl; sulfo; alkyl- or alkylcarbonyl; iminyl, or aryl- or alkyliminyl; sulfo; alkyl- or arylsulfonyl; hydroximinyl, or aryl- or alkoximinyl. In addition, two or more alkyl or heteroalkyl substituents of an aryl group may be combined to form fused aryl-alkyl or aryl-heteroalkyl ring systems (e.g., tetrahydronaphthyl). Substituents including heterocyclic groups (e.g., heteroaryloxy, and heteroaralkylthio) are defined by analogy to the above-described terms.

The term "aqueous solution" as used herein refers to a solution that is predominantly water and retains the solution characteristics of water. Where the aqueous solution contains solvents in addition to water, water is typically the predominant solvent.

The term "complex" as used herein refers to the association of two or more molecules, usually by non-covalent bonding.

The term "cyanine monomer" or "cyanine dye" as used herein refers to a fluorogenic compound that comprises 1) a substituted benzazolium moiety, 2) a polymethine bridge and 3) a substituted or unsubstituted pyridinium or quinolinium moiety. These monomer or dye moieties are capable of forming a non-covalent complex with nucleic acid and demonstrating an increased fluorescent signal after formation of the nucleic acid-dye complex.

The term "detectable response" as used herein refers to a change in or an occurrence of, a signal that is directly or indirectly detectable either by observation or by instrumentation. Typically, the detectable response is an optical response resulting in a change in the wavelength distribution patterns or intensity of absorbance or fluorescence or a change in light scatter, fluorescence lifetime, fluorescence polarization, or a combination of the above parameters.

The term "heteroaryl" as used herein refers to an aryl group as defined above in which one or more carbon atoms have been replaced by a non-carbon atom, especially nitrogen, oxygen, or sulfur. For example, but not as a limitation, such groups include furyl, tetrahydrofuryl, pyrrolyl, pyrrolidinyl, thienyl, tetrahydrothienyl, oxazolyl, isoxazolyl, triazolyl, thiazolyl, isothiazolyl, pyrazolyl, pyrazolidinyl, oxadiazolyl, thiadiazolyl, imidazolyl, imidazolinyl, pyridyl, pyridaziyl, triazinyl, piperidinyl, morpholinyl, thiomorpholinyl, pyrazinyl, piperainyl, pyrimidinyl, naphthyridinyl, benzofuranyl, benzothienyl, indolyl, indolinyl, indolizinyl, indazolyl, quinolizinyl, qunolinyl, isoquinolinyl, cinnolinyl, phthalazinyl, quinazolinyl, quinoxalinyl, pteridinyl, quinuclidinyl, carbazolyl, acridinyl, phenazinyl, phenothizinyl, phenoxazinyl, purinyl, benzimidazolyl and benzthiazolyl and their aromatic ring-fused analogs. Many fluorophores are comprised of heteroaryl groups and include, without limitations, xanthenes, oxazines, benzazolium derivatives (including cyanines and carbocyanines), borapolyazaindacenes, benzofurans, indoles and quinazolones.

The above heterocyclic groups may further include one or more substituents at one or more carbon and/or non-carbon atoms of the heteroaryl group, e.g., alkyl; aryl; heterocycle; halogen; nitro; cyano; hydroxyl, alkoxyl or aryloxyl; thio or mercapto, alkyl- or arylthio; amino, alkyl-, aryl-, dialkyl-, diaryl-, or arylalkylamino; aminocarbonyl, alkylaminocarbonyl, arylaminocarbonyl, dialkylaminocarbonyl, diarylaminocarbonyl or arylalkylaminocarbonyl; carboxyl, or alkyl- or aryloxycarbonyl; aldehyde; aryl- or alkylcarbonyl; iminyl, or aryl- or alkyliminyl; sulfo; alkyl- or arylsulfonyl; hydroximinyl, or aryl- or alkoximinyl. In addition, two or more alkyl substituents may be combined to form fused heterocycle-alkyl ring systems. Substituents including heterocyclic groups (e.g., heteroaryloxy, and heteroaralkylthio) are defined by analogy to the above-described terms.

The term "heterocycloalkyl" as used herein refers to a heterocycle group that is joined to a parent structure by one or more alkyl groups as described above, e.g., 2-piperidylmethyl, and the like. The term "heterocycloalkyl" refers to a heteroaryl group that is joined to a parent structure by one or more alkyl groups as described above, e.g., 2-thienylmethyl, and the like. The term "kit" as used refers to a packaged set of related components, typically one or more compounds or compositions.

The term "nucleic acid polymer" as used herein refers to natural or synthetic polymers of DNA or RNA that are single, double, triple or quadruple stranded. Polymers are two or more bases in length.

The term "nucleic acid reporter molecule" as used herein refers to the present dimer compounds represented by the formula A-L-B wherein L is a linker comprising at least one aromatic, heteroaromatic, cyclic or heterocyclic moiety and A and B are nucleic acid intercalating monomer compounds, which may be the same or different.

The term "reactive group" as used herein refers to a group that is capable of reacting with another chemical group to form a covalent bond, i.e. is covalently reactive under suitable reaction conditions, and generally represents a point of attachment for another substance.

The reactive group is a moiety, such as carboxylic acid or succinimidyl ester, on the compounds of the present invention that is capable of chemically reacting with a functional group on a different compound to form a covalent linkage. Reactive groups generally include nucleophiles, electrophiles and photoactivatable groups.

Exemplary reactive groups include, but are not limited to, olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds. Reactive functional groups also include those used to prepare bioconjugates, e.g., N-hydroxysuccinimide esters, maleimides and the like. Methods to prepare each of these functional groups are well known in the art and their application to or modification for a particular purpose is within the ability of one of skill in the art (see, for example, Sandler and Karo, eds. ORGANIC FUNCTIONAL GROUP PREPARATIONS, Academic Press, San Diego, 1989).

The term "reporter molecule" as used herein refers to any luminescent molecule that is capable of associating with a nucleic acid polymer and producing a detectable signal. Typically, reporter molecules include unsymmetrical cyanine dyes, dimmers of cyanine dyes, ethidium bromide, DAPI, Hoechst, acridine and styryl dyes that are capable of producing a detectable signal upon appropriate wavelength excitation.

The term "sample" as used herein refers to any material that may contain a target ligand. Typically, the sample is a live cell, a biological fluid that comprises endogenous host cell proteins, nucleic acid polymers, nucleotides, oligonucleotides, peptides and buffer solutions. The sample may be in an aqueous solution, a viable cell culture or immobilized on a solid or semi solid surface such as a polyacrylamide gel, membrane blot or on a microarray.

Compounds

In general, for ease of understanding the present invention, the nucleic acid reporter molecules and corresponding substituents will first be described in detail, followed by the many and varied methods in which the compounds find uses, which is followed by exemplified methods of use and synthesis of novel compounds that are particularly advantageous for use with the methods of the present invention.

In one embodiment the present invention provides novel linkers that comprise at least one aromatic, heteroaromatic, cyclic or heterocyclic moiety that covalently bonds two nucleic acid complexing monomer compounds into a hetero- or homodimer that form nucleic acid reporter molecules. Without wishing to be bound by a theory, it appears that typically the complexing monomer compounds bind in the minor groove of nucleic acid, but compounds that bind in the major groove are also included. The aromatic, heteroaromatic, cyclic or heterocyclic moiety typically comprises 3-20 non-hydrogen atoms selected from the group consisting of N, O, P, C and S. The nucleic acid complexing compounds include, without limitation, any compound known to one skilled in the art and novel compounds yet to be discovered, such as cyanine dyes, styryl dyes, ethidium bromide, DAPI, Hoechst and acridine. There is no intended limitation on the nucleic acid complexing compound.

In this instance present nucleic acid reporter molecules are represented by the general formula A-L-B wherein A and B, which may be the same or different, are nucleic acid complexing compound monomers and L is a linker that comprises at least one aromatic, heteroaromatic, cyclic or heterocyclic moiety. These compounds may be cell permeable or non-cell permeable depending on the lipophilic properties of the individual compounds.

Typically, the nucleic acid complexing compound monomers are unsymmetrical cyanine dyes including, but are not limited to, dyes sold under the trade name SYBR® dyes (Molecular Probes, Inc.), thiazole orange, their derivatives and any monomer compound disclosed in U.S. Pat. Nos. 4,957,870; 4,883,867; 5,436,134; 5,658,751, 5,534,416 and 5,863,753.

Thus, in one aspect the compounds of the present invention include, but are not limited to, a nucleic acid reporter molecule comprising two unsymmetrical cyanine monomer moieties which may be the same or different, covalently attached by a linker comprising at least one aromatic, heteroaromatic, cyclic or heterocyclic moiety comprising 3-20 non-hydrogen atoms selected from the group consisting of O, N, S, P and C.

In another exemplary embodiment, the present dimer compounds are cell permeable due to the lipophilicity of the compounds. These compounds are represented by the general formula A-L*-B wherein A and B, which may be the same or different, are nucleic acid compound monomers that are cell permeable unsymmetrical cyanine dyes, and the linker L* is a series of stable covalent bonds the linker typically incorporates 1-30 nonhydrogen atoms selected from the group consisting of C, N, O, S and P. This class of compounds represent, for the first time, cyanine dimers that are cell permeable. While the monomers are lipophilic it is not obvious, due to the size of the compound, that these dimer compounds would be cell permeable. Thus, these compounds represent an improvement over known dimer compounds, which are not cell permeable and thus unable to associate with and detect nucleic acid in a live cell.

1. Unsymmetrical Cyanine Monomer Moieties

Typically, A and B are unsymmetrical cyanine monomer moieties. The cyanine monomer moieties are further comprised of three moieties; F-M-K, wherein the F moiety is a substituted or unsubstituted benzazolium ring system that may or may not contain a quarternized nitrogen atom, the M moiety is a mono or polymethine bridge and the K moiety is substituted or unsubstituted pyridinium or quinolinium moiety.

The unsymmetrical cyanine moieties are typically represented by the general formula:

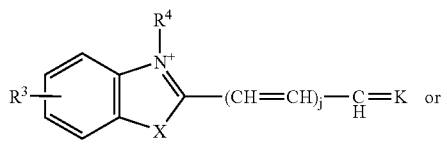

Formula (III)(z)

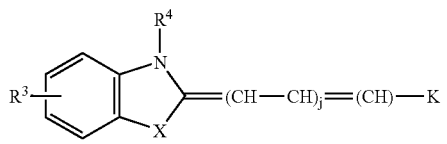

Formula (III)(y)

wherein $R^3$ is selected from the group consisting of hydrogen, $C_1$-$C_6$ alkyl $C_1$-$C_6$ alkoxy, fused benzene, trifluoromethyl, halogen, reactive group, carrier molecule and solid support, each of which may be optionally further substituted. $R^3$ is typically hydrogen, but substituents other than hydrogen may used to alter the absorption and emission spectra of the compound. In addition, the benzazolium moiety may contain more that one $R^3$, (1-4) which may be the same or different. But, typically there is not more than one $R^3$ that is not hydrogen.

$R^4$ is a $C_1$-$C_6$ alkyl, a reactive group, a carrier molecule or a solid support and X is O, S, or $CR^6R^7$ wherein $R^6$ and $R^7$ are independently a $C_1$-$C_6$ alkyl group, a reactive group, carrier molecule, solid support or taken together form a 5- or 6-membered saturated ring, each of which may be further substituted. Typically, $R^4$ is methyl or ethyl preferably $R^4$ is methyl.

The methine bridge consists of 1, 3 or 5 methine groups (—CH=), wherein J is 0, 1 or 2; that covalently attaches the benzazolium moiety to the K moiety of the cyanine monomer compound. The length of the methine bridge has a considerable effect on the absorption and emission spectra of the unsymmetrical cyanine monomer moieties. In addition, we have found that monomethine cyanine monomer moieties when comprising a present nucleic acid reporter molecule that is attached by a rigid linker according to Formula (II) fluoresce more intensely on RNA than DNA when in the presence of DNA. In this instance, when complexed with nucleic acid (RNA or DNA) the ratio of fluorescence enhancement (fluorescent intensity signal) is greater than one for RNA compared to DNA. Thus, monomethine unsymmetrical cyanine monomer moieties with rigid linkers are preferred for RNA reporter molecules.

In one aspect of the invention, $R^3$ is hydrogen, $R^4$ is methyl, X is S and t is 0. In another aspect of the invention $R^3$ is hydrogen, $R^4$ is methyl, X is O and t is 0. In yet another aspect, t is 1.

The K moiety is a substituted or unsubstituted pyridinium or quinolinium moiety. The substitutents of the pyridinium or quinolinium moiety include substituents well known in the art, including hydrogen, alkyl group, halogen, alkoxy, a saturated or unsaturated, substituted or unsubstituted cyclic substituent including aryl, benzene, phenyl group, reactive group, carrier molecule or solid support. Typically, the pyridinium or quinolinium moiety is substituted by hydrogen or alkoxy at a ring carbon atom. Preferably the alkoxy group is methoxy.

A $C_1$-$C_6$ alkyl group or a saturated or unsaturated, substituted or unsubstituted cyclic substituent typically substitutes the nitrogen atom of the pyridinium or quinolinium moiety. The alkyl group and cyclic substituent may be further substituted by hydrogen, alkyl, amino, alkylamino, alkoxy or carboxyalkyl. Typically, a methyl group or an aromatic group such as phenyl substitutes the nitrogen atom. Without wishing to be bound by a theory it appears that the cyclic substituent increases the membrane permeability of the cyanine monomer moieties and is, thus, typically included for present nucleic acid reporter molecules that are to be used to detect nucleic acid in live or fixed cells.

The pyridinium or quinolinium moiety is also substituted by the present linker wherein the linker attaches two cyanine monomer moieties at their respective K moieties. The dimer compounds may be homo- or heterodimer compounds wherein the unsymmetrical cyanine monomer moieties may be the same or different.

In one aspect of the invention, a preferred unsymmetrical cyanine monomer is represented by the general formula:

Formula (III)(a)

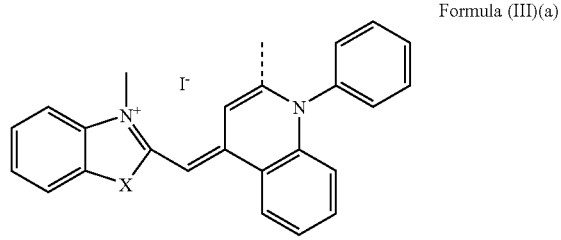

The dashed line represents the point of attachment for the linker on the quinolinium moiety and X is S or O. For simplicity the benzo substitutents are represented by hydrogen but the benzo rings may be substituted by any moiety known to one skilled in the art, including, but not limited to $C_1$-$C_6$ alkyl $C_1$-$C_6$ alkoxy, fused benzene, trifluoromethyl, halogen, reactive group, carrier molecule or solid support. These substituents may be further substituted, as described above.

In another aspect of the invention, a cyanine monomer is represented by the general formula:

Formula (III)(b)

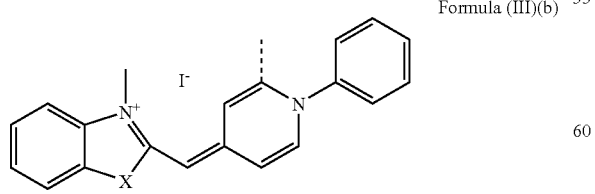

wherein the pyridinium moiety is substituted by a phenyl group on the nitrogen atom. The dashed line represents the point of attachment for the linker and X is S or O.

Alternatively, the following compound is also preferred wherein t is represented by 1, resulting in a trimethine cyanine monomer moiety represented by the general formula:

Formula (III)(c)

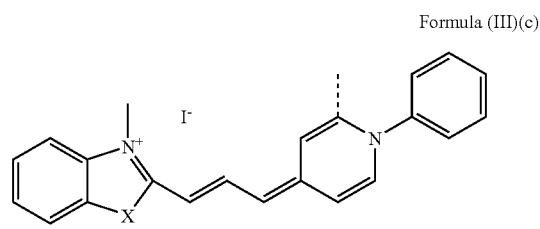

In another aspect of the invention, the unsymmetrical cyanine monomer is represented by the general formula:

Formula (III)(d)

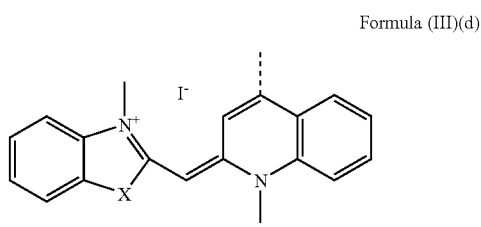

wherein the nitrogen atom of the quinolinium moiety is substituted by an alkyl group and the dashed line represents the point of attachment for the linker and X is O or S.

In yet another aspect of the invention, the unsymmetrical cyanine monomer is represented by the general formula:

Formula (III)(e)

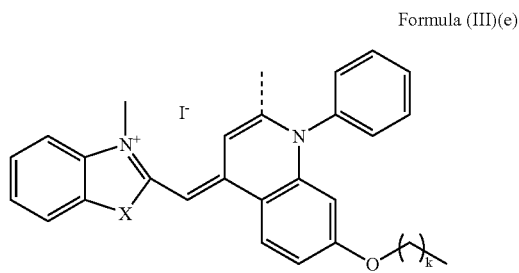

Wherein the quinolinium moiety is substituted by a $C_1$-$C_6$ alkoxy wherein k is 0-5. Typically, k is 0 designating a methoxy group. The dashed line represents the point of attachment for the linker and X is O or S.

In an additional example of the invention, a julolidine derivative is employed and is represented by the general formula:

Formula (III)(f)

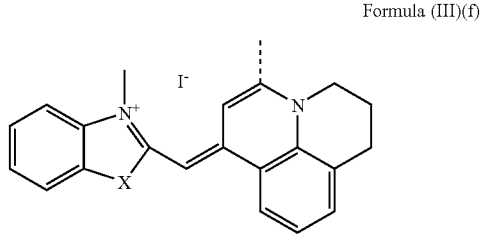

Wherein the dashed line represents the point of attachment for the linker and X is O or S.

In another example of the invention, the methylated quinolium is attached ortho to the cyanine monomer.

Formula (III)(g)

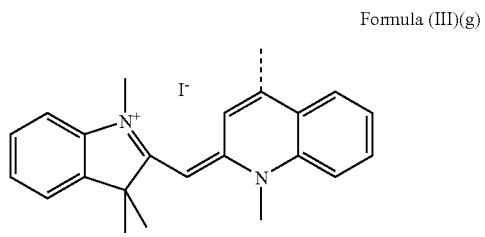

Wherein the dashed line represents the point of attachment for the linker and X is $C(CH_3)_2$.

In an exemplified embodiment of the present invention, a phenyl substituted quinolium attached para to an indolenine monomer is represent by the general formula:

Formula (III)(h)

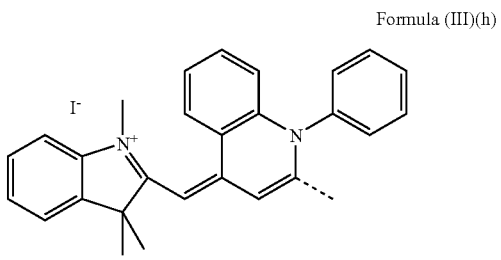

Wherein the dashed line represents the point of attachment for the linker.

2. Linkers

The present nucleic acid reporter molecules comprise a linker covalently attaching two monomer moieties wherein the linker (L) comprises at least one aromatic, heteroaromatic, cyclic or heterocyclic moiety. The ring moiety contains 3-20 non-hydrogen atoms selected from the group consisting of C, N, O, S, and P. This moiety in its self may confer rigidity to the linker, or when part of longer linker is typically not rigid. These linkers have novel properties in forming unsymmetrical cyanine dimer compounds and provide nucleic acid reporter molecules with unexpected advantages for detecting RNA in the presence of DNA.

Typically the linker is represented by Formula (I) —$(Y)_r$— $(CH_2)_m$-$T_q$-$(CH_2)_n$-E-$(CH_2)_n$-$T_q$-$(CH_2)_m$—$(Y)_r$—. When present, Y is a linear, branched, cyclic or aromatic moiety comprising 1-20 non-hydrogen atoms selected from the group consisting of C, N, O, P and S. The Y moiety may be any combination of stable chemical bonds, optionally including, single, double, triple or aromatic carbon-carbon bonds, as well as carbon-nitrogen bonds, nitrogen-nitrogen bonds, carbon-oxygen bonds, sulfur-sulfur bonds, carbon-sulfur bonds, phosphorus-oxygen bonds, phosphorus-nitrogen bonds, and nitrogen-platinum bonds. Typically the Y moiety incorporates less than 15 nonhydrogen atoms and are composed of any combination of ether, thioether, thiourea, amine, ester, carboxamide, sulfonamide, hydrazide and aromatic or heteroaromatic bonds. Typically the Y moiety is a combination of single carbon-carbon bonds and carboxamide, sulfonamide or thioether bonds. The bonds of the Y moiety typically result in the following moieties that can be found in the Y moiety: ether, thioether, carboxamide, thiourea, sulfonamide, urea, urethane, hydrazine, alkyl, aryl, heteroaryl, alkoxy, cycloalkyl and amine moieties. The Y moiety may be absent or present wherein r is 0 or 1. In addition, the Y moiety may be substituted by a reactive group, carrier molecule or solid support.

T is a heteroatom selected from the group consisting of P, O, S, $NR^2$ wherein $R^2$ is hydrogen, amine, substituted amine, a $C_1$-$C_6$ alkyl group, reactive group, carrier molecule, solid support or is absent. Typically, the heteroatom is S, $NR^2$ or is absent wherein q is 0, when present q is 1. Preferably the heteroatom is $NR^2$. The alkyl group —$(CH_2)$— directly adjacent to the E moiety may be independently a methyl group or absent wherein n is 0 or 1. The alkyl group between the Y moiety and the T heteroatom may independently be absent or a $C_1$-$C_6$ alkyl.

The E moiety is an aromatic, heteroaromatic, cyclic or heterocyclic moiety comprising 3-20 non-hydrogen atoms selected from the group consisting of O, N, S, P and C. The E moiety can be fully saturated or unsaturated and can contain no heteroatoms or one or more heteroatoms. Typically, the heteroatoms, when present, are oxygen or nitrogen. The E moiety typically includes, without limitation, benzene, pyrimidine, piperazine, piperidine, cyclohexane, cyclopentane, dioxane, tetrahydropyran, tetrahydrofuran, pyrole, thiophene, furna, oxazole, pyridine, thiazole, cyclen and pyrrolidine.

Thus, in one aspect of the invention, the E moiety is selected from the group consisting of

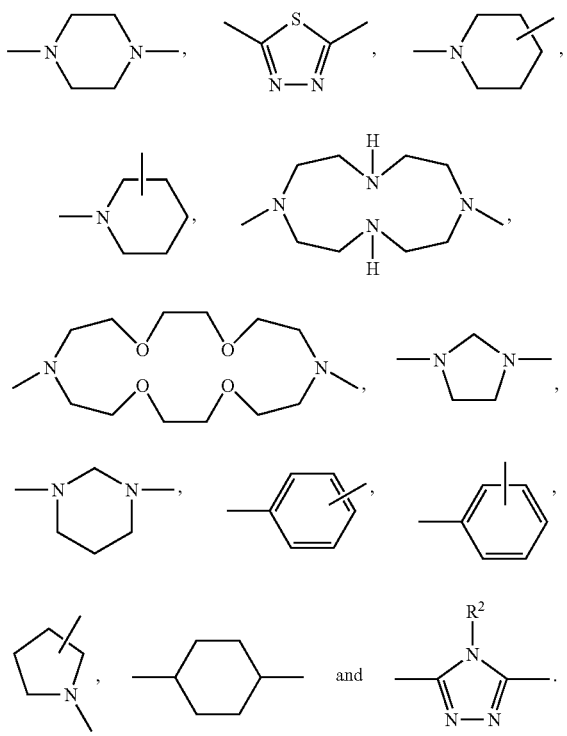

Wherein $R^2$ is hydrogen, amine, substituted amine, substituted or unsubstituted $C_1$-$C_6$ alkyl unsubstituted reactive group, substituted reactive group, unsubstituted carrier molecule, substituted carrier molecule, unsubstituted solid support or substituted solid support.

In one aspect of the invention, the linkers are rigid and are represented by Formula (II) —$(CH_2)_n$-$T_q$-$(CH_2)_n$-E-$(CH_2)_n$-

$T_q$-$(CH_2)_n$— wherein T and E are as described above. n and q are independently 0 or 1. These linkers are not permitted to have a long alkyl chain or the Y moiety.

Preferred rigid linkers are according to the following general formulas wherein the E moiety is designated:

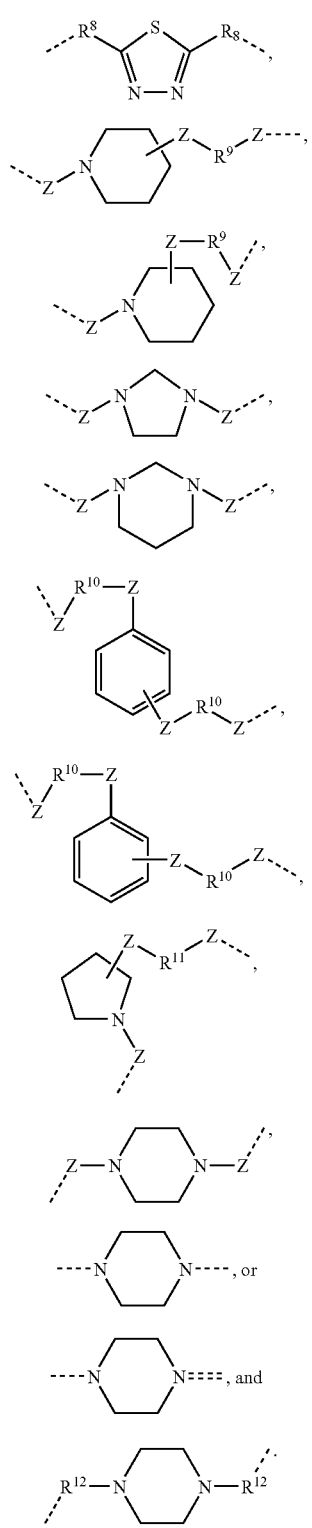

Each $R^8$, $R^9$, $R^{10}$, $R^{11}$ and $R^{12}$ are independently a substituted or unsubstituted heteroatom and each Z is independently methylene or is absent that is represented as —$(CH_2)_g$ wherein g is 0 or 1. The dashed line is attached directly to the respective K moiety of the unsymmetrical cyanine monomer. Typically, the heteroatom is —$NR^2$, —N= or S wherein $R^2$ is hydrogen, amine, substituted amine, substituted or unsubstituted $C_1$-$C_6$ alkyl amine, substituted amine unsubstituted reactive group, substituted reactive group, unsubstituted carrier molecule, substituted carrier molecule, unsubstituted solid support or substituted solid support.

In a further embodiment, formula (II)(i) is represented by the linkers

Thus, selected linkers include:

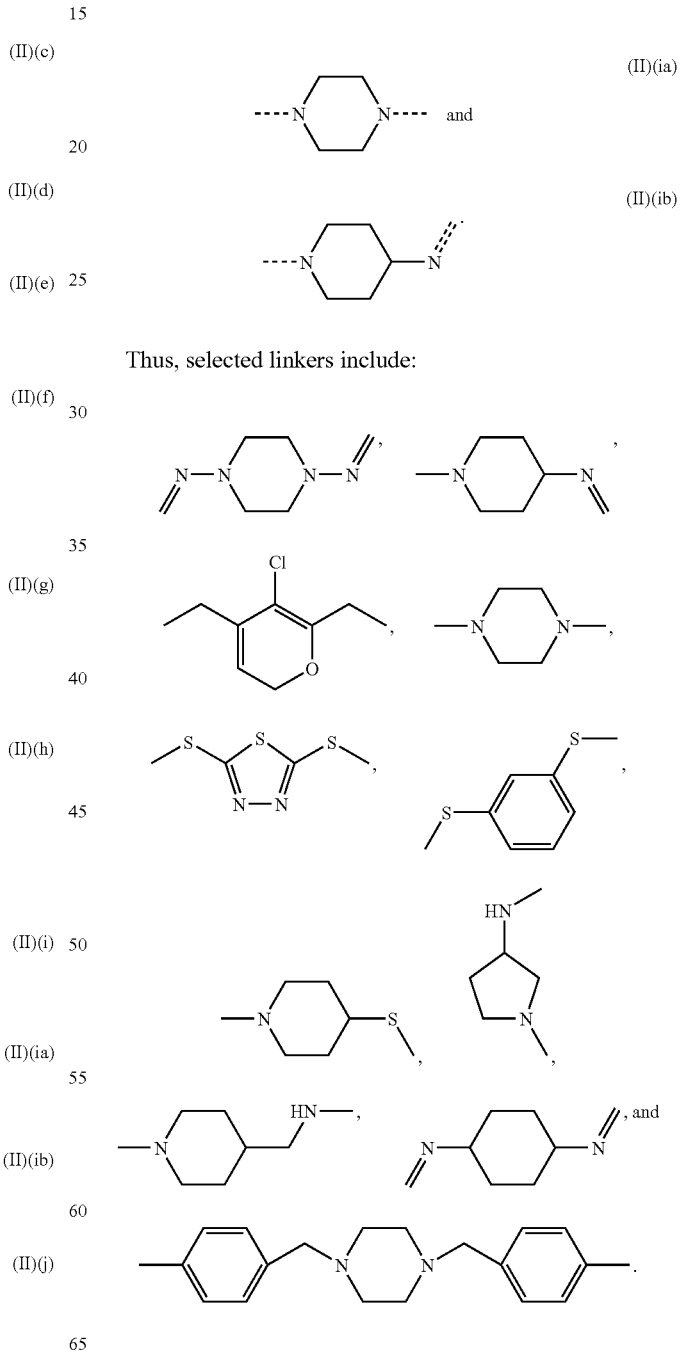

As discussed above, in one aspect of the invention, the present nucleic acid reporter molecules are used to detect RNA in the presence of DNA. In this aspect the linkers are typically selected from the group consisting of

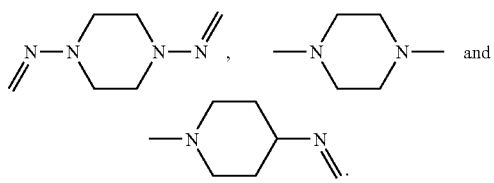

When these linkers attach two monomethine unsymmetrical cyanine monomer moieties in a present nucleic acid reporter molecule the molecule forms a nucleic acid-reporter molecule complex that is capable of fluorescing more intensely on RNA than DNA.

Alternatively, the present compounds comprise the linker (L*), wherein the linker is a series of stable covalent bonds. The linker typically incorporates 1-30 nonhydrogen atoms selected from the group consisting of C, N, O, S and P. The linker may be any combination of stable chemical bonds, optionally including, single, double, triple or aromatic carbon-carbon bonds, as well as carbon-nitrogen bonds, nitrogen-nitrogen bonds, carbon-oxygen bonds, sulfur-sulfur bonds, carbon-sulfur bonds, phosphorus-oxygen bonds, phosphorus-nitrogen bonds, and nitrogen-platinum bonds. Typically the linker incorporates less than 15 nonhydrogen atoms and are composed of any combination of ether, thioether, thiourea, amine, ester, carboxamide, sulfonamide, hydrazide bonds and aromatic or heteroaromatic bonds. Typically the linker is a combination of single carbon-carbon bonds and carboxamide, sulfonamide or thioether bonds. The bonds of the linker typically result in the following moieties that can be found in the linker: ether, thioether, carboxamide, thiourea, sulfonamide, urea, urethane, hydrazine, alkyl, aryl, heteroaryl, alkoxy, cycloalkyl and amine moieties. Examples of a linker include substituted or unsubstituted polymethylene, arylene, alkylarylene, arylenealkyl, and arylthio.

In one embodiment, the linker contains 1-6 carbon atoms; in another, the linker comprises a thioether linkage. Exemplary linking members include a moiety that includes —C(O)NH—, —C(O)O—, —NH—, —S—, —O—, and the like. In another embodiment, the linker is or incorporates the formula —(CH$_2$)$_d$(CONH(CH$_2$)$_e$)$_z$— or where d is an integer from 0-5, e is an integer from 1-5 and z is 0 or 1. In a further embodiment, the linker is or incorporates the formula —O—(CH$_2$)—. In yet another embodiment, the linker is or incorporates a phenylene or a 2-carboxy-substituted phenylene.

Reactive Groups, Carrier Molecules and Solid Supports

The present compounds, in certain embodiments, are chemically reactive wherein the compounds comprise a reactive group. In a further embodiment, the compounds comprise a carrier molecule or solid support. These substituents, reactive groups, carrier molecules, and solid supports, comprise a linker that is used to covalently attach the substituents to any of the moieties of the present compounds having the formula A-L-B or A-L*-B. The solid support, carrier molecule or reactive group may be directly attached (where linker is a single bond) to the moieties or attached through a series of stable bonds, as disclosed above.

Any combination of linkers may be used to attach the carrier molecule, solid support or reactive group and the present compounds together. The linker may also be substituted to alter the physical properties of the reporter moiety or chelating moiety, such as spectral properties of the dye.

An important feature of the linker is to provide an adequate space between the carrier molecule, reactive group or solid support and the nucleic acid reporter molecule so as to prevent steric hinderance. Therefore, the linker of the present compound is important for (1) attaching the carrier molecule, reactive group or solid support to the compound, (2) providing an adequate space between the carrier molecule, reactive group or solid support and the compound so as not to sterically hinder the action of the compound and (3) for altering the physical properties of the present compounds.

In another exemplary embodiment of the invention, the present compounds are chemically reactive, and are substituted by at least one reactive group. The reactive group functions as the site of attachment for another moiety, such as a carrier molecule or a solid support, wherein the reactive group chemically reacts with an appropriate reactive or functional group on the carrier molecule or solid support. Thus, in another aspect of the present invention the compounds comprise the chelating moiety, linker, reporter moiety, a reactive group moiety and optionally a carrier molecule and/or a solid support.

In an exemplary embodiment, the compounds of the invention further comprise a reactive group which is a member selected from an acrylamide, an activated ester of a carboxylic acid, a carboxylic ester, an acyl azide, an acyl nitrile, an aldehyde, an alkyl halide, an anhydride, an aniline, an amine, an aryl halide, an azide, an aziridine, a boronate, a diazoalkane, a haloacetamide, a haloalkyl, a halotriazine, a hydrazine, an imido ester, an isocyanate, an isothiocyanate, a maleimide, a phosphoramidite, a photoactivatable group, a reactive platinum complex, a silyl halide, a sulfonyl halide, and a thiol. In a particular embodiment the reactive group is selected from the group consisting of carboxylic acid, succinimidyl ester of a carboxylic acid, hydrazide, amine and a maleimide. In exemplary embodiment, at least one member selected from A, L or B comprises a reactive group. Preferably, at least one of A or B comprises a reactive group, wherein at least one of R$^3$, R$^4$, R$^6$ or R$^7$ is a reactive group or is attached to a reactive group. In another aspect, L comprises a reactive group; typically the E moiety is attached to a reactive group. Alternatively, if the present compound comprises a carrier molecule or solid support a reactive group may be covalently attached independently to those substituents, allowing for further conjugation to a reporter molecule, carrier molecule or solid support.

In one aspect, the compound comprises at least one reactive group that selectively reacts with an amine group. This amine-reactive group is selected from the group consisting of succinimidyl ester, sulfonyl halide, tetrafluorophenyl ester and iosothiocyanates. Thus, in one aspect, the present compounds form a covalent bond with an amine-containing molecule in a sample. In another aspect, the compound comprises at least one reactive group that selectively reacts with a thiol group. This thiol-reactive group is selected from the group consisting of maleimide, haloalkyl and haloacetamide (including any reactive groups disclosed in U.S. Pat. Nos. 5,362,628; 5,352,803 and 5,573,904).

The pro-reactive groups are synthesized during the formation of the monomer moieties and carrier molecule and solid support containing compounds to provide chemically reactive nucleic acid reporter compounds. In this way, compounds incorporating a reactive group can be covalently attached to a wide variety of carrier molecules or solid supports that contain or are modified to contain functional groups with suitable reactivity, resulting in chemical attachment of the components. In an exemplary embodiment, the reactive group of the compounds of the invention and the functional group of the carrier molecule or solid support comprise electrophiles and nucleophiles that can generate a covalent linkage between them. Alternatively, the reactive group comprises a photoactivatable group, which becomes chemically reactive only after illumination with light of an appropriate wavelength. Typically, the conjugation reaction between the reactive group and the carrier molecule or solid support results in one or more atoms of the reactive group being incorporated into a new linkage attaching the present compound of the invention to the carrier molecule or solid support. Selected examples of functional groups and linkages are shown in Table 1, where the reaction of an electrophilic group and a nucleophilic group yields a covalent linkage.

TABLE 1

Examples of some routes to useful covalent linkages

| Electrophilic Group | Nucleophilic Group | Resulting Covalent Linkage |
|---|---|---|
| activated esters* | amines/anilines | carboxamides |
| acrylamides | thiols | thioethers |
| acyl azides** | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| alkyl sulfonates | thiols | thioethers |
| alkyl sulfonates | carboxylic acids | esters |
| alkyl sulfonates | alcohols/phenols | ethers |
| anhydrides | alcohols/phenols | esters |
| anhydrides | amines/anilines | carboxamides |
| aryl halides | thiols | thiophenols |
| aryl halides | amines | aryl amines |
| aziridines | thiols | thioethers |
| boronates | glycols | boronate esters |
| carbodiimides | carboxylic acids | N-acylureas or anhydrides |
| diazoalkanes | carboxylic acids | esters |
| epoxides | thiols | thioethers |
| haloacetamides | thiols | thioethers |
| haloplatinate | amino | platinum complex |
| haloplatinate | heterocycle | platinum complex |
| haloplatinate | thiol | platinum complex |
| halotriazines | amines/anilines | aminotriazines |
| halotriazines | alcohols/phenols | triazinyl ethers |
| halotriazines | thiols | triazinyl thioethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonate esters | thiols | thioethers |
| sulfonate esters | carboxylic acids | esters |
| sulfonate esters | alcohols | ethers |
| sulfonyl halides | amines/anilines | sulfonamides |
| sulfonyl halides | phenols/alcohols | sulfonate esters |

*Activated esters, as understood in the art, generally have the formula —COΩ, where Ω is a good leaving group (e.g., succinimidyloxy (—OC$_4$H$_4$O$_2$) sulfosuccinimidyloxy (—OC$_4$H$_3$O$_2$—SO$_3$H), -1-oxybenzotriazolyl(—OC$_6$H$_4$N$_3$); or an aryloxy group or aryloxy substituted one or more times by electron withdrawing substituents such as nitro, fluoro, chloro, cyano, or trifluoromethyl, or combinations thereof, used to form activated aryl esters; or a carboxylic acid activated by a carbodiimide to form an anhydride or mixed anhydride —OCOR$^a$ or —OCNR$^a$NHR$^b$, where R$^a$ and R$^b$, which may be the same or different, are C$_1$-C$_6$ alkyl, C$_1$-C$_6$ perfluoroalkyl, or C$_1$-C$_6$ alkoxy; or cyclohexyl, 3-dimethylaminopropyl, or N-morpholinoethyl).
**Acyl azides can also rearrange to isocyanates Choice of the reactive group used to attach the compound of the invention to the substance to be conjugated typically depends on the reactive or functional group on the substance to be conjugated and the type or length of covalent linkage desired. The types of functional groups typically present on the organic or inorganic substances (biomolecule or non-biomolecule) include, but are not limited to, amines, amides, thiols, alcohols, phenols, aldehydes, ketones, phosphates, imidazoles, hydrazines, hydroxylamines, disubstituted amines, halides, epoxides, silyl halides, carboxylate esters, sulfonate esters, purines, pyrimidines, carboxylic acids, olefinic bonds, or a combination of these groups. A single type of reactive site may be available on the substance (typical for polysaccharides or silica), or a variety of sites may occur (e.g., amines, thiols, alcohols, phenols), as is typical for proteins.

Typically, the reactive group will react with an amine, a thiol, an alcohol, an aldehyde, a ketone, or with silica. Preferably, reactive groups react with an amine or a thiol functional group, or with silica. In one embodiment, the reactive group is an acrylamide, an activated ester of a carboxylic acid, an acyl azide, an acyl nitrile, an aldehyde, an alkyl halide, a silyl halide, an anhydride, an aniline, an aryl halide, an azide, an aziridine, a boronate, a diazoalkane, a haloacetamide, a halotriazine, a hydrazine (including hydrazides), an imido ester, an isocyanate, an isothiocyanate, a maleimide, a phosphoramidite, a reactive platinum complex, a sulfonyl halide, or a thiol group. By "reactive platinum complex" is particularly meant chemically reactive platinum complexes such as described in U.S. Pat. No. 5,714,327.

Where the reactive group is an activated ester of a carboxylic acid, such as a succinimidyl ester of a carboxylic acid, a sulfonyl halide, a tetrafluorophenyl ester or an isothiocyanates, the resulting compound is particularly useful for preparing conjugates of carrier molecules such as proteins, nucleotides, oligonucleotides, or haptens. Where the reactive group is a maleimide, haloalkyl or haloacetamide (including any reactive groups disclosed in U.S. Pat. Nos. 5,362,628; 5,352,803 and 5,573,904 (supra)) the resulting compound is particularly useful for conjugation to thiol-containing substances. Where the reactive group is a hydrazide, the resulting compound is particularly useful for conjugation to periodate-oxidized carbohydrates and glycoproteins, and in addition is an aldehyde-fixable polar tracer for cell microinjection. Where the reactive group is a silyl halide, the resulting compound is particularly useful for conjugation to silica surfaces, particularly where the silica surface is incorporated into a fiber optic probe subsequently used for remote ion detection or quantitation.

In a particular aspect, the reactive group is a photoactivatable group such that the group is only converted to a reactive species after illumination with an appropriate wavelength. An appropriate wavelength is generally a UV wavelength that is less than 400 nm. This method provides for specific attachment to only the target molecules, either in solution or immobilized on a solid or semi-solid matrix. Photoactivatable reactive groups include, without limitation, benzophenones, aryl azides and diazirines.

Preferably, the reactive group is a photoactivatable group, succinimidyl ester of a carboxylic acid, a haloacetamide, haloalkyl, a hydrazine, an isothiocyanate, a maleimide group, an aliphatic amine, a silyl halide, a cadaverine or a psoralen. More preferably, the reactive group is a succinimidyl ester of a carboxylic acid, a maleimide, an iodoacetamide, or a silyl halide. In a particular embodiment the reactive group is a succinimidyl ester of a carboxylic acid, a sulfonyl halide, a tetrafluorophenyl ester, an iosothiocyanates or a maleimide.

In another exemplary embodiment, the present compound is covalently bound to a carrier molecule. If the compound has a reactive group, then the carrier molecule can alternatively be linked to the compound through the reactive group. The reactive group may contain both a reactive functional moiety and a linker, or only the reactive functional moiety.

A variety of carrier molecules are useful in the present invention. Exemplary carrier molecules include antigens, steroids, vitamins, drugs, haptens, metabolites, toxins, environmental pollutants, amino acids, peptides, proteins, nucleic acids, nucleic acid polymers, carbohydrates, lipids, and polymers. In exemplary embodiment, at least one member selected from A, L or B comprises a carrier molecule. Preferably, at least one of A or B comprises a carrier molecule, wherein at least one of $R^3$, $R^4$, $R^6$ or $R^7$ is a carrier molecule or is attached to a carrier molecule. In another aspect, L comprises a carrier molecule; typically the E moiety is attached to a carrier molecule.

In an exemplary embodiment, the carrier molecule comprises an amino acid, a peptide, a protein, a polysaccharide, a nucleoside, a nucleotide, an oligonucleotide, a nucleic acid, a hapten, a psoralen, a drug, a hormone, a lipid, a lipid assembly, a synthetic polymer, a polymeric microparticle, a biological cell, a virus and combinations thereof. In another exemplary embodiment, the carrier molecule is selected from a hapten, a nucleotide, an oligonucleotide, a nucleic acid polymer, a protein, a peptide or a polysaccharide. In a preferred embodiment the carrier molecule is amino acid, a peptide, a protein, a polysaccharide, a nucleoside, a nucleotide, an oligonucleotide, a nucleic acid, a hapten, a psoralen, a drug, a hormone, a lipid, a lipid assembly, a tyramine, a synthetic polymer, a polymeric microparticle, a biological cell, cellular components, an ion chelating moiety, an enzymatic substrate or a virus. In another preferred embodiment, the carrier molecule is an antibody or fragment thereof, an antigen, an avidin or streptavidin, a biotin, a dextran, an IgG binding protein, a fluorescent protein, agarose, and a non-biological microparticle.

In an exemplary embodiment, the enzymatic substrate is selected from an amino acid, peptide, sugar, alcohol, alkanoic acid, 4-guanidinobenzoic acid, nucleic acid, lipid, sulfate, phosphate, —$CH_2OCOalkyl$ and combinations thereof. Thus, the enzyme substrates can be cleave by enzymes selected from the group consisting of peptidase, phosphatase, glycosidase, dealkylase, esterase, guanidinobenzotase, sulfatase, lipase, peroxidase, histone deacetylase, endoglycoceramidase, exonuclease, reductase and endonuclease.

In another exemplary embodiment, the carrier molecule is an amino acid (including those that are protected or are substituted by phosphates, carbohydrates, or $C_1$ to $C_{22}$ carboxylic acids), or a polymer of amino acids such as a peptide or protein. In a related embodiment, the carrier molecule contains at least five amino acids, more preferably 5 to 36 amino acids. Exemplary peptides include, but are not limited to, neuropeptides, cytokines, toxins, protease substrates, and protein kinase substrates. Other exemplary peptides may function as organelle localization peptides, that is, peptides that serve to target the conjugated compound for localization within a particular cellular substructure by cellular transport mechanisms. Preferred protein carrier molecules include enzymes, antibodies, lectins, glycoproteins, histones, albumins, lipoproteins, avidin, streptavidin, protein A, protein G, phycobiliproteins and other fluorescent proteins, hormones, toxins and growth factors. Typically, the protein carrier molecule is an antibody, an antibody fragment, avidin, streptavidin, a toxin, a lectin, or a growth factor. Exemplary haptens include biotin, digoxigenin and fluorophores.

In another exemplary embodiment, the carrier molecule comprises a nucleic acid base, nucleoside, nucleotide or a nucleic acid polymer, optionally containing an additional linker or spacer for attachment of a fluorophore or other ligand, such as an alkynyl linkage (U.S. Pat. No. 5,047,519), an aminoallyl linkage (U.S. Pat. No. 4,711,955) or other linkage. In another exemplary embodiment, the nucleotide carrier molecule is a nucleoside or a deoxynucleoside or a dideoxynucleoside.

Exemplary nucleic acid polymer carrier molecules are single- or multi-stranded, natural or synthetic DNA or RNA oligonucleotides, or DNA/RNA hybrids, or incorporating an unusual linker such as morpholine derivatized phosphates (AntiVirals, Inc., Corvallis Oreg.), or peptide nucleic acids such as N-(2-aminoethyl)glycine units, where the nucleic acid contains fewer than 50 nucleotides, more typically fewer than 25 nucleotides.

In another exemplary embodiment, the carrier molecule comprises a carbohydrate or polyol that is typically a polysaccharide, such as dextran, FICOLL, heparin, glycogen, amylopectin, mannan, inulin, starch, agarose and cellulose, or is a polymer such as a poly(ethylene glycol). In a related embodiment, the polysaccharide carrier molecule includes dextran, agarose or FICOLL.

In another exemplary embodiment, the carrier molecule comprises a lipid (typically having 6-25 carbons), including glycolipids, phospholipids, and sphingolipids. Alternatively, the carrier molecule comprises a lipid vesicle, such as a liposome, or is a lipoprotein (see below). Some lipophilic substituents are useful for facilitating transport of the conjugated dye into cells or cellular organelles.

Alternatively, the carrier molecule is a cell, cellular systems, cellular fragment, or subcellular particles, including virus particles, bacterial particles, virus components, biological cells (such as animal cells, plant cells, bacteria, or yeast), or cellular components. Examples of cellular components that are useful as carrier molecules include lysosomes, endosomes, cytoplasm, nuclei, histones, mitochondria, Golgi apparatus, endoplasmic reticulum and vacuoles.

In another exemplary embodiment, the carrier molecule non-covalently associates with organic or inorganic materials. Exemplary embodiments of the carrier molecule that possess a lipophilic substituent can be used to target lipid assemblies such as biological membranes or liposomes by non-covalent incorporation of the dye compound within the membrane, e.g., for use as probes for membrane structure or for incorporation in liposomes, lipoproteins, films, plastics, lipophilic microspheres or similar materials.

In an exemplary embodiment, the carrier molecule comprises a specific binding pair member wherein the present compounds are conjugated to a specific binding pair member and are used to detect nucleic acids. Alternatively, the presence of the labeled specific binding pair member indicates the location of the complementary member of that specific binding pair; each specific binding pair member having an area on the surface or in a cavity which specifically binds to, and is complementary with, a particular spatial and polar organization of the other. Exemplary binding pairs are set forth in Table 2.

TABLE 2

| Representative Specific Binding Pairs | |
|---|---|
| antigen | antibody |
| biotin | avidin (or streptavidin or anti-biotin) |
| IgG* | protein A or protein G |
| drug | drug receptor |
| folate | folate binding protein |
| toxin | toxin receptor |

TABLE 2-continued

Representative Specific Binding Pairs

| antigen | antibody |
|---|---|
| carbohydrate | lectin or carbohydrate receptor |
| peptide | peptide receptor |
| protein | protein receptor |
| enzyme substrate | enzyme |
| DNA (RNA) | cDNA (cRNA)† |
| hormone | hormone receptor |
| ion | chelator |

*IgG is an immunoglobulin
†cDNA and cRNA are the complementary strands used for hybridization In an exemplary embodiment, the present compounds of the invention are covalently bonded to a solid support. The solid support may be attached to the compound either through the A, L or B moiety, or through a reactive group, if present, or through a carrier molecule, if present. Even if a reactive group and/or a carrier molecule are present, the solid support may be attached through the A, L or B moiety. In exemplary embodiment, at least one member selected from A, L or B comprises a solid support. Preferably, at least one of A or B comprises a solid support, wherein at least one of $R^3$, $R^4$, $R^6$ or $R^7$ is a solid support or is attached to a solid support. In another aspect, L comprises a solid support; typically the E moiety is attached to a solid support.

A solid support suitable for use in the present invention is typically substantially insoluble in liquid phases. Solid supports of the current invention are not limited to a specific type of support. Rather, a large number of supports are available and are known to one of ordinary skill in the art. Thus, useful solid supports include solid and semi-solid matrixes, such as aerogels and hydrogels, resins, beads, biochips (including thin film coated biochips), microfluidic chip, a silicon chip, multi-well plates (also referred to as microtitre plates or microplates), membranes, conducting and nonconducting metals, glass (including microscope slides) and magnetic supports. More specific examples of useful solid supports include silica gels, polymeric membranes, particles, derivatized plastic films, glass beads, cotton, plastic beads, alumina gels, polysaccharides such as Sepharose, poly(acrylate), polystyrene, poly(acrylamide), polyol, agarose, agar, cellulose, dextran, starch, FICOLL, heparin, glycogen, amylopectin, mannan, inulin, nitrocellulose, diazocellulose, polyvinylchloride, polypropylene, polyethylene (including poly (ethylene glycol)), nylon, latex bead, magnetic bead, paramagnetic bead, superparamagnetic bead, starch and the like.

In some embodiments, the solid support may include a solid support reactive functional group, including, but not limited to, hydroxyl, carboxyl, amino, thiol, aldehyde, halogen, nitro, cyano, amido, urea, carbonate, carbamate, isocyanate, sulfone, sulfonate, sulfonamide, sulfoxide, etc., for attaching the compounds of the invention. Useful reactive groups are disclosed above and are equally applicable to the solid support reactive functional groups herein.

A suitable solid phase support can be selected on the basis of desired end use and suitability for various synthetic protocols. For example, where amide bond formation is desirable to attach the compounds of the invention to the solid support, resins generally useful in peptide synthesis may be employed, such as polystyrene (e.g., PAM-resin obtained from Bachem Inc., Peninsula Laboratories, etc.), POLYHIPE™ resin (obtained from Aminotech, Canada), polyamide resin (obtained from Peninsula Laboratories), polystyrene resin grafted with polyethylene glycol (TentaGel™, Rapp Polymere, Tubingen, Germany), polydimethyl-acrylamide resin (available from Milligen/Biosearch, California), or PEGA beads (obtained from Polymer Laboratories).

Preparation of Conjugates

Conjugates of components (carrier molecules or solid supports), e.g., drugs, peptides, toxins, nucleotides, phospholipids and other organic molecules are prepared by organic synthesis methods using the reactive reporter molecules of the invention, are generally prepared by means well recognized in the art (Haugland, MOLECULAR PROBES HANDBOOK, supra, (2002)). Preferably, conjugation to form a covalent bond consists of simply mixing the reactive compounds of the present invention in a suitable solvent in which both the reactive compound and the substance to be conjugated are soluble. The reaction preferably proceeds spontaneously without added reagents at room temperature or below. For those reactive compounds that are photoactivated, conjugation is facilitated by illumination of the reaction mixture to activate the reactive compound. Chemical modification of water-insoluble substances, so that a desired compound-conjugate may be prepared, is preferably performed in an aprotic solvent such as dimethylformamide, dimethylsulfoxide, acetone, ethyl acetate, toluene, or chloroform. Similar modification of water-soluble materials is readily accomplished through the use of the instant reactive compounds to make them more readily soluble in organic solvents.

Preparation of Peptide or Protein Conjugates Typically Comprises First Dissolving the Protein to be conjugated in aqueous buffer at about. 1-10 mg/mL at room temperature or below. Bicarbonate buffers (pH about 8.3) are especially suitable for reaction with succinimidyl esters, phosphate buffers (pH about 7.2-8) for reaction with thiol-reactive functional groups and carbonate or borate buffers (pH about 9) for reaction with isothiocyanates and dichlorotriazines. The appropriate reactive compound is then dissolved in an aprotic solvent (usually DMSO or DMF) in an amount sufficient to give a suitable degree of labeling when added to a solution of the protein to be conjugated. The appropriate amount of compound for any protein or other component is conveniently predetermined by experimentation in which variable amounts of the compound are added to the protein, the conjugate is chromatographically purified to separate unconjugated compound and the compound-protein conjugate is tested in its desired application.

Following addition of the reactive compound to the component solution, the mixture is incubated for a suitable period (typically about 1 hour at room temperature to several hours on ice), the excess compound is removed by gel filtration, dialysis, HPLC, adsorption on an ion exchange or hydrophobic polymer or other suitable means. The compound-conjugate is used in solution or lyophilized. In this way, suitable conjugates can be prepared from antibodies, antibody fragments, avidins, lectins, enzymes, proteins A and G, cellular proteins, albumins, histones, growth factors, hormones, and other proteins.

Conjugates of polymers, including biopolymers and other higher molecular weight polymers are typically prepared by means well recognized in the art (for example, Brinkley et al., *Bioconjugate Chem.*, 3: 2 (1992)). In these embodiments, a single type of reactive site may be available, as is typical for polysaccharides) or multiple types of reactive sites (e.g. amines, thiols, alcohols, phenols) may be available, as is typical for proteins. Selectivity of labeling is best obtained by selection of an appropriate reactive dye. For example, modification of thiols with a thiol-selective reagent such as a haloacetamide or maleimide, or modification of amines with an amine-reactive reagent such as an activated ester, acyl azide, isothiocyanate or 3,5-dichloro-2,4,6-triazine. Partial selectivity can also be obtained by careful control of the reaction conditions.

When modifying polymers with the compounds, an excess of compound is typically used, relative to the expected degree of compound substitution. Any residual, unreacted compound or a compound hydrolysis product is typically removed by dialysis, chromatography or precipitation. Presence of residual, unconjugated dye can be detected by thin layer chromatography using a solvent that elutes the dye away from its conjugate. In all cases it is usually preferred that the reagents be kept as concentrated as practical so as to obtain adequate rates of conjugation.

In an exemplary embodiment, the conjugate of the invention is associated with an additional substance, that binds either to the reporter molecule or the conjugated substance (carrier molecule or solid support) through noncovalent interaction. In another exemplary embodiment, the additional substance is an antibody, an enzyme, a hapten, a lectin, a receptor, an oligonucleotide, a nucleic acid, a liposome, or a polymer. The additional substance is optionally used to probe for the location of the dye-conjugate, for example, as a means of enhancing the signal of the dye-conjugate.

Nucleic Acid Reporter Molecules

The above described unsymmetrical cyanine monomer moieties and linkers can be combined in numerous ways resulting in the nucleic acid reporter molecules of the present invention that are hetero- or homodimers. Typically, the monomer moieties form dimers via the pyridinium or quinolinium moieties wherein the linker is covalently bonded to the pyridinium or quinolinium moieties of both monomer moieties. In this way, the present unsymmetrical cyanine dimer compounds have the general formula, A-L-B or A-L*-B. More specifically, the present nucleic acid reporter molecules have the following formula:

wherein X, $R^3$, $R^4$, K and j are as defined above. The monomer moieties may be the same or different resulting in homo- or heterodimer compounds Selected nucleic reporter molecules of the present invention include:

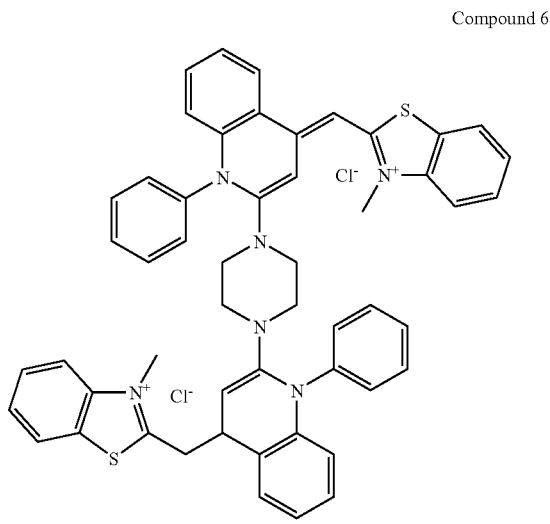

Compound 6 wherein X is S, the monomer moieties are the same and are according to Formula (III)(a) and the linker is according to Formula (II)(i),

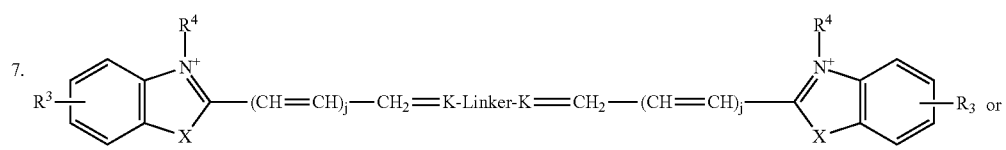

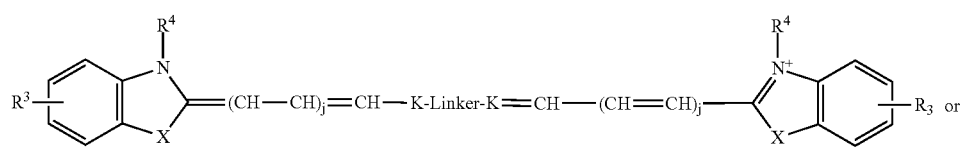

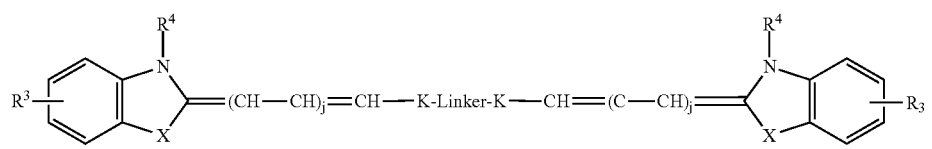

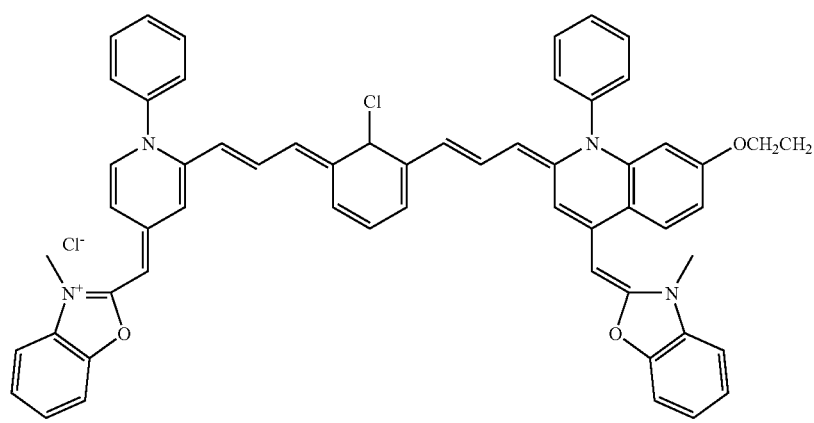

(Compound 26)

Compound 26, wherein X is O and the monomer moieties are different forming a heterodimer wherein one monomer is according to Formula (III)(b), the second monomer is according to Formula (III)(e) and the linker is according to Formula (IV)(iv),

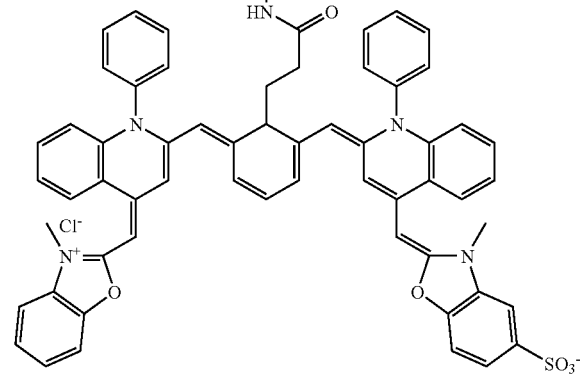

(Compound 27)

Compound 27, wherein X is O and the monomers are according to Formula (III)(a) and the linker is according to Formula (II)(f),

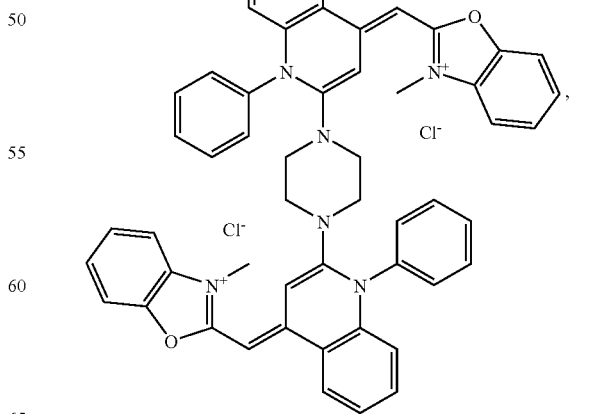

(Compound 28)

Compound 28, wherein X is S and the monomers are according to Formula (III)(a) and the linker is according to Formula (I), Compound 20 wherein X is O, (Compound 11)

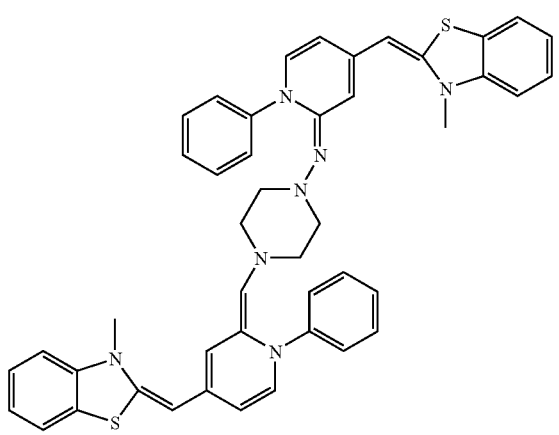

Compound 11 wherein X is S, the monomer moieties are the same and are according to Formula (III)(b) and the linker is according to Formula (II)(j), Compound 19

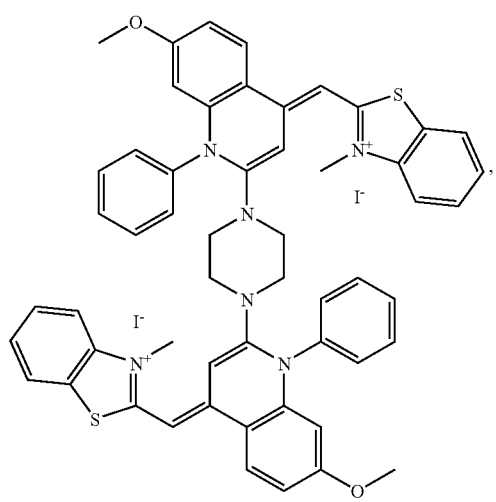

wherein the monomer moieties are the same and are according to Formula (III)(e) and the linker is according to Formula (II)(i), Compound 23

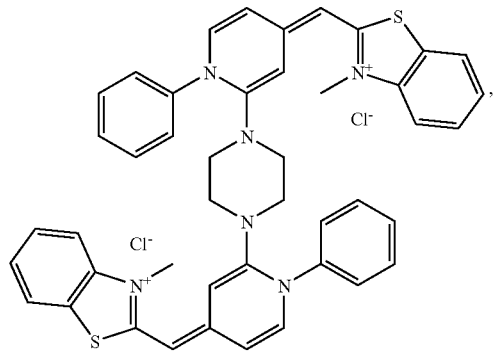

wherein the monomer moieties are the same and are according to Formula (III)(b) and the linker is according to Formula (II)(i), and Compound 25 wherein K represents a pyridinium moiety (Formula (III)(a)) for one of the cyanine monomers and a quinolinium moiety (Formula (III)(b)) for the other cyanine monomer. The linker is according to Formula (II)(j).

Presently preferred for detection of intracellular RNA are compounds 6 and 19. Presently preferred compounds for the detection of extracellular RNA are compounds 11, 20 and 23.

B. Methods of Use

The present nucleic acid reporter molecules may be utilized without limit for the fluorescent detection of nucleic acid polymers in a test sample. The methods for the detection of single, double, triple or quadruple stranded DNA and RNA or a combination thereof comprises contacting a sample with a staining solution to prepare a labeling mixture, incubating the sample with the staining solution for a sufficient amount of time for the present reporter molecules to complex with the nucleic acid, illuminating the sample with an appropriate wavelength and observing the illuminated labeling mixture whereby the nucleic acid polymer is detected.

The staining solution is typically prepared by dissolving a present nucleic acid reporter molecule in an aqueous solvent such as water, a buffer solution, such as phosphate buffered saline, or an organic solvent such as dimethylsulfoxide (DMSO), dimethylformamide (DMF), methanol, ethanol or acetonitrile. Typically, the present nucleic reporter molecules are first dissolved in an organic solvent such as DMSO as a stock solution. The stock solution is then diluted to an effective working concentration in an aqueous solution optionally comprising appropriate buffering components. An effective working concentration of the present compounds is the amount sufficient to give a detectable fluorescent response when complexed with nucleic acid polymers. Typically, the effective amount is about 100 nm to 100 μM. Most preferred is about 600 nm to 10 μM. It is generally understood that the specific amount of the nucleic acid reporter molecules present in a staining solution is determined by the physical nature of the sample and the nature of the analysis being performed.

The sample may be combined with the staining solution by any means that facilitates contact between the nucleic acid reporter molecules and the nucleic acid. The contact can occur through simple mixing, as in the case where the sample is a solution. The present reporter molecules may be added to the nucleic acid solution directly or may contact the solution on an inert matrix such as a blot or gel, a testing strip, a microarray, or any other solid or semi-solid surface, for example where only a simple and visible demonstration of the presence of nucleic acids is desired. Any inert matrix used to separate the sample can be used to detect the presence of nucleic acids by observing the fluorescent response on the inert matrix. While the present reporter molecules have shown an ability to permeate cellular membranes rapidly and completely upon addition of the staining solution, any other technique that is suitable for transporting the reporter molecules across cell membranes with minimal disruption of the viability of the cell and integrity of cell membranes is also a valid method of combining the sample with the present reporter molecules for detection of intracellular nucleic acid. Examples of suitable processes include action of chemical agents such as detergents, enzymes or adenosine triphosphate; receptor- or transport protein-mediated uptake; pore-forming proteins; microinjection; electroporation; hypoosmotic shock; or minimal physical disruption such as scrape loading or bombardment with solid particles coated with or in the presence of the present reporter molecules.

The sample is incubated in the presence of the nucleic acid reporter molecules for a time sufficient to form the fluorescent nucleic acid-reporter molecule complex. Detectable fluorescence in a solution of nucleic acids is essentially instantaneous. Detectable fluorescence within cell membranes requires the permeation of the dye into the cell. In general, visibly detectable fluorescence can be obtained in a wide variety of cells with embodiments of the present invention within about 10-30 minutes after combination with the sample, commonly within about 10-20 minutes. While permeation and fluorescence is rapid for all reporter molecules comprising an aromatic substituent on the pyridinium or quinolinium moiety of the cyanine monomer moiety, it is readily apparent to one skilled in the art that the time necessary for sufficient permeation of the dye, or sufficient formation of the fluorescent nucleic acid complex, is dependent upon the physical and chemical nature of the individual sample and the sample medium.

To facilitate the detection of the nucleic acid-reporter molecule complex, the excitation or emission properties of the fluorescent complex are utilized. For example, the sample is excited by a light source capable of producing light at or near the wavelength of maximum absorption of the fluorescent complex, such as an ultraviolet or visible lamp, an arc lamp, a laser, or even sunlight. Preferably the fluorescent complex is excited at a wavelength equal to or greater than about 300 nm, more preferably equal to or greater than about 340 nm. The fluorescence of the complex is detected qualitatively or quantitatively by detection of the resultant light emission at a wavelength greater than about 400 nm, more preferably greater than about 450 nm, most preferred greater than 480 nm. The emission is detected by means that include visible inspection, photographic film, or the use of current instrumentation such as fluorometers, quantum counters, plate readers, epifluorescence microscopes and flow cytometers or by means for amplifying the signal such as a photomultiplier.

The present invention also provides specific compounds and methods for detecting RNA in the presence of DNA, wherein the method comprises the following steps:

a) combining a present nucleic acid reporter molecule with a sample wherein the reporter molecule is capable of producing a fluorescent intensity signal that is greater on RNA than on DNA to prepare a labeling mixture;

b) incubating the labeling mixture for a sufficient amount of time for said nucleic acid reporter molecule to associate with RNA in the sample; and, c) illuminating the labeling mixture with an appropriate wavelength; and d) observing the illuminated labeling mixture whereby the RNA is detected in the presence of DNA.

The present nucleic acid reporter molecules that are capable of producing a fluorescent intensity signal that is greater on RNA than on DNA are determined empirically, See Examples 35 and 36 and Table 3. However, we have found that cyanine monomer moieties that comprise a monomethine bridge and a rigid linker according to Formula (II)(b), (II)(i), (II)(ia), (II)(ib) and (II)(j) produce nucleic acid reporter molecules that have a greater fluorescent intensity signal on RNA than on DNA. It is not intended that only this class of present nucleic acid reporter molecules are capable of having a greater fluorescent intensity signal on RNA than DNA as other classes within the scope of the invention may also be used to detect RNA in the presence of DNA. Without wishing to be bound by a theory, it appears that the reporter molecules capable of fluorescing brighter on RNA than on DNA preferentially complex with RNA. This may be due to the size of the helical groove of RNA for which rigid linkers according to Formula (II)(a), (II)(b), (II)(i) and (II)(j) preferentially form a RNA-reporter molecule complex. Thus, preferred compounds for the detection of RNA include Compound 6, 11, 19, 20 and 23.

The foregoing methods having been described it is understood that the many and varied compounds of the present invention can be utilized with the many methods. The compounds not being limited to just those that are specifically disclosed.

In an exemplary embodiment the present methods employ a nucleic acid reporter molecule that comprises a first nucleic acid complexing monomer moiety, a second nucleic acid complexing monomer moiety and a linker that comprises at least one aromatic, heteroaromatic, cyclic or heterocyclic moiety comprising 3-20 non-hydrogen atoms selected from the group consisting of O, N, S, P and C, wherein the first nucleic acid complexing monomer moiety is covalently attached to the linker; and the second nucleic acid complexing monomer moiety is covalently attached to the linker. In one aspect, the first and the second first nucleic acid complexing monomer moieties are the same wherein the present compound is a homodimer. In another aspect, the first and the second first nucleic acid complexing monomer moieties are different wherein the present compound is a heterodimer.

In an exemplary embodiment of the methods the nucleic acid complexing monomer moiety is an unsymmetrical cyanine monomer moiety, wherein the present nucleic acid reporter molecule comprises a first unsymmetrical cyanine monomer moiety, a second unsymmetrical cyanine monomer moiety, and a linker that comprises at least one aromatic, heteroaromatic, cyclic or heterocyclic moiety comprising 3-20 non-hydrogen atoms selected from the group consisting of O, N, S, P and C, wherein the first unsymmetrical cyanine monomer moiety is covalently attached to the linker; and the second unsymmetrical cyanine monomer moiety is covalently attached to the linker. In one aspect the first and the second unsymmetrical cyanine monomer moieties are the same, wherein the present compound is cyanine homodimer. In another aspect, the first and the second unsymmetrical cyanine monomer moieties are different, wherein the present compound is a cyanine heterodimer.

In an exemplary embodiment the methods employ a present nucleic acid reporter molecule is according to the formula:

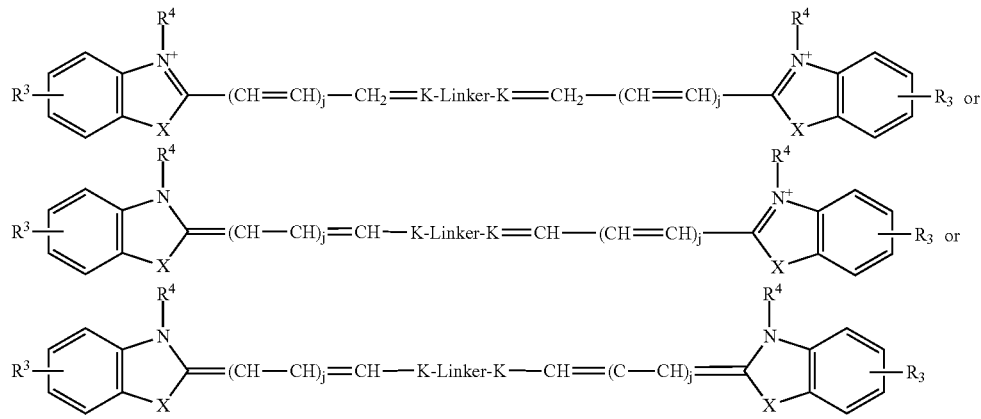

wherein each R³ is independently hydrogen, unsubstituted C₁-C₆ alkyl substituted C₁-C₆ alkyl unsubstituted C₁-C₆ alkoxy, substituted C₁-C₆ alkoxy, unsubstituted fused benzene, substituted fused benzene, unsubstituted trifluoromethyl, substituted trifluoromethyl, unsubstituted halogen, substituted halogen, unsubstituted reactive group, substituted reactive group, unsubstituted carrier molecule, substituted carrier molecule, unsubstituted solid support or substituted solid support;

each R⁴ is independently a unsubstituted C₁-C₆ alkyl substituted C₁-C₆ alkyl unsubstituted reactive group, substituted reactive group, unsubstituted carrier molecule, substituted carrier molecule, unsubstituted solid support or substituted solid support;

X is O, S, or CR⁶R⁷ wherein each R⁶ and R⁷ are independently a unsubstituted C₁-C₆ alkyl substituted C₁-C₆ alkyl unsubstituted reactive group, substituted reactive group, unsubstituted carrier molecule, substituted carrier molecule, unsubstituted solid support, substituted solid support or R⁶ and R⁷ taken together form a 5- or 6-membered saturated ring;

j is 0, 1, or 2;

linker is a series of stable covalent bonds comprising 1-30 nonhydrogen atoms selected from the group consisting of C, N, O, S and P; and, K is substituted pyridinium, unsubstituted pyridinium, substituted quinolinium, or unsubstituted quinolinium.

Thus, in one embodiment, the unsymmetrical cyanine monomer is according to the formula:

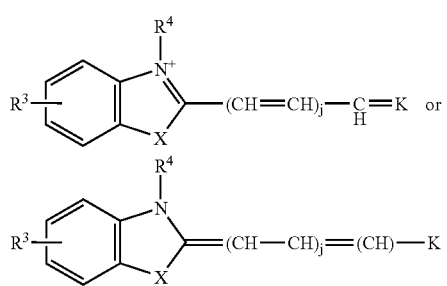

wherein the linker is covalently attached to the K moiety of the cyanine monomer.

Thus, in a particular embodiment, when the linker does not comprises at least one aromatic, heteroaromatic, cyclic or heterocyclic moiety, the methods use Compound 1, Compound 2, Compound 3, Compound 5, Compound 12, Compound 13, Compound 17, and Compound 22. These compounds are cell permeable and in a particularly useful embodiment Compound 1 is used to selectively detect mitochondrial DNA, See Example 43.

In another exemplary embodiment of the methods, a nucleic acid reporter molecule comprising a first unsymmetrical cyanine monomer moiety, a second unsymmetrical cyanine monomer moiety, and a linker having formula (I) —(Y)$_r$—(CH$_2$)$_m$-T$_q$-(CH$_2$)$_n$-E-(CH$_2$)$_n$-T$_q$-(CH$_2$)$_m$—(Y)$_r$— is employed. Y is a linear or branched moiety comprising 1-20 non-hydrogen atoms selected from the group consisting of C, N, O, P and S; T is a unsubstituted heteroatom or a substituted heteroatom; E is an aromatic, heteroaromatic, cyclic or heterocyclic moiety comprising 3-20 non-hydrogen atoms selected from the group consisting of O, N, S, P and C; r is independently 0 or 1; m is an integer of 0-6; n is independently 0 or 1; q is independently 0 or 1; and wherein the first unsymmetrical cyanine monomer moiety is covalently attached to the linker; and the second unsymmetrical cyanine monomer moiety is covalently attached to the linker.

In one aspect, E of the linker is

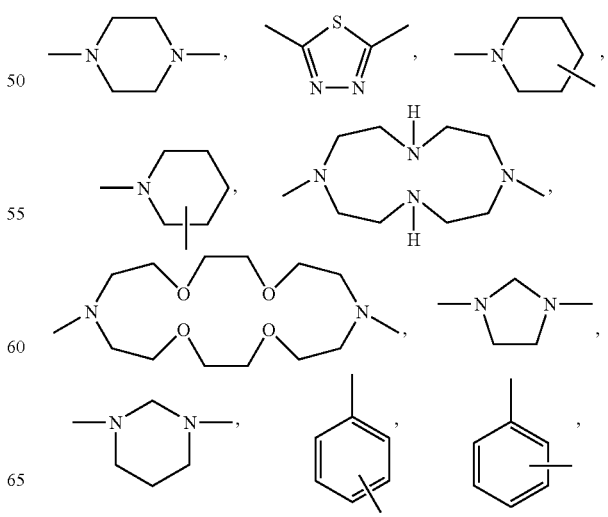

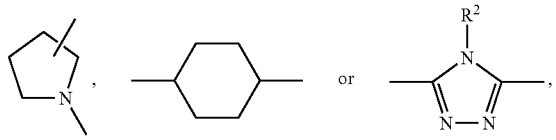

wherein $R^2$ is hydrogen, amine, substituted amine, substituted $C_1$-$C_6$ alkyl, unsubstituted $C_1$-$C_6$ alkyl, unsubstituted reactive group, substituted reactive group, unsubstituted carrier molecule, substituted carrier molecule, unsubstituted solid support, or substituted solid support. In a further aspect T of the linker, when present, is —$NR^2$, —N═ or S wherein the $R^2$ is hydrogen, amine, substituted amine, substituted $C_1$-$C_6$ alkyl, unsubstituted $C_1$-$C_6$ alkyl, unsubstituted reactive group, substituted reactive group, unsubstituted carrier molecule, substituted carrier molecule, unsubstituted solid support, or substituted solid support.

In an exemplary embodiment, the nucleic aid reporter molecule of the present methods comprise a reactive group, solid support and carrier molecule wherein these substituents independently comprise a linker that is a single covalent bond, or a covalent linkage that is linear or branched, cyclic or heterocyclic, saturated or unsaturated, having 1-20 nonhydrogen atoms selected from the group consisting of C, N, P, O and S; and are composed of any combination of ether, thioether, amine, ester, carboxamide, sulfonamide, hydrazide bonds and aromatic or heteroaromatic bonds.

In an exemplary embodiment, the reactive group is selected from the group consisting of an acrylamide, an activated ester of a carboxylic acid, a carboxylic ester, an acyl azide, an acyl nitrile, an aldehyde, an alkyl halide, an anhydride, an aniline, an amine, an aryl halide, an azide, an aziridine, a boronate, a diazoalkane, a haloacetamide, a haloalkyl, a halotriazine, a hydrazine, an imido ester, an isocyanate, an isothiocyanate, a maleimide, a phosphoramidite, a reactive platinum complex, a silyl halide, a sulfonyl halide, a thiol and a photoactivatable group. In a further aspect, the reactive group is selected from the group consisting of carboxylic acid, succinimidyl ester of a carboxylic acid, hydrazide, amine and a maleimide.

In an exemplary embodiment the carrier molecule is selected from the group consisting of an amino acid, a peptide, a protein, a polysaccharide, a nucleoside, a nucleotide, an oligonucleotide, a nucleic acid polymer, a hapten, a psoralen, a drug, a hormone, a lipid, a lipid assembly, a synthetic polymer, a polymeric microparticle, a biological cell or a virus. In a further aspect, the carrier molecule is selected from the group consisting of an antibody or fragment thereof, an avidin or streptavidin, a biotin, a blood component protein, a dextran, an enzyme, an enzyme inhibitor, a hormone, an IgG binding protein, a fluorescent protein, a growth factor, a lectin, a lipopolysaccharide, a microorganism, a metal binding protein, a metal chelating moiety, a non-biological microparticle, a peptide toxin, a phosphotidylserine-binding protein, a structural protein, a small-molecule drug, or a tyramide.

In an exemplary embodiment, the solid support is selected from the group consisting of a microfluidic chip, a silicon chip, a microscope slide, a microplate well, silica gels, polymeric membranes, particles, derivatized plastic films, glass beads, cotton, plastic beads, alumina gels, polysaccharides, polyvinylchloride, polypropylene, polyethylene, nylon, latex bead, magnetic bead, paramagnetic bead, and superparamagnetic bead. In a further aspect, the solid support is selected from the group consisting of Sepharose, poly(acrylate), polystyrene, poly(acrylamide), polyol, agarose, agar, cellulose, dextran, starch, FICOLL, heparin, glycogen, amylopectin, mannan, inulin, nitrocellulose, diazocellulose and starch.

In an exemplary embodiment of the present methods, the linker of the nucleic acid reporter molecule is

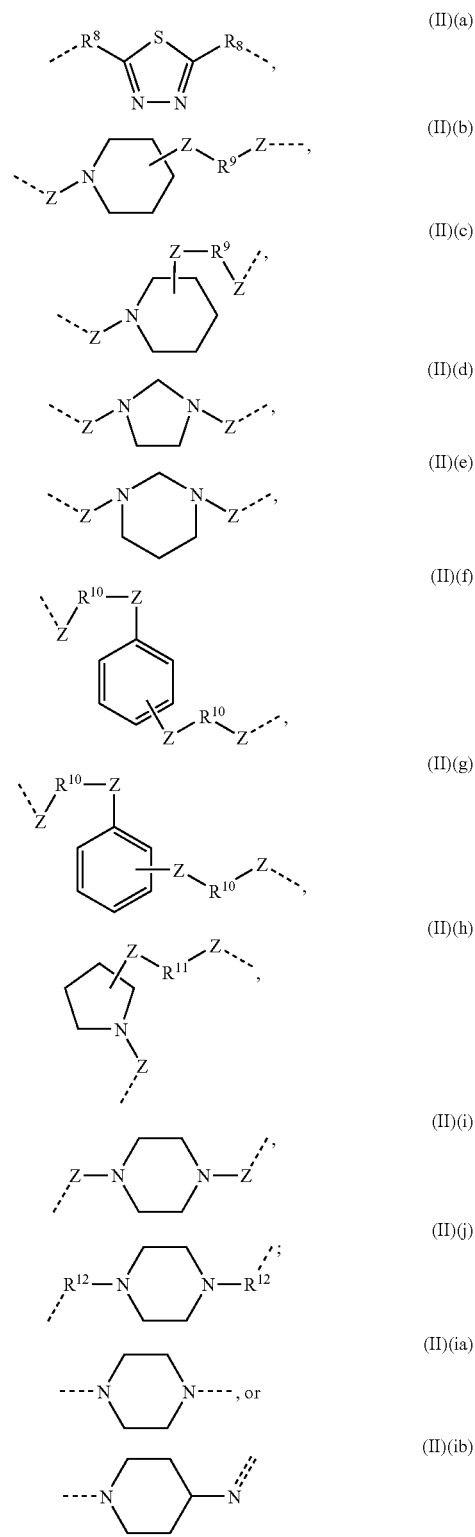

Wherein each $R^8$, $R^9$, $R^{10}$, $R^{11}$ and $R^{12}$ are independently a —$NR^2$, —N= or S wherein $R^2$ is hydrogen, amine, substituted amine, substituted $C_1$-$C_6$ alkyl, unsubstituted $C_1$-$C_6$ alkyl, unsubstituted reactive group, substituted reactive group, unsubstituted carrier molecule, substituted carrier molecule, unsubstituted solid support, or substituted solid support; each Z is independently —$(CH_2)_g$— wherein g is 0 or 1, wherein the dashed line is attached directly to the K moiety of the unsymmetrical cyanine monomer. In one aspect $R^8$ is S. In a further aspect, $R^{12}$ is —NH or —N=.

Particularly preferred for the detection of nucleic acid are reporter molecules wherein the linker is

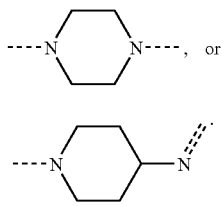

(II)(ia), or (II)(ib)

In a particularly preferred embodiment, the nucleic acid reporter molecules are employed to detect RNA in the presence of DNA wherein the nucleic acid reporter molecule has a RNA/DNA ratio of fluorescence enhancement greater than about one. In this instance the nucleic acid reporter molecule comprises a first monomethine unsymmetrical cyanine monomer moiety, a second monomethine unsymmetrical cyanine monomer moiety and a linker that is

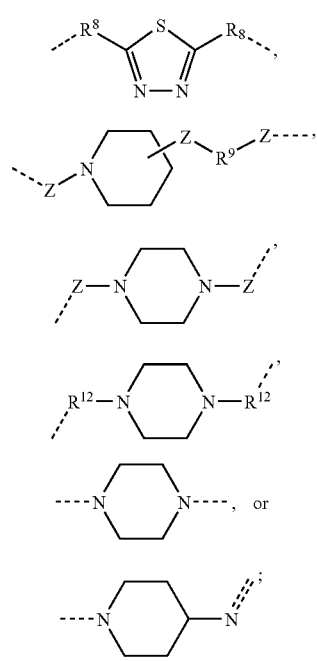

(II)(a)

(II)(b)

(II)(i)

(II)(j)

(II)(ia)

(II)(ib)

wherein $R^8$ is a substituted heteroatom or an unsubstituted heteroatom; $R^9$ is a substituted heteroatom or an unsubstituted heteroatom; $R^{12}$ is a substituted heteroatom or an unsubstituted heteroatom; each Z is —$(CH_2)_g$ wherein g is 0 or 1; and the first unsymmetrical cyanine monomer moiety is covalently attached to the linker; and the second unsymmetrical cyanine monomer moiety is covalently attached to the linker. In a further embodiment, $R^8$, $R^9$ and $R^{12}$ are —$NR^2$— N= or S wherein $R^2$ is hydrogen, amine, substituted amine, substituted $C_1$-$C_6$ alkyl, unsubstituted $C_1$-$C_6$ alkyl, unsubstituted reactive group, substituted reactive group, unsubstituted carrier molecule, substituted carrier molecule, unsubstituted solid support, or substituted solid support. In one aspect, Compound 6 is preferred for the detection of intracellular RNA.

In an exemplary embodiment, the monomethine unsymmetrical cyanine monomer moiety has the general formula:

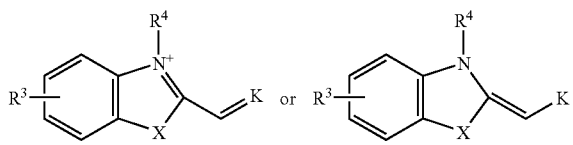

wherein $R^3$, R4, X and K are as defined above.

Sample Preparation

The end user will determine the choice of the sample and the way in which the sample is prepared but the sample is typically prepared using methods well known in the art for isolating nucleic acid for in vitro and solution based assay detection or well know methods for live cell or fixed cells for intracellular and/or in vivo detection of nucleic acids. The sample includes, without limitation, any biological derived material that is thought to contain a nucleic acid polymer. Alternatively, samples also include material that nucleic acid polymers have been added to such as a PCR reaction mixture, a polymer gel such as agarose or polyacrylamide gels or a microfluidic assay system. In another aspect of the invention, the sample can also include a buffer solution that contains nucleic acid polymers to determine the present reporter molecules that are ideal under different assay conditions or to determine the present reporter molecules that are preferential RNA reporters.

The sample can be a biological fluid such as whole blood, plasma, serum, nasal secretions, sputum, saliva, urine, sweat, transdermal exudates, cerebrospinal fluid, or the like. Biological fluids also include tissue and cell culture medium wherein an analyte of interest has been secreted into the medium. Alternatively, the sample may be whole organs, tissue or cells from the animal. Examples of sources of such samples include muscle, eye, skin, gonads, lymph nodes, heart, brain, lung, liver, kidney, spleen, thymus, pancreas, solid tumors, macrophages, mammary glands, mesothelium, and the like. Cells include without limitation prokaryotic cells such as bacteria, yeast, fungi, mycobacteria and mycoplasma, and eukaryotic cells such as nucleated plant and animal cells that include primary cultures and immortalized cell lines. Typically prokaryotic cells include *E. coli* and *S. aureus*. Eukaryotic cells include without limitation ovary cells, epithelial cells, circulating immune cells, β cells, hepatocytes, and neurons.

The nucleic acid may be either natural (biological in origin) or synthetic (prepared artificially). The nucleic acid may be present as nucleic acid fragments, oligonucleotides, or nucleic acid polymers. The nucleic acid may be present in a condensed phase, such as a chromosome. The presence of the nucleic acid in the sample may be due to a successful or unsuccessful experimental methodology, undesirable contamination, or a disease state. Nucleic acid may be present in all, or only part, of a sample, and the presence of nucleic acids may be used to distinguish between individual samples, or to differentiate a portion or region within a single sample.

The nucleic acid may be enclosed in a biological structure, for example contained within a viral particle, an organelle, or within a cell. The nucleic acids enclosed in biological structures may be obtained from a wide variety of environments, including cultured cells, organisms or tissues, unfiltered or separated biological fluids such as urine, cerebrospinal fluid, blood, lymph fluids, tissue homogenate, mucous, saliva, stool, or physiological secretions or environmental samples such as soil, water and air. The nucleic acid may be endogenous or introduced as foreign material, such as by infection or by transfection. The present nucleic acid reporter molecules can also be used for staining nucleic acids in a cell or cells that is fixed and treated with routine histochemical or cytochemical procedures (See, Examples 29-31).

Alternatively, the nucleic acid is not enclosed within a biological structure, but is present as a sample solution. The sample solution can vary from one of purified nucleic acids to crude mixtures such as cell extracts, biological fluids and environmental samples. In some cases it is desirable to separate the nucleic acids from a mixture of biomolecules or fluids in the solution prior to combination with the present reporter molecules. Numerous, well known, techniques exist for separation and purification of nucleic acids from generally crude mixtures with other proteins or other biological molecules. These include such means as electrophoretic techniques and chromatographic techniques using a variety of supports.

Illumination

The sample containing a nucleic acid-reporter molecule complex is illuminated with a wavelength of light selected to give a detectable optical response, and observed with a means for detecting the optical response. Equipment that is useful for illuminating the present compounds and compositions of the invention includes, but is not limited to, hand-held ultraviolet lamps, mercury arc lamps, xenon lamps, lasers and laser diodes. These illumination sources are optically integrated into laser scanners, fluorescence microplate readers or standard or microfluorometers.

The optical response is optionally detected by visual inspection, or by use of any of the following devices: CCD camera, video camera, photographic film, laser-scanning devices, fluorometers, photodiodes, quantum counters, epifluorescence microscopes, scanning microscopes, flow cytometers, fluorescence microplate readers, or by means for amplifying the signal such as photomultiplier tubes. Where the sample is examined using a flow cytometer, examination of the sample optionally includes sorting portions of the sample according to their fluorescence response.

The wavelengths of the excitation and emission bands of the nucleic acid reporter molecules vary with reporter molecule composition to encompass a wide range of illumination and detection bands. This allows the selection of individual reporter molecules for use with a specific excitation source or detection filter. In particular, present reporter molecules can be selected that possess excellent correspondence of their excitation band with the 488 nm band of the commonly used argon laser or emission bands which are coincident with preexisting filters Kits of the Invention Suitable kits for forming a nucleic acid-reporter molecule complex and detecting the nucleic acid also form part of the invention. Such kits can be prepared from readily available materials and reagents and can come in a variety of embodiments. The contents of the kit will depend on the design of the assay protocol or reagent for detection or measurement. All kits will contain instructions, appropriate reagents, and present nucleic acid reporter molecules. Typically, instructions include a tangible expression describing the reagent concentration or at least one assay method parameter such as the relative amounts of reagent and sample to be added together, maintenance time periods for reagent/sample admixtures, temperature, buffer conditions and the like to allow the user to carry out any one of the methods or preparations described above.

Thus in one aspect of the invention, a kit for detecting nucleic acid in a sample comprises a) a present nucleic acid reporter molecule.

In a further aspect the kit comprises instructions for detecting the nucleic acid, presently preferred are instructions for detecting RNA. In another aspect the kit may contain one or more of the following; sample preparation reagents, a buffering agent, an organic solvent or an additional nucleic acid reporter molecule.

The additional nucleic acid reporter molecule is typically one that distinguishes a different aspect of the sample of nucleic acid from the present reporter molecule.

The foregoing kits having been described it is understood that the many and varied compounds of the present invention can be utilized with the many kits. The compounds not being limited to just those that are specifically disclosed.

In an exemplary embodiment the present kits employ a nucleic acid reporter molecule that comprises a first nucleic acid complexing monomer moiety, a second nucleic acid complexing monomer moiety and a linker that comprises at least one aromatic, heteroaromatic, cyclic or heterocyclic moiety comprising 3-20 non-hydrogen atoms selected from the group consisting of O, N, S, P and C, wherein the first nucleic acid complexing monomer moiety is covalently attached to the linker; and the second nucleic acid complexing monomer moiety is covalently attached to the linker. In one aspect, the first and the second first nucleic acid complexing monomer moieties are the same wherein the present compound is a homodimer. In another aspect, the first and the second first nucleic acid complexing monomer moieties are different wherein the present compound is a heterodimer.

In an exemplary embodiment of the kits the nucleic acid complexing monomer moiety is an unsymmetrical cyanine monomer moiety, wherein the present nucleic acid reporter molecule comprises a first unsymmetrical cyanine monomer moiety, a second unsymmetrical cyanine monomer moiety, and a linker that comprises at least one aromatic, heteroaromatic, cyclic or heterocyclic moiety comprising 3-20 non-hydrogen atoms selected from the group consisting of O, N, S, P and C, wherein the first unsymmetrical cyanine monomer moiety is covalently attached to the linker; and the second unsymmetrical cyanine monomer moiety is covalently attached to the linker. In one aspect the first and the second unsymmetrical cyanine monomer moieties are the same, wherein the present compound is cyanine homodimer. In another aspect, the first and the second unsymmetrical cyanine monomer moieties are different, wherein the present compound is a cyanine heterodimer.

In an exemplary embodiment the kits employ a present nucleic acid reporter molecule is according to the formula:

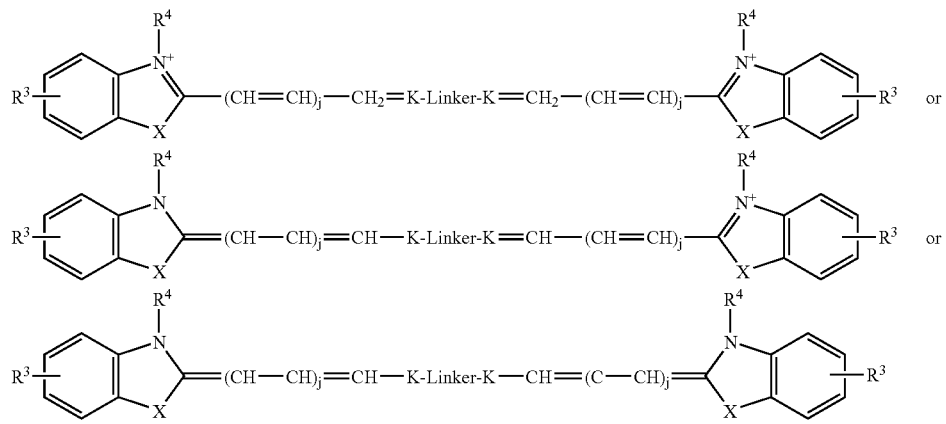

wherein each R[3] is independently hydrogen, unsubstituted $C_1$-$C_6$ alkyl substituted $C_1$-$C_6$ alkyl unsubstituted $C_1$-$C_6$ alkoxy, substituted $C_1$-$C_6$ alkoxy, unsubstituted fused benzene, substituted fused benzene, unsubstituted trifluoromethyl, substituted trifluoromethyl, unsubstituted halogen, substituted halogen, unsubstituted reactive group, substituted reactive group, unsubstituted carrier molecule, substituted carrier molecule, unsubstituted solid support or substituted solid support;

each R[4] is independently a unsubstituted $C_1$-$C_6$ alkyl substituted $C_1$-$C_6$ alkyl unsubstituted reactive group, substituted reactive group, unsubstituted carrier molecule, substituted carrier molecule, unsubstituted solid support or substituted solid support;

X is O, S, or CR[6]R[7] wherein each R[6] and R[7] are independently a unsubstituted $C_1$-$C_6$ alkyl substituted $C_1$-$C_6$ alkyl unsubstituted reactive group, substituted reactive group, unsubstituted carrier molecule, substituted carrier molecule, unsubstituted solid support, substituted solid support or R[6] and R[7] taken together form a 5- or 6-membered saturated ring;

j is 0, 1, or 2;

linker is a series of stable covalent bonds comprising 1-30 nonhydrogen atoms selected from the group consisting of C, N, O, S and P; and, K is substituted pyridinium, unsubstituted pyridinium, substituted quinolinium, or unsubstituted quinolinium.

Thus, in one embodiment, the unsymmetrical cyanine monomer is according to the formula:

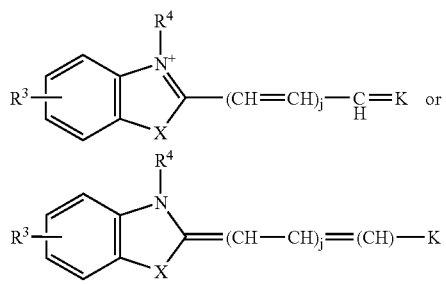

wherein the linker is covalently attached to the K moiety of the cyanine monomer.

Thus, in a particular embodiment, when the linker does not comprises at least one aromatic, heteroaromatic, cyclic or heterocyclic moiety, the kits use Compound 1, Compound 2, Compound 3, Compound 5, Compound 12, Compound 13, Compound 17, and Compound 22. These compounds are cell permeable and in a particularly useful embodiment Compound 1 is used to selectively detect mitochondrial DNA, See Example 43.

In another exemplary embodiment of the kits, a nucleic acid reporter molecule comprising a first unsymmetrical cyanine monomer moiety, a second unsymmetrical cyanine monomer moiety, and a linker having formula (I) —$(Y)_r$—$(CH_2)_m$-$T_q$-$(CH_2)_n$-E-$(CH_2)_n$-$T_q$-$(CH_2)_m$—$(Y)_r$— is employed. Y is a linear or branched moiety comprising 1-20 non-hydrogen atoms selected from the group consisting of C, N, O, P and S; T is a unsubstituted heteroatom or a substituted heteroatom; E is an aromatic, heteroaromatic, cyclic or heterocyclic moiety comprising 3-20 non-hydrogen atoms selected from the group consisting of O, N, S, P and C; r is independently 0 or 1; m is an integer of 0-6; n is independently 0 or 1; q is independently 0 or 1; and wherein the first unsymmetrical cyanine monomer moiety is covalently attached to the linker; and the second unsymmetrical cyanine monomer moiety is covalently attached to the linker.

In one aspect, E of the linker is

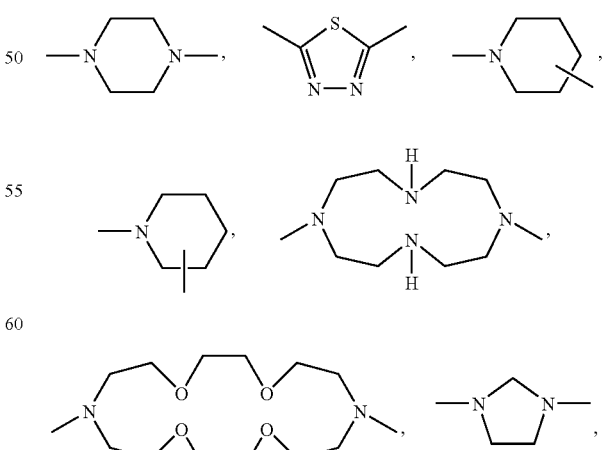

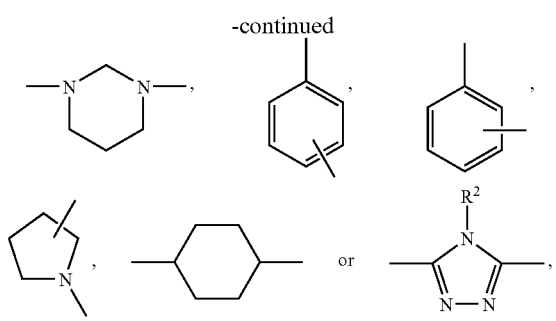

wherein R² is hydrogen, amine, substituted amine, substituted C₁-C₆ alkyl unsubstituted C₁-C₆ alkyl unsubstituted reactive group, substituted reactive group, unsubstituted carrier molecule, substituted carrier molecule, unsubstituted solid support, or substituted solid support. In a further aspect T of the linker, when present, is —NR², —N= or S wherein the R² is hydrogen, amine, substituted amine, substituted C₁-C₆ alkyl unsubstituted C₁-C₆ alkyl unsubstituted reactive group, substituted reactive group, unsubstituted carrier molecule, substituted carrier molecule, unsubstituted solid support, or substituted solid support.

In an exemplary embodiment, the nucleic aid reporter molecule of the present kits comprise a reactive group, solid support and carrier molecule wherein these substituents independently comprise a linker that is a single covalent bond, or a covalent linkage that is linear or branched, cyclic or heterocyclic, saturated or unsaturated, having 1-20 nonhydrogen atoms selected from the group consisting of C, N, P, O and S; and are composed of any combination of ether, thioether, amine, ester, carboxamide, sulfonamide, hydrazide bonds and aromatic or heteroaromatic bonds.

In an exemplary embodiment, the reactive group is selected from the group consisting of an acrylamide, an activated ester of a carboxylic acid, a carboxylic ester, an acyl azide, an acyl nitrile, an aldehyde, an alkyl halide, an anhydride, an aniline, an amine, an aryl halide, an azide, an aziridine, a boronate, a diazoalkane, a haloacetamide, a haloalkyl, a halotriazine, a hydrazine, an imido ester, an isocyanate, an isothiocyanate, a maleimide, a phosphoramidite, a reactive platinum complex, a silyl halide, a sulfonyl halide, a thiol and a photoactivatable group. In a further aspect, the reactive group is selected from the group consisting of carboxylic acid, succinimidyl ester of a carboxylic acid, hydrazide, amine and a maleimide.

In an exemplary embodiment the carrier molecule is selected from the group consisting of an amino acid, a peptide, a protein, a polysaccharide, a nucleoside, a nucleotide, an oligonucleotide, a nucleic acid polymer, a hapten, a psoralen, a drug, a hormone, a lipid, a lipid assembly, a synthetic polymer, a polymeric microparticle, a biological cell or a virus. In a further aspect, the carrier molecule is selected from the group consisting of an antibody or fragment thereof, an avidin or streptavidin, a biotin, a blood component protein, a dextran, an enzyme, an enzyme inhibitor, a hormone, an IgG binding protein, a fluorescent protein, a growth factor, a lectin, a lipopolysaccharide, a microorganism, a metal binding protein, a metal chelating moiety, a non-biological microparticle, a peptide toxin, a phosphotidylserine-binding protein, a structural protein, a small-molecule drug, or a tyramide.

In an exemplary embodiment, the solid support is selected from the group consisting of a microfluidic chip, a silicon chip, a microscope slide, a microplate well, silica gels, polymeric membranes, particles, derivatized plastic films, glass beads, cotton, plastic beads, alumina gels, polysaccharides, polyvinylchloride, polypropylene, polyethylene, nylon, latex bead, magnetic bead, paramagnetic bead, and superparamagnetic bead. In a further aspect, the solid support is selected from the group consisting of Sepharose, poly(acrylate), polystyrene, poly(acrylamide), polyol, agarose, agar, cellulose, dextran, starch, FICOLL, heparin, glycogen, amylopectin, mannan, inulin, nitrocellulose, diazocellulose and starch.

In an exemplary embodiment of the present kits, the linker of the nucleic acid reporter molecule is

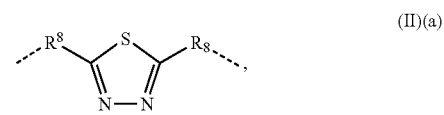  (II)(a)

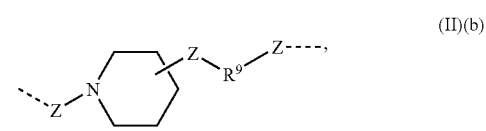  (II)(b)

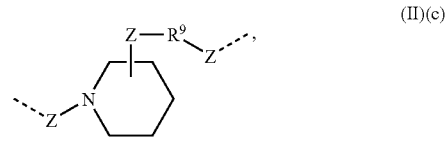  (II)(c)

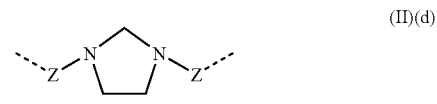  (II)(d)

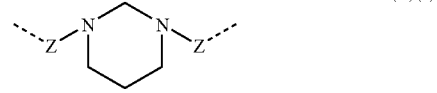  (II)(e)

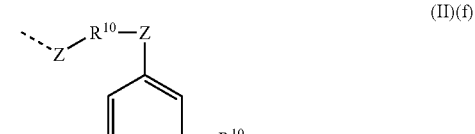  (II)(f)

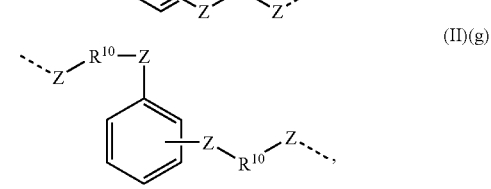  (II)(g)

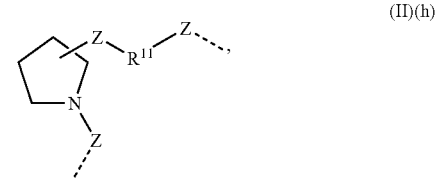  (II)(h)

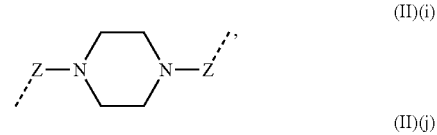  (II)(i)

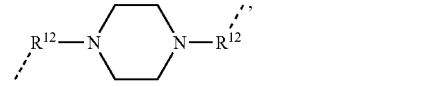  (II)(j)

-continued

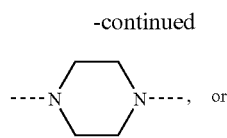
(II)(ia)

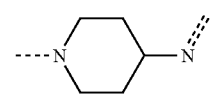
(II)(ib)

Wherein each $R^8$, $R^9$, $R^{10}$, $R^{11}$ and $R^{12}$ are independently a —$NR^2$, —N= or S wherein $R^2$ is hydrogen, amine, substituted amine, substituted $C_1$-$C_6$ alkyl unsubstituted $C_1$-$C_6$ alkyl unsubstituted reactive group, substituted reactive group, unsubstituted carrier molecule, substituted carrier molecule, unsubstituted solid support, or substituted solid support; each Z is independently —$(CH_2)_g$— wherein g is 0 or 1, wherein the dashed line is attached directly to the K moiety of the unsymmetrical cyanine monomer. In one aspect $R^8$ is S. In a further aspect, $R^{12}$ is —NH or —N=.

Particularly preferred for the detection of nucleic acid is reporter molecules wherein the linker

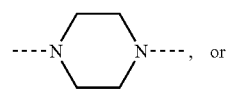
(II)(ia)

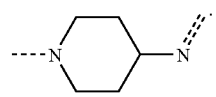
(II)(ib)

In a particularly preferred embodiment, the nucleic acid reporter molecules are employed to detect RNA in the presence of DNA wherein the nucleic acid reporter molecule has a RNA/DNA ratio of fluorescence enhancement greater than about one. In this instance the nucleic acid reporter molecule comprises a first monomethine unsymmetrical cyanine monomer moiety, a second monomethine unsymmetrical cyanine monomer moiety and a linker that is

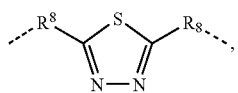
(II)(a)

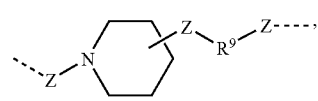
(II)(b)

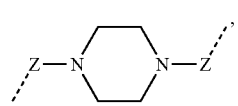
(II)(i)

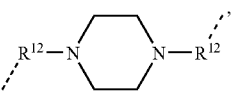
(II)(j)

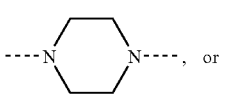
(II)(ia)

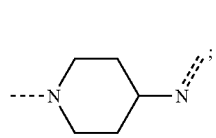
(II)(ib)

wherein $R^8$ is a substituted heteroatom or an unsubstituted heteroatom; $R^9$ is a substituted heteroatom or an unsubstituted heteroatom; $R^{12}$ is a substituted heteroatom or an unsubstituted heteroatom; each Z is —$(CH_2)_g$ wherein g is 0 or 1; and the first unsymmetrical cyanine monomer moiety is covalently attached to the linker; and the second unsymmetrical cyanine monomer moiety is covalently attached to the linker. In a further embodiment, $R^8R^9$ and $R^{12}$ are —$NR^2$, —N= or S wherein $R^2$ is hydrogen, amine, substituted amine, substituted $C_1$-$C_6$ alkyl, unsubstituted $C_1$-$C_6$ alkyl, unsubstituted reactive group, substituted reactive group, unsubstituted carrier molecule, substituted carrier molecule, unsubstituted solid support, or substituted solid support. In an exemplary embodiment, Compound 6 is preferred for the detection of intracellular RNA.

In an exemplary embodiment, the monomethine unsymmetrical cyanine monomer moiety has the general formula:

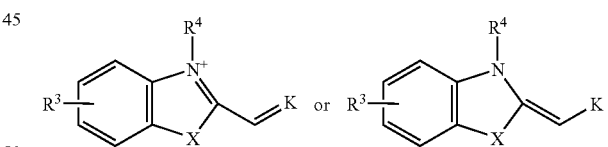

wherein $R^3$, R4, X and K are as defined above. A detailed description of the invention having been provided above, the following examples are given for the purpose of illustrating the invention and shall not be construed as being a limitation on the scope of the invention or claims.

EXAMPLES

Example 1

Preparation of Compound 1

To 52 mg of 2-chloro-4-(2,3-dihydro-3-methyl-(benzo-1,3-thiazol-2-yl)-methylidene-1-phenylquinolinium iodide in 5 mL of methylene chloride, 19 mg of 1,9-nonanedithiol is added followed by 20 μL of triethylamine. The mixture is stirred at room temperature overnight and 3.5 mL of ethyl acetate is then added to precipitate out Compound 1.

Compound 1

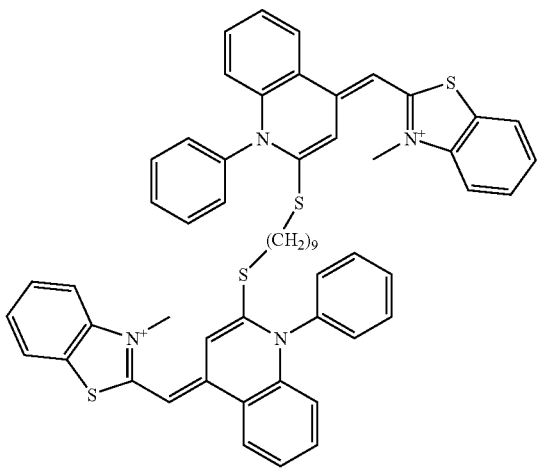

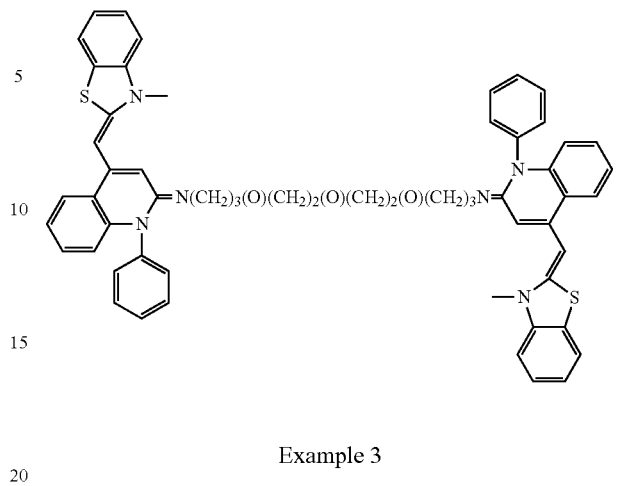

Example 3

Preparation of Compound 3

A mixture of 26 mg 2-(3-succinimidyloxycarbonylethylthio)-4-(2,3-dihydro-3-methyl-(benzo-1,3-thiazol-2-yl)-methylidene-1-phenylquinolinium iodide, 2.7 mg of 3,3'-diamino-n-methyldipropylamine, and 7 μL of triethylamine is stirred in 1 mL of DMF at room temperature for 30 minutes. At the end of the period, 2 mL of ethyl acetate is added to precipitate Compound 3.

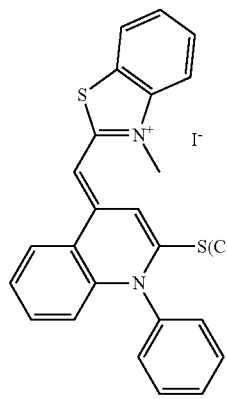

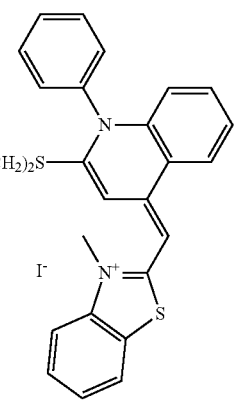

Example 2

Preparation of Compound 2

A mixture of 150 mg of 2-chloro-4-(2,3-dihydro-3-methyl-(benzo-1,3-thiazol-2-yl)-methylidene-1-phenylquinolinium chloride, 32 mg of 4,7,10-trioxa-1,13-tridecanediamine, and 48 μL of triethylamine is heated in 10 mL of dichloroethane at 40-50 C for 4 hours. The solvent is evaporated and the residue is dissolved in 2 mL of DMF and added to 0.43 g of sodium iodide in 10 mL of water. Compound 2 is collected by filtration.

Example 4

Preparation of Compound 4

A mixture of 27 mg of 2-(3-succinimidyloxycarbonylethylthio)-4-(2,3-dihydro-3-methyl-(benzo-1,3-thiazol-2-yl)-methylidene-1-phenylquinolinium iodide, 3.9 mg of 1,4-bis(3-aminopropyl)piperazine and 7 μL of triethylamine is stirred at room temperature for 30 minutes and 2 mL of ethyl acetate is then added to precipitate out Compound 4.

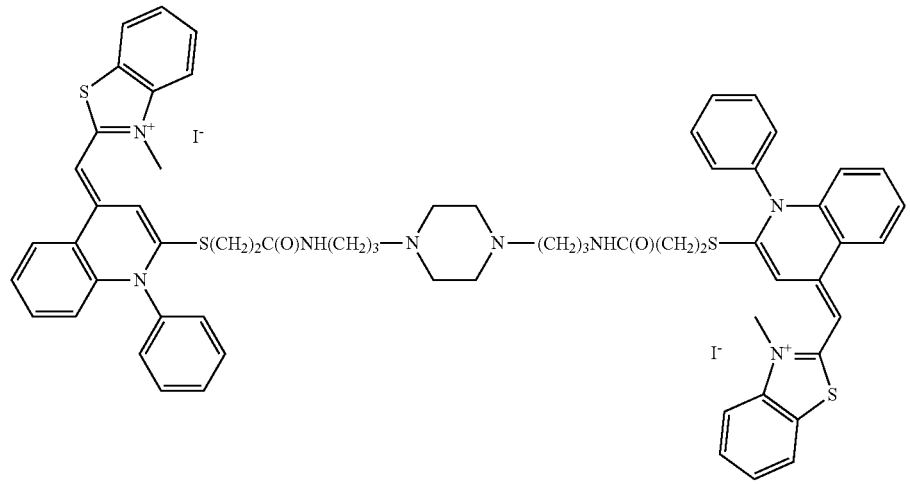

Example 5

Preparation of Compound 5

A mixture of 59 mg of 2-chloro-4-(2,3-dihydro-3-methyl-(benzo-1,3-thiazol-2-yl)-methylidene-1-phenylquinolinium iodide, 12 mg of N,N'-bis(2-mercaptoethyl)succinamide, and 17 μL of triethylamine is stirred at room temperature for 30 minutes and Compound 5 is collected by filtration.

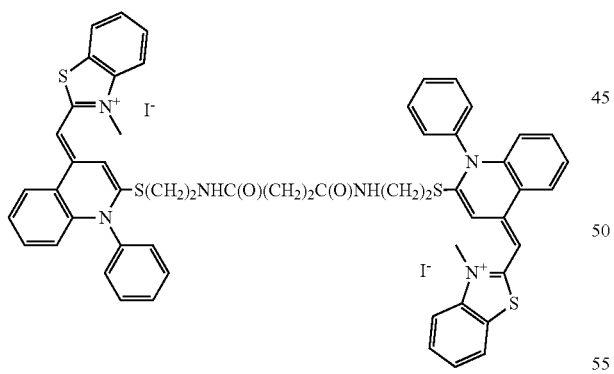

Compound 5

Example 6

Preparation of Compound 6

A mixture of 537 mg of 2-chloro-4-(2,3-dihydro-3-methyl-(benzo-1,3-thiazol-2-yl)-methylidene-1-phenylquinolinium chloride, 40 mg of piperazine, and 0.13 mL of triethylamine is heated in 10 mL of dichloroethane at 60 C for 4 hours. Compound 6 is collected by filtration.

Compound 6

Example 7

Preparation of Compound 7

A mixture of 300 mg of 2-chloro-4-(2,3-dihydro-3-methyl-(benzo-1,3-thiazol-2-yl)-methylidene-1-phenylquinolinium chloride, 35 mg of dimercapto-1,3,4-thiadiazole, and 0.2 mL of triethylamine is stirred in 10 mL of dichloroethane overnight and Compound 7 is collected by filtration.

Compound 7

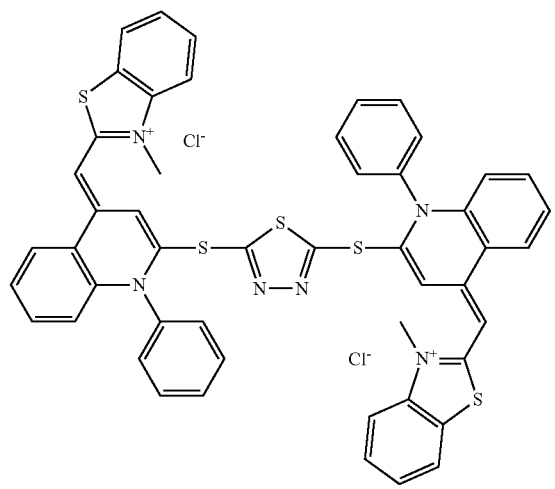

Example 8

Preparation of Compound 8

A mixture of 300 mg of 2-chloro-4-(2,3-dihydro-3-methyl-(benzo-1,3-thiazol-2-yl)-methylidene-1-phenylquinolinium chloride, 26 mg of trans-1,4-diaminocyclohexane, and 0.2 mL of triethylamine is heated in 10 mL of dichloroethane at 60 C overnight and Compound 8 is collected by filtration.

Compound 8

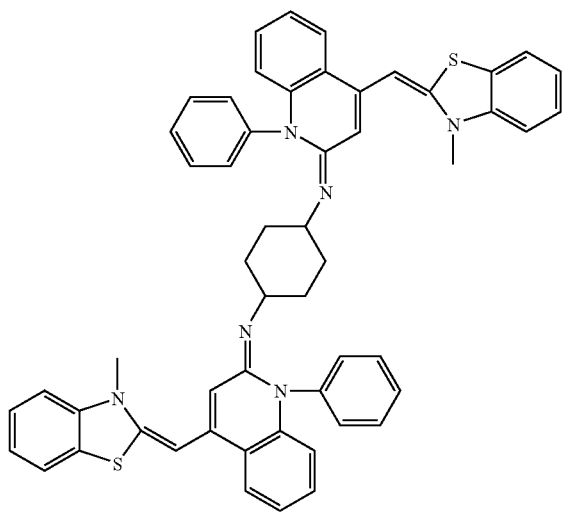

Example 9

Preparation of Compound 9

A mixture of 123 mg of 2-chloro-4-(2,3-dihydro-3-methyl-(benzo-1,3-thiazol-2-yl)-methylidene-1-phenylquinolinium chloride, 11 mg of 1,4-diaminopiperazine, and 0.12 mL of triethylamine is heated in 3 mL of DMF at 60 C for 5 hours and Compound 9 is collected by filtration.

Compound 9

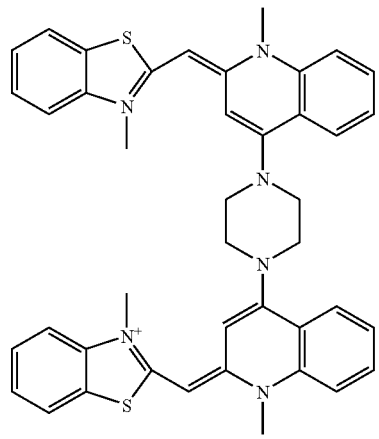

Example 10

Preparation of Compound 10

A mixture of 282 mg of 4-chloro-2-(2,3-dihydro-3-methyl-(benzo-1,3-thiazol-2-yl)-methylidene-1-phenylquinolinium chloride, 25 mg of 1,4-diaminopiperazine, and 0.25 mL of triethylamine is heated in 15 mL of DMF at 60 C for 2 hours and Compound 10 is collected by filtration.

Compound 10

Example 11

Preparation of Compound 11

A mixture of 90 mg of 2-chloro-4-(2,3-dihydro-3-methyl-(benzo-1,3-thiazol-2-yl)-methylidene-1-phenylpyridinium chloride, 9 mg of piperazine, and 0.035 mL of triethylamine is heated in 5 mL of DMF at 60 C for 2 hours and 15 mL of ethyl acetate is added and Compound 11 is collected by filtration.

Compound 11

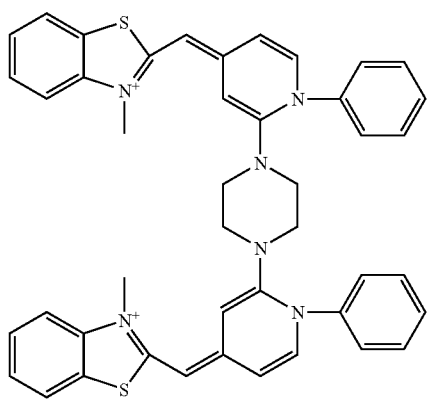

Example 12

Preparation of Compound 12

A mixture of 0.2 g of 1,10-bis(4-methyl-quninolon-1-yl) decane, 0.8 mL of trimethylsilyltrifluoromethanesulfonate, 0.61 g of diisopropylethylamine and 0.35 g of 3-methyl-2-methylthio-benzothiazolium tosylate is heated in 5 mL of methylene chloride overnight. To the reaction mixture, 10 mL of water is added and filtered and dried in vacuo. The solid is heated in 10 mL of dichloroethane with 0.25 mL of phosphorous oxychloride for 7 hours to obtain Compound 12.

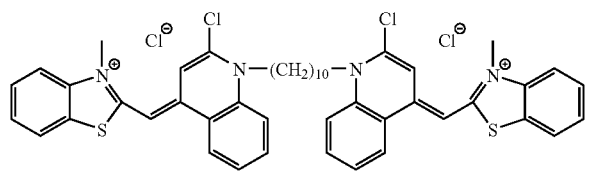

Example 13

Preparation of Compound 13

A mixture of 73 mg of Compound 12 and 76 µL of 3,3'-iminobis(N,N-dimethylpropylamine) is heated in 1 mL of DMF at 60 C for 2 hours. The reaction mixture is then added to a basic sodium iodide solution (0.25 g of NaI and 0.5 mL of a 10% NaOH in 10 mL of water). The solid is filtered and dried and heated with 1 mL of iodomethane in 1.5 mL of DMF at 60 C for 2 hours to obtain Compound 13.

Compound 13

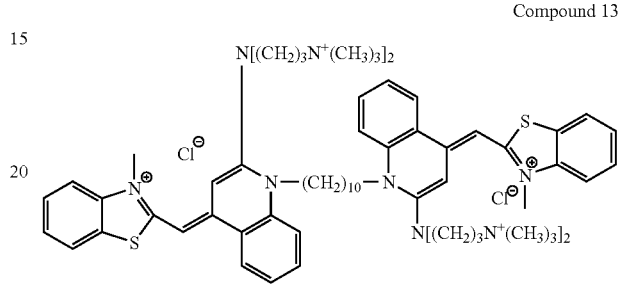

Example 14

Preparation of Compound 14

To 848 mg of 1,4-bis(4-bromobenzyl)piperazine in 60 mL of THF at −78 C under nitrogen, 2.5 mL of a 1.6M n-butyllithium is introduced followed by 0.865 g of 1,4-dimethyl-2-quinolone in 20 mL of THF. After one hour of stirring at the low temperature, 2 mL of acetic acid is added and stirred at room temperature overnight. All volatile components are removed under reduced pressure and the residue is resuspended in 50 mL of methylene chloride and 2.8 g of 3-methyl-2-methylthiobenoxazolium tosylate and 2 mL of triethylamine is added. The reaction mixture is stirred at room temperature for 15 minutes and Compound 14 is purified on a silica gel column.

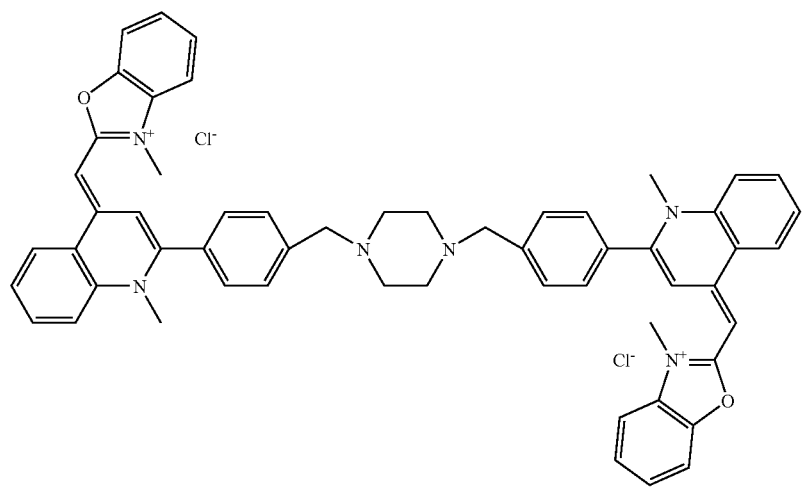

Example 15

Preparation of Compound 15

A mixture of 0.55 g of 2-chloro-4-(2,3-dihydro-3-methyl-(benzo-1,3-thiazol-2-yl)-methylidene-1-phenylquinolinium chloride, 43 mg of cylcen and 0.2 mL of triethylamine is heated at 60 C for three days to obtain Compound 15.

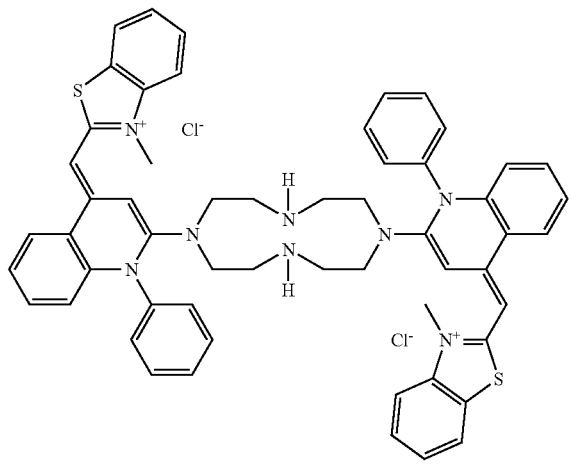

Example 16

Preparation of Compound 16

A mixture of 0.34 g of 2-chloro-4-(2,3-dihydro-3-methyl-(benzo-1,3-thiazol-2-yl)-methylidene-1-phenylquinolinium chloride, 68 mg of 1,4,10,13-tetraoxa-7,16-diaza-cyclooctadecane, and 0.11 mL of triethylamine is heated in 10 mL of DMF at 60 C overnight. The crude is precipitated out by the addition of ethyl acetate and purified on a silica gel column to obtain Compound 16.

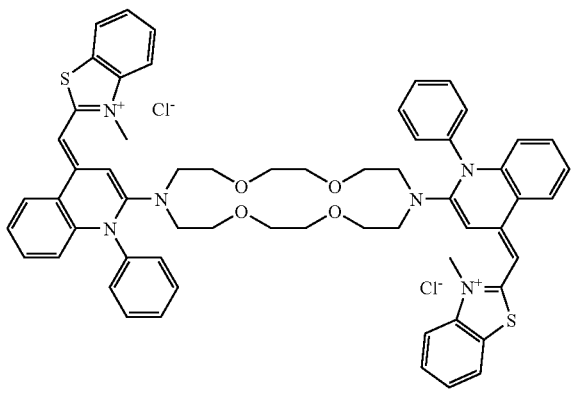

Example 17

Preparation of Compound 17

A mixture of 0.6 g of 2-chloro-4-(2,3-dihydro-3-methyl-(benzo-1,3-thiazol-2-yl)-methylidene-1-phenylquinolinium chloride, 18 mg of N,N'-dimethylhydrazine, and 0.35 mL of triethylamine is heated at 80 C for 9 hours. The reaction mixture is then added to 50 mL of a 1:1 mixture of brine and water and filtered to obtain the crude, which is then purified by recrystallization from DMF and ethyl acetate to obtain Compound 17.

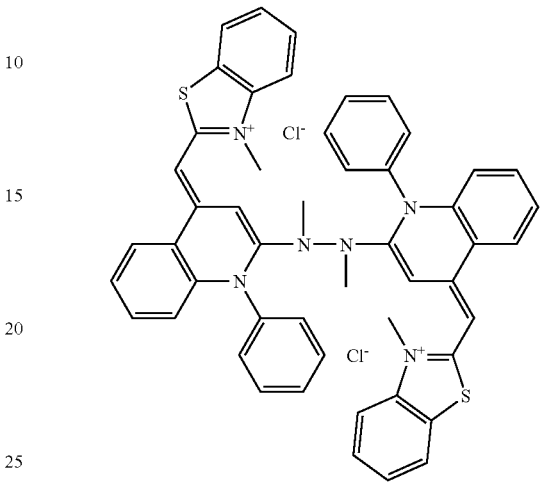

Example 18

Preparation of Compound 18

A mixture of 0.16 g of 2-chloro-4-(2,3-dihydro-3-methyl-(benzo-1,3-thiazol-2-yl)-propylidene-1-phenylpyridinium chloride, 10 mg of piperazine and 35 μL of triethylamine in 5 mL of DMF at 60 C overnight. The crude is then purified on a silica gel column to obtain Compound 18.

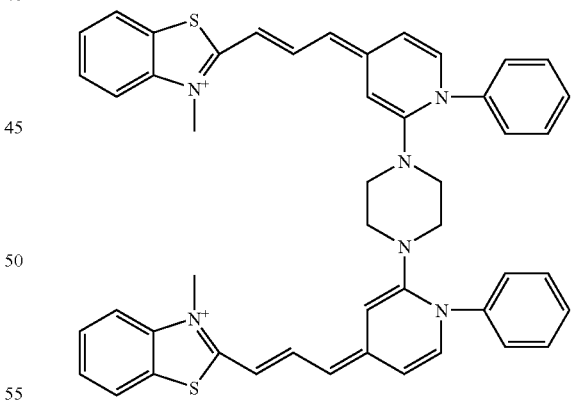

Example 19

Preparation of Compound 19

A mixture of 0.1 g of 2-chloro-4-(2,3-dihydro-3-methyl-(benzo-1,3-thiazol-2-yl)-methylidene-7-methyoxy-1-phenylquinolinium iodide, 5 mg of piperazine, and 25 μL of triethylamine is heated in 5 mL of DMF at 60 C for 2 hours and filtered to obtain Compound 19.

Compound 19

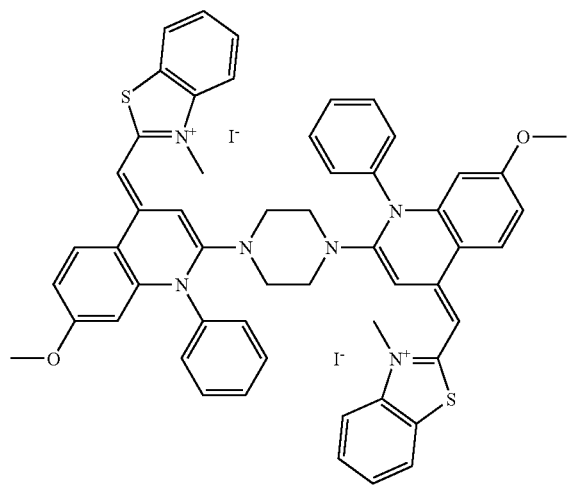

Compound 21

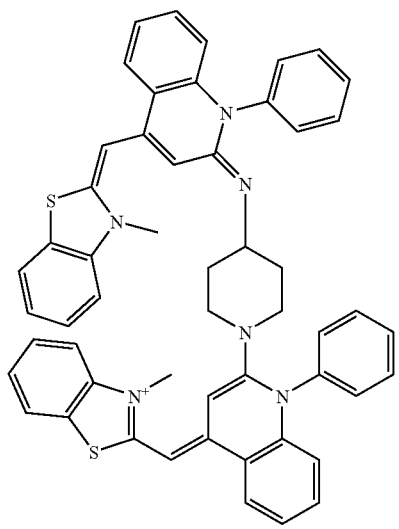

Example 20

Preparation of Compound 20

A mixture of 0.16 g of 2-chloro-4-(2,3-dihydro-3-methyl-(benz-1,3-oxazol-2-yl)-methylidene-1-phenylquinolinium chloride, 7.3 mg of piperazine, and 33 μL of triethylamine is heated in 3 mL of DMF at 60 C for 7 hours and filtered to obtain Compound 20.

Example 22

Preparation of Compound 22

A mixture of 0.1 g of 2-chloro-4-(2,3-dihydro-3-methyl-(benz-1,3-oxazol-2-yl)-methylidene-1-phenylpyridinium chloride, 25 mg of 1,9-nonanedithiol, and 36 μL of triethylamine is stirred in 5 mL of DMF at room temperature overnight to obtain Compound 22.

Compound 20

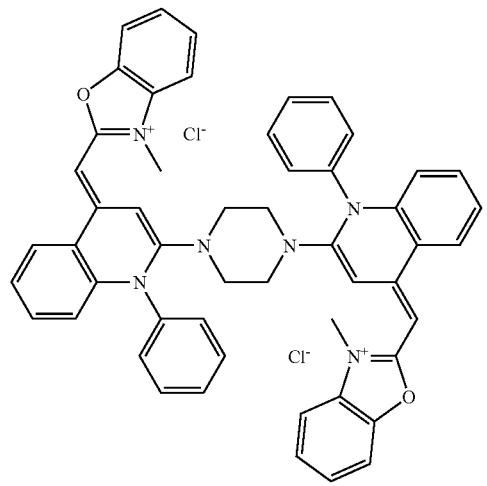

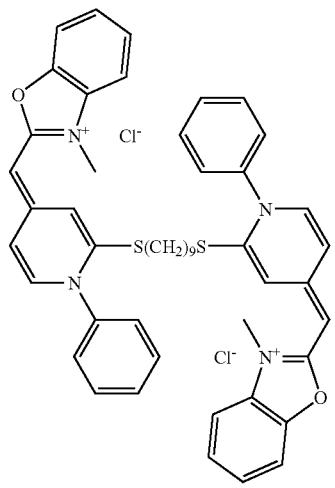

Example 21

Preparation of Compound 21

A mixture of 0.1 g of 2-chloro-4-(2,3-dihydro-3-methyl-(benzo-1,3-thiazol-2-yl)-propylidene-1-phenylpyridinium chloride, 10 mg of 4-aminopiperidine, and 70 μL of triethylamine is heated in 5 mL of dichloroethane at 60 C overnight to obtain Compound 21.

Example 23

Preparation of Compound 23

A mixture of 0.1 g of 2-chloro-4-(2,3-dihydro-3-methyl-(benzo-1,3-thiazol-2-yl)-methylidene-1-phenylpyridinium chloride, 9 mg of piperazine, and 0.1 mL of triethylamine is heated in 5 mL of dichloroethane at reflux overnight. The reaction mixture is filtered to obtain Compound 23.

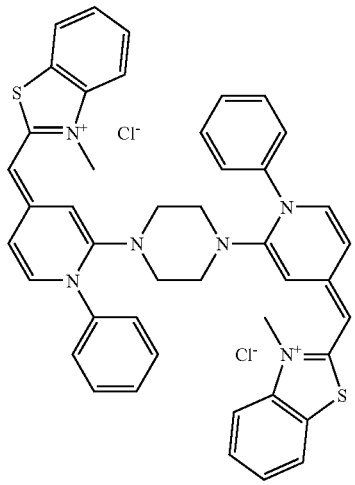

Example 24

Preparation of Compound 24

A mixture of 2-chloro-4-(2,3-dihydro-3-methyl-(benzo-1,3-thiazol-2-yl)-methylidene-1-phenylquinolinium chloride, 0.5 equivalent of 1,3-benzenedithiol and 2 equivalents of triethylamine is stirred at room temperature in methylene chloride to obtain the product.

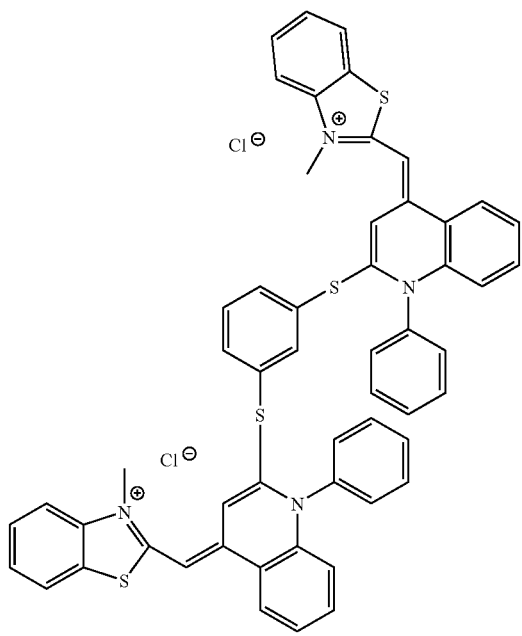

Example 25

Preparation of Compound 25

A mixture of 118 mg of 2-chloro-4-(2,3-dihydro-3-methyl-(benzo-1,3-thiazol-2-yl)-methylidene-1-phenylquinolinium chloride, 786 mg of 1,4-diaminopiperazine, and 1.1 mL of triethylamine is heated in 10 mL of dichloroethane at 60 C for 24 hours. The intermediate is recovered from filtration and after purification is heated with 1.2 equivalents of 2-chloro-4-(2,3-dihydro-3-methyl-(benzo-1,3-thiazol-2-yl)-methylidene-1-phenylpyridinium chloride and 3 equivalents of triethylamine in DMF at 60 C for 6 h. Compound 25 is then obtained by filtration.

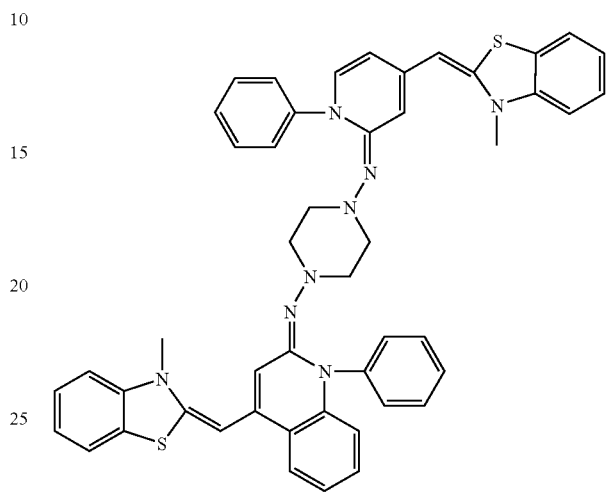

Example 26

Preparation of Compound 29

A mixture of 2-chloro-4-(2,3-dihydro-3-methyl-(benzo-1,3-thiazol-2-yl)-methylidene-1-phenylquinolinium chloride, 0.5 equivalent of 4-aminomethylpiperidine and 2 equivalents of triethylamine is heated in DMF at 60 C to yield the product.

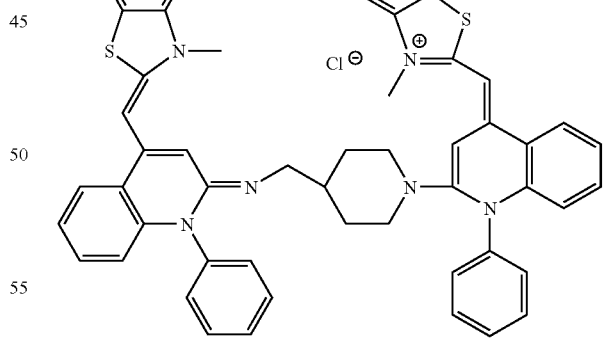

Example 27

Preparation of Compound 30

A mixture of 2-chloro-4-(2,3-dihydro-3-methyl-(benzo-1,3-thiazol-2-yl)-methylidene-1-phenylquinolinium chloride, 0.5 equivalent of 3-aminopyrrolidine dihydrochloride and 4 equivalent of triethylamine is heated in DMF at 60 C to yield the product.

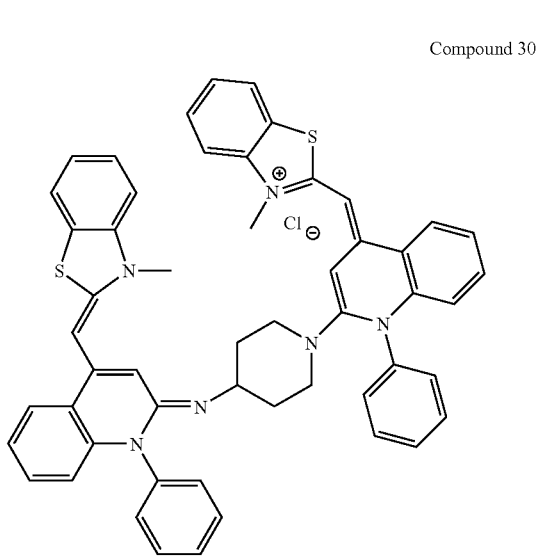

Compound 30

Example 28

Preparation of Compound 31

A mixture of 3-(5-carboxypentyl)-2-methylthio-benzothiazolium bromide and one equivalent of 2-chloro-4-methyl-1-phenylquinolinium chloride and two equivalents of triethylamine is stirred in DMF at room temperature to yield the product.

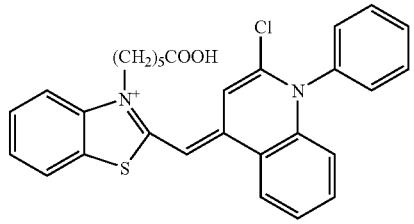

Example 29

Preparation of Compound 32

A mixture of 2-chloro-4-(2,3-dihydro-3-(5-carboxypentyl)-(benzo-1,3-thiazol-2-yl)-methylidene-1-phenylquinolinium chloride (Compound 31), 0.5 equivalent of piperazine and 6 equivalents of triethylamine is heated in DMF at 60 C and the diacid isolated is converted to the corresponding bis succinimidyl ester with O-(N-succinimidyl)-N,N,N',N'-tetramethyluronium tetrafluoroborate and triethylamine in DMF.

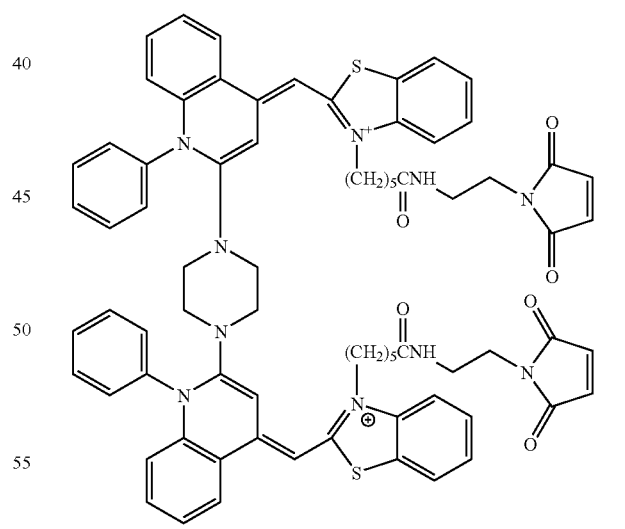

Compound 32

Example 30

Preparation of Compound 33

The compound is prepared by treating Compound 32 with 2 equivalent of N-2(aminoethyl)maleimide trifluoroacetic acid salt in the presence of 5 equivalents of triethylamine in DMF at room temperature.

Compound 33

Example 31

Preparation of Compound 34

The compound is prepared by treating Compound 32 with 10 equivalents of hydrazine at room temperature in DMF.

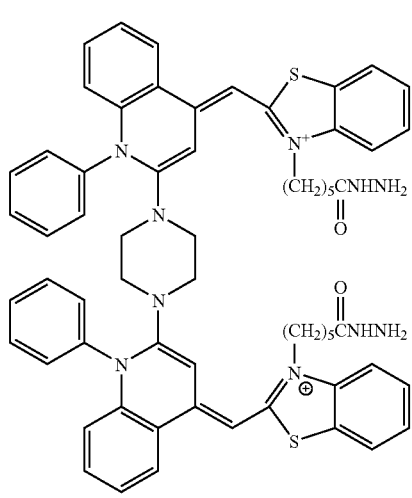

Compound 34

Example 32

Preparation of Compound 35

A mixture of 2-chloro-4-(2,3-dihydro-3-methyl-(benzo-1,3-thiazol-2-yl)-methylidene-1-phenylquinolinium chloride, 0.5 equivalent of 4-amino-4H-1,2,4-triazole-3,5-dithiol and 3 equivalent of triethylamine is stirred in methylene chloride at room temperature to yield the product.

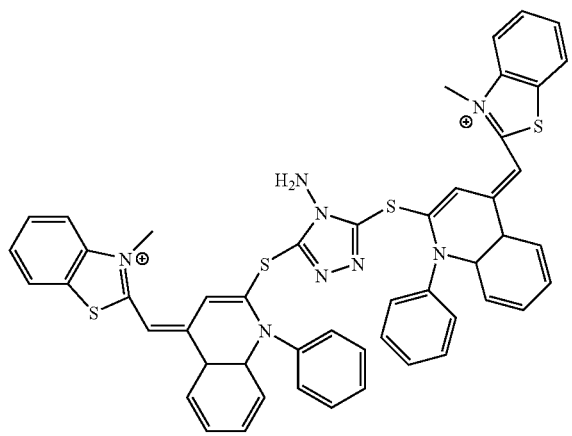

Example 33

Preparation of Compound 36

A mixture of Compound 35 and 1.5 equivalent of succinic anhydride is heated in DMF at about 50 C to generate the target carboxylic acid which is converted to the corresponding succinimidyl ester with O-(N-succinimidyl)-N,N,N',N'-tetramethyluronium tetrifluoroborate and triethylamine in DMF.

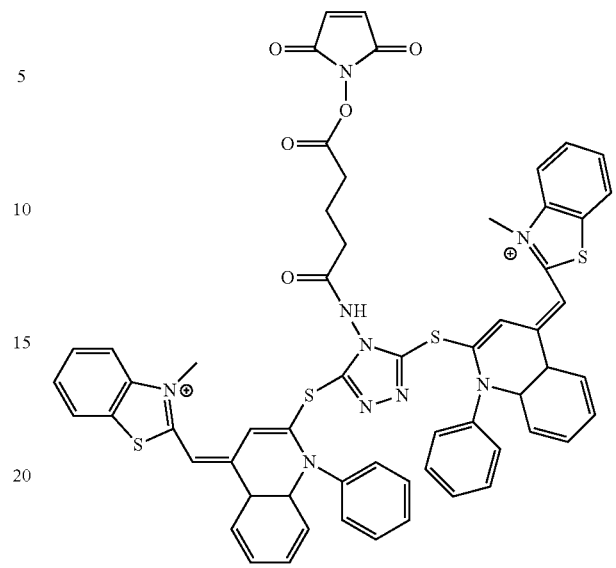

Example 34

Preparation of Compound 37

The compound is prepared by treating Compound 36 with 2 equivalent of N-2(aminoethyl)maleimide trifluoroacetic acid salt in the presence of 5 equivalents of triethylamine in DMF at room temperature.

Example 35

Figure 1B:
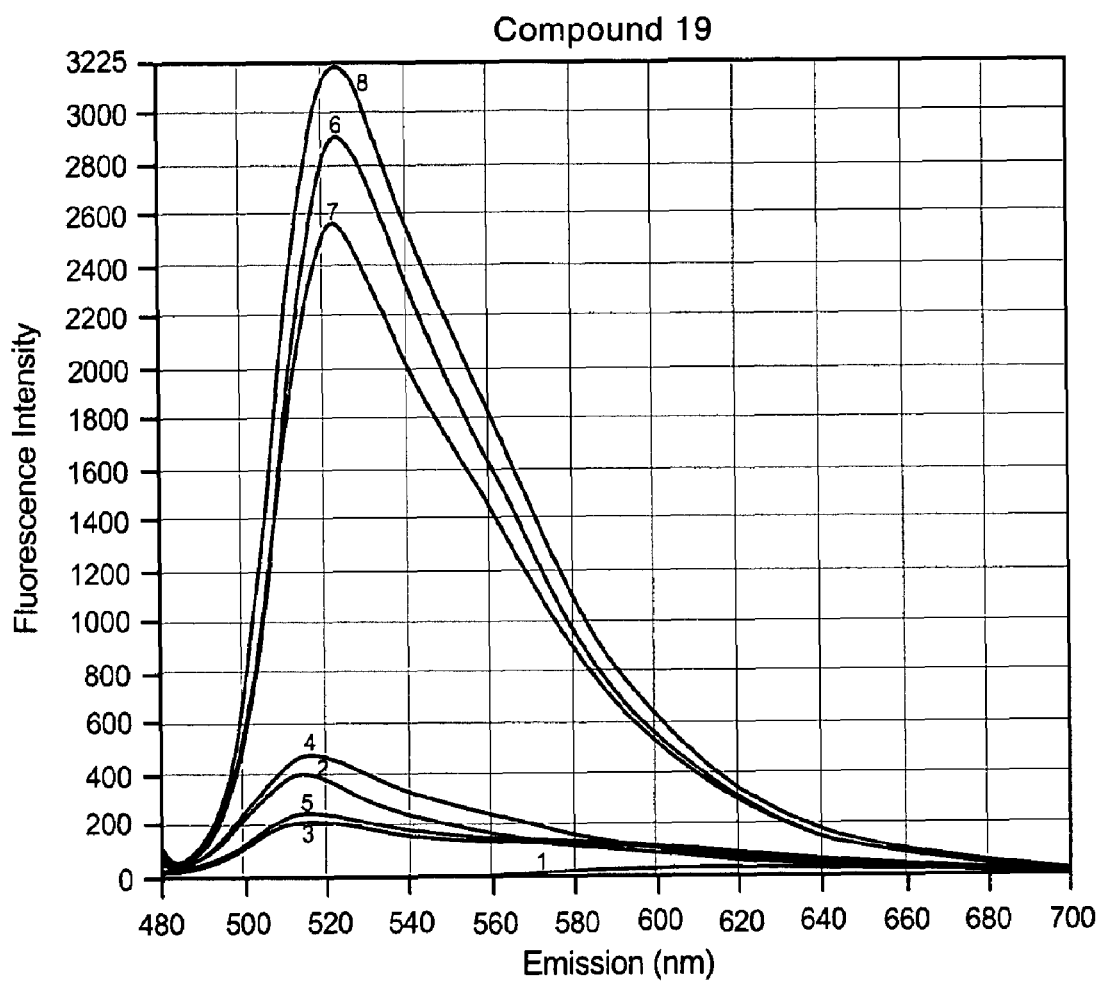

Emission Spectra of Compound 6 and Compound 19 Binding to RNA and DNA Demonstrating a Fluorescent Signal Intensity that is Greater for RNA than DNA A stock solution of Compound 6 and Compound 19 was made by dissolving an unknown mass of each reporter molecule individually in 1 mL of DMSO. The stock solution was then diluted 1/1261 in 10 mM TRIS, 1 mM EDTA (pH 7.2). This dilute solution resulted in an OD at ~0.05-0.1 and extinction coefficient set at 45,000 yielding a working concentration of ~1-2 µM. Compound 6 and Compound 19, each at about 1-2 µM, were added to the test samples (1) Buffer only; 2) DNA calf thymus; 3) DNA Type XI, *Micrococcus lysodeikticus;* 4) DNA Type XII *Clostridium perfringens;* 5) DNA Type VIII, *E. coli* strain B; 6) RNA, ribosomal; 7) RNA Type III, Baker's yeast and 8) RNA Type XX, *E. coli* strain W). The RNA and DNA were present at a final concentration of about 60 µg/mL. After addition of the dye and the nucleic acid the samples were excited at 470 nm and emission read. See, FIG. 1.

This example provides a methodology for testing compounds within the scope of the invention for their ability to fluoresce when complexed with RNA or DNA. In addition, this methodology provides a method for screening compounds wherein a particular intensity is desired or compounds that are selective for RNA and/or DNA, showing a greater signal intensity for one form of nucleic acid in the presence of another form.

Example 36

Comparison of in solution binding of Compound 11 to RNA, DNA and RNA+DNA

Figure 2A:
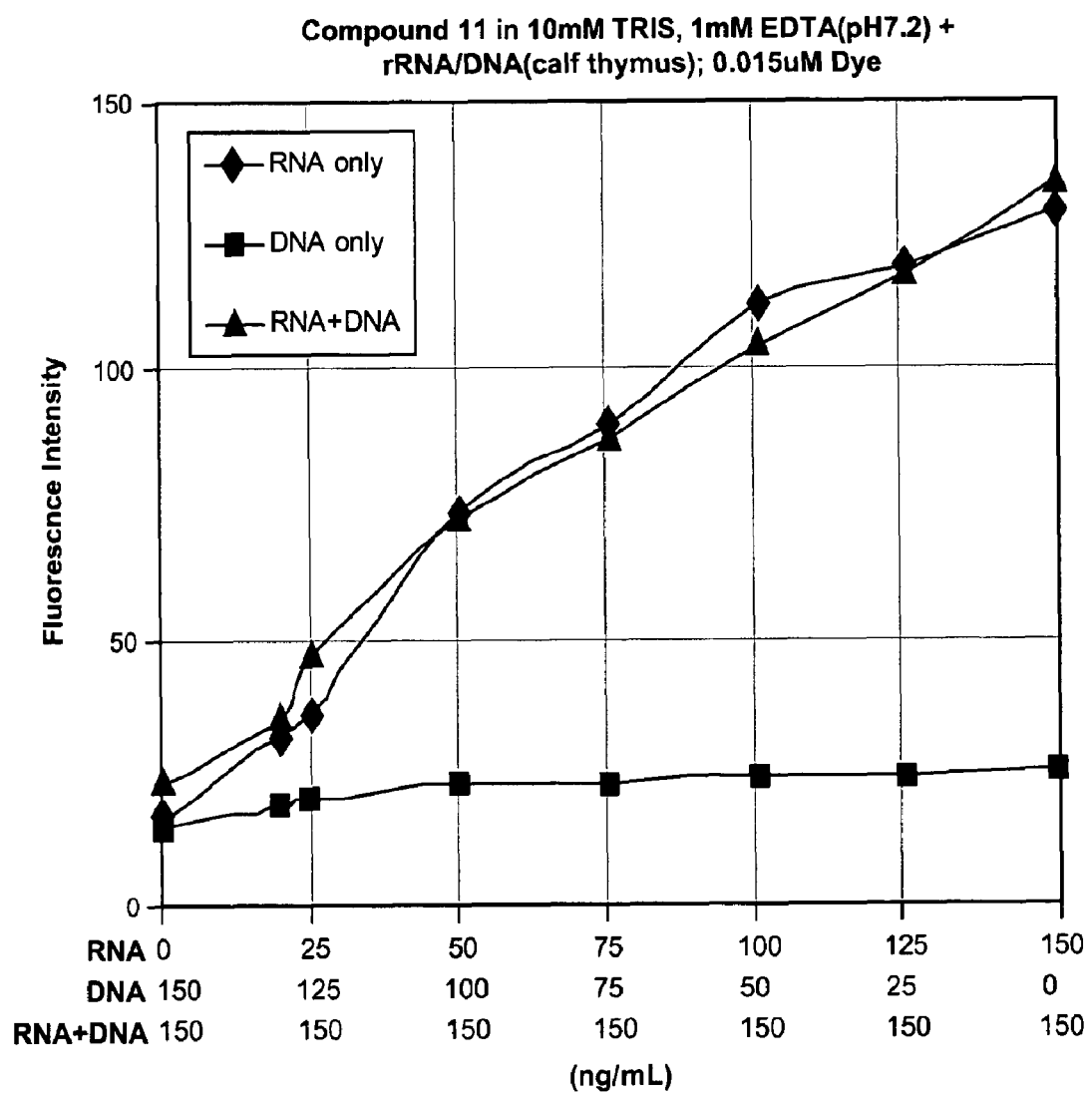
FIG. 2: Shows the intensity of the fluorescent signal from Compound 11 at 0.015 µM when bound to different concentrations of calf thymus (2A), *Micrococcus lysodeikticus* (2B), *Clostridium perfringens* (2C) rRNA, DNA and RNA+DNA in solution.
Figure 2B:
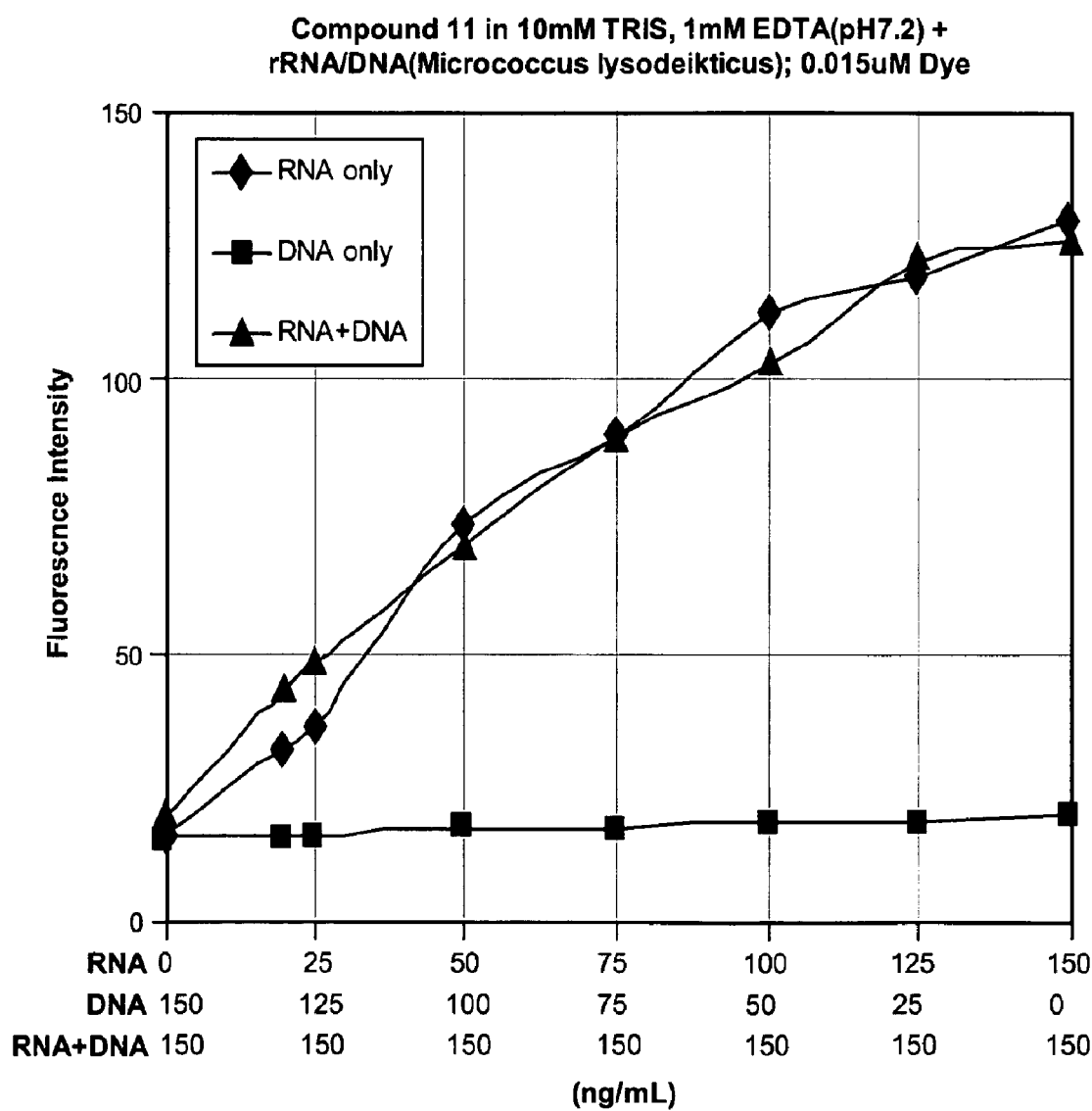
Figure 2C:
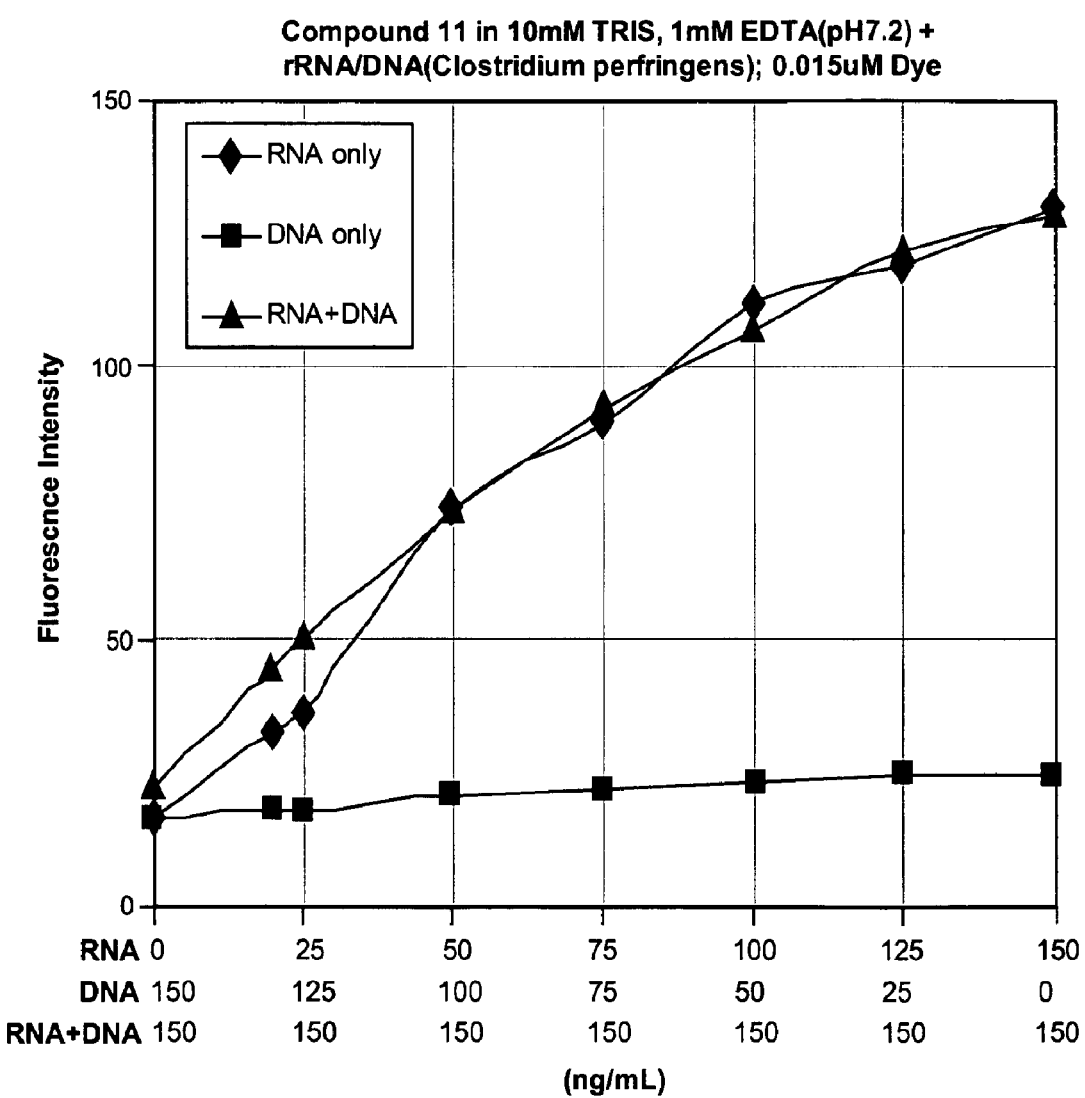

A buffer solution of 200 ul of 10 mM TRIS, 1 mM EDTA (pH7.2) was added to the wells of a 96-well microplate. RNA and DNA (calf thymus, *Micrococcus lysodeikticus* and *Clostridium perfringens*) dilutions in TE (pH7.2) were added to the appropriate wells to yield the final concentrations of 0-150 ng/mL. In separate wells RNA and DNA were combined for a final concentration of 150 ng/mL of nucleic acid wherein the concentrations were combined in the following format: RNA+DNA respectively, 0 ng/mL+150 ng/mL, 25 ng/mL+125 ng/mL, 50 ng/mL+100 ng/mL, 75 ng/mL+75 ng/mL, 100 ng/mL+50 ng/mL, 125 ng/mL+25 ng/mL and 150 ng/mL+0 ng/mL. Compound 11, from a stock solution in DMSO, was added to the microplate wells at a final concentration of 0.015 µM. The wells were read at 460 nm/500 nm Ex/Em. Compound 11 demonstrated an increased fluorescent intensity signal with increasing concentrations of RNA but little to no signal when combined with DNA alone. These results were confirmed wherein the combined RNA+DNA resulted in the same signal intensity for the corresponding concentration of RNA. See, FIG. 2.

Using this or similar methodology, a variety of compounds as described herein may be screened for their fluorescence properties when associated with nucleic acids. Similarly, compounds may be screened based upon their relative fluorescence enhancement when associated with RNA versus DNA, or alternatively for their relative fluorescence enhancement when associated with DNA in the presence of RNA. Compounds can be readily screened for a particular desired intensity, wavelength, or selectivity for RNA and/or DNA. See, Table 3

TABLE 3

| Compound | Excitation/Emission (nm)[1] | Fluorescence Enhancement Ratio (RNA/DNA)[2] |
|---|---|---|
| 1 | M | 1.0 |
| 6 | M | 7.0 |
| 7 | M | 2.3 |
| 8 | M | 4.9 |
| 9 | M | 1.7 |
| 11 | M | 12 |

TABLE 3-continued

| Compound | Excitation/Emission (nm)[1] | |
|---|---|---|
| 13 | M | 2.5 |
| 18 | 570/620 | 1.3 |
| 19 | M | 4.9 |
| 20 | M | 8.5 |
| 25 | M | 5.6 |
| | | Fluorescence Enhancement Ratio (DNA/RNA)[3] |
| 15 | M | 3.7 |

[1]Complex with nucleic acid
[2]The ratio of the fluorescence enhancement of the compound when associated with RNA to the fluorescence enhancement of the compound when associated with DNA.
[3]The ratio of the fluorescence enhancement of the compound when associated with DNA to the fluorescence enhancement of the compound when associated with RNA.
M = excitation of about 480-510 nm and emission of about 510-540 nm.

Example 37

Rifampicin-depletion of Bacterial RNA

Figure 3:
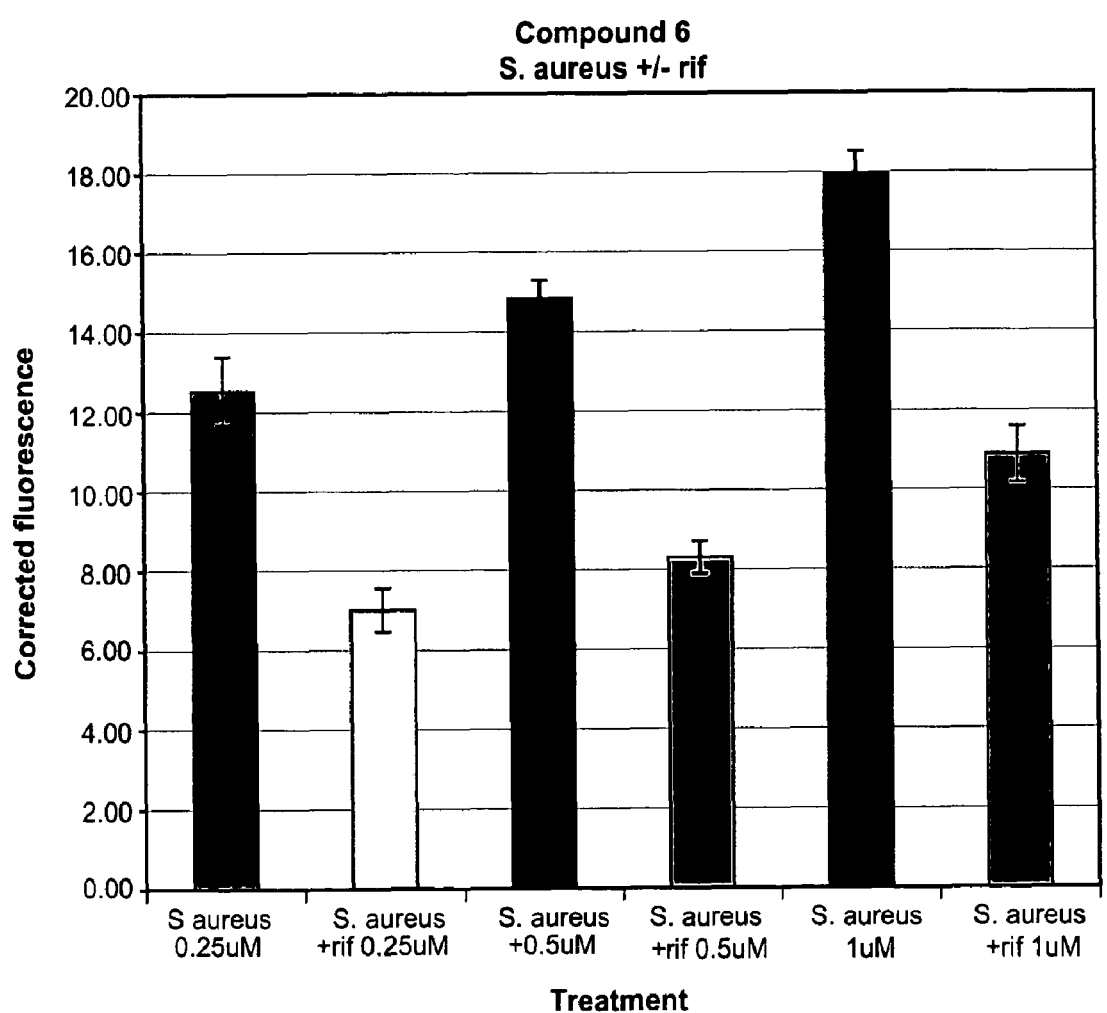
FIG. 3: Shows the difference in signal intensity from *S. aureus* cells treated with and without rifampicin when loaded with Compound 6 at three different concentrations (0.25, 0.5 and 1 µM). These results demonstrate that Compound 6 binds to both RNA and DNA, but demonstrates a stronger signal intensity when bound to RNA. Compound 6 could be preferentially binding to RNA or the compound may be fluorescing brighter on RNA but still have equal selectively for RNA and DNA. See, Example 37

Gram-positive (*Staphylococcus aureus*) and Gram-negative (*Eshcerichia coli*) bacteria in growth medium were treated with 25 µg/mL rifampicin for one hour. Treated and untreated bacteria were counted, diluted to $1 \times 10^7$ bacteria/mL in 0.85% NaCl, and 1 mL aliquots incubated with 0.25 µM, 0.5 µM, or 1 µM Compound 6 or Compound 9 for 10-15 minutes protected from light. The samples were analyzed by flow cytometry and then 100 µL volumes were transferred to a microplate in triplicate and analyzed by a microplate reader. The fluorescence intensity was corrected against the dye in solution, which was weakly fluorescent. Results demonstrate a decrease in fluorescent signal after removal of mRNA in comparison to untreated cells, See FIG. 3.

Example 38

Figure 4:
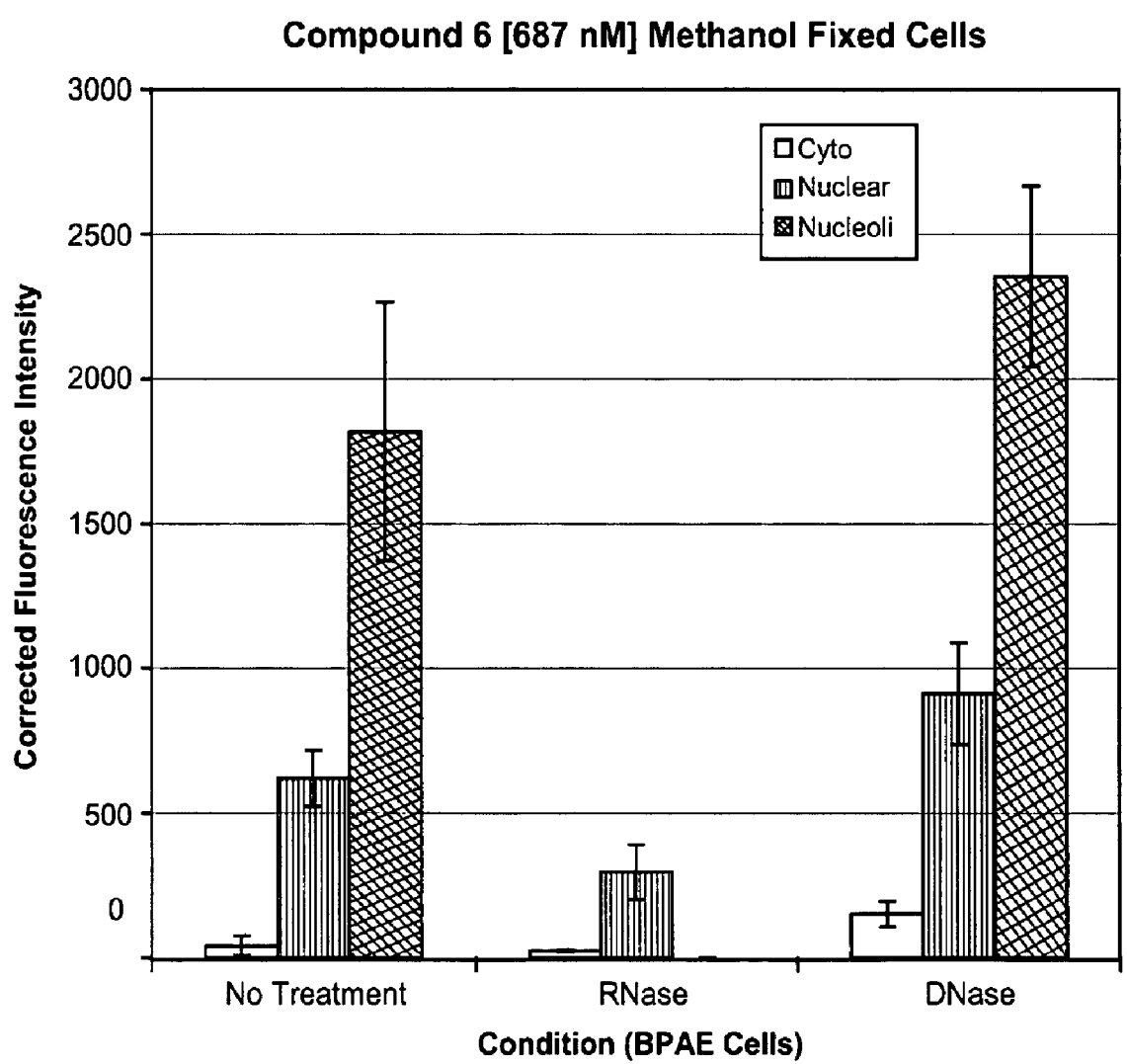
FIG. 4: Shows the binding of Compound 6 to DNA and RNA in methanol fixed cells in the cytoplasm, nucleus and nucleolus, that were untreated, RNase or DNase treated. RNase treated cells showed a significant reduction in signal intensity while DNase treated cells showed no decrease in signal intensity indicating that much of the signal seen in untreated cells is from Compound 6 fluorescing when bound to RNA. See, Example 38

Nucleic Acid Binding of Compound 6 after RNase and DNase on Methanol-Fixed Eukaryotic Cells Bovine pulmonary arterial endothelial cells were grown in media for one day after plating and then fixed ten minutes in 100% methanol at −20° C. Cells were washed 3×5 minutes in PBT (0.05M phosphate-buffered saline (PBS) containing 0.1% Triton X-100) and then treated with RNase (from Roche, at 1:500 dilution) or DNase (from Promega, at 1:100 dilution) for 2 hours at 37° C. Cells were washed again for 3×5 minutes in PBT and then labeled with Compound 6 at 687 nM concentration for 20 minutes. Cells were washed 3×10 minutes in PBS and mounted on microscope slides in Pro-Long antifade mounting medium. After the mountant had hardened, slides were examined on a Nikon Eclipse 800 upright fluorescent microscope and imaged with a FITC filter set, a Princeton Instrument MicroMax cooled CCD camera, and Universal Imaging MetaMorph imaging software. Both by eye and through intensity quantification, results showed that RNase washing eliminated Compound 6 labeling of nucleoli (where RNA is most strongly localized). DNase did not significantly affect nucleolar intensity. Nuclear labeling was significantly reduced by RNase, but not DNase. By eye, cytoplasmic label was reduced by RNase but not DNase. To test the activity of the DNase, a DAPI DNA label control was treated with RNase and showed a significant decline in label intensity. See, FIG. 4.

Example 39

Figure 5A:
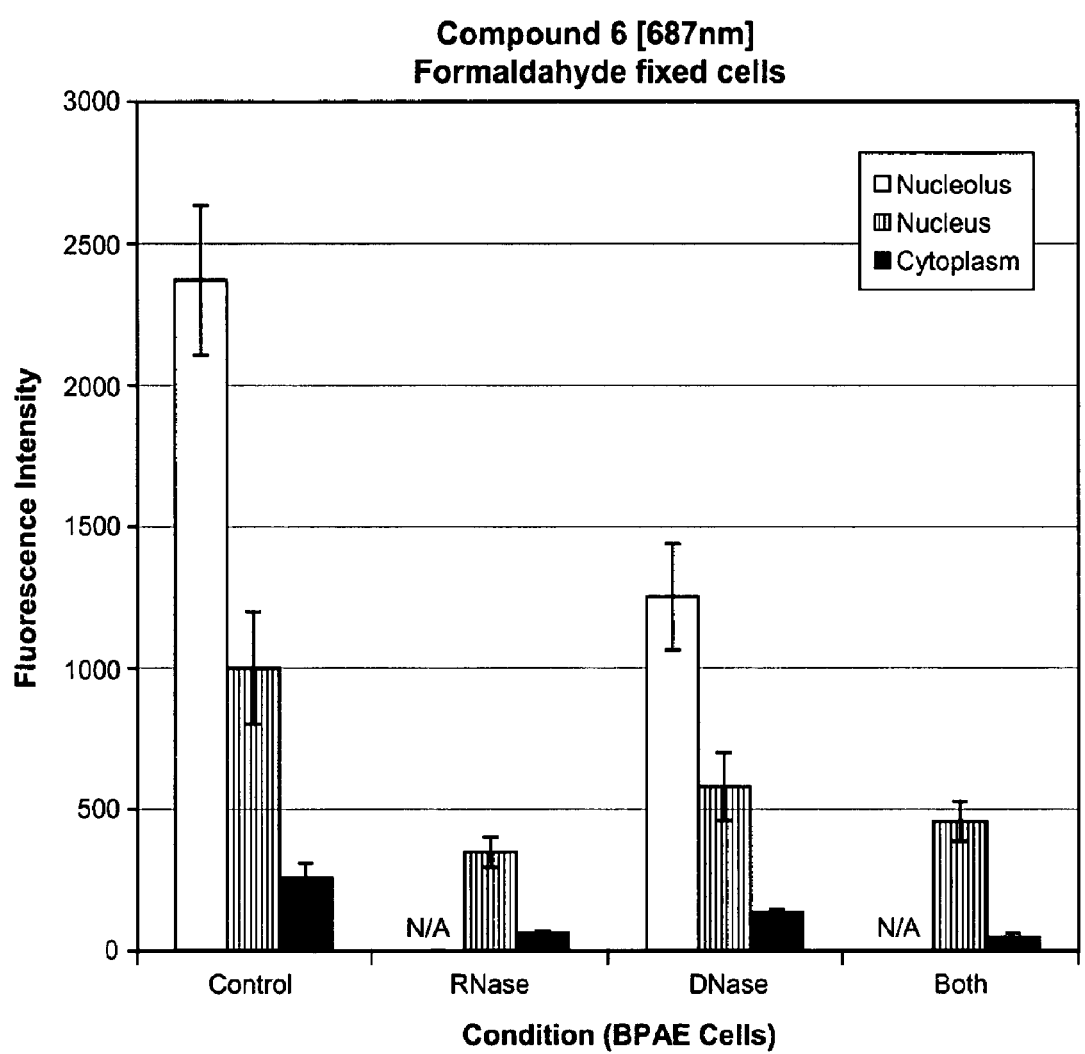
FIG. 5: Shows the binding of Compound 6 (5A) (10 μM) and Compound 19 (5B) (1 μM) in formaldehyde fixed cells in the cytoplasm, nucleus and nucleolus, that were untreated, RNase, DNase or RNase and DNase treated. These results show that RNase washing eliminated Compound 6 and Compound 19 labeling of the nucleolus (where RNA is most strongly localized) and that DNase significantly reduced the signal intensity from both compounds in this organelle. Both RNase and DNase significantly reduced nuclear labeling with Compound 6 whereas nuclear labeling with Compound 19 was significantly reduced with RNase, but not DNase. For Compound 6, both RNase and DNase significantly reduced cytoplasmic label, while for Compound 19, cytoplasmic label was not reduced at all with either RNase or DNase washing. See, Example 39
Figure 5B:
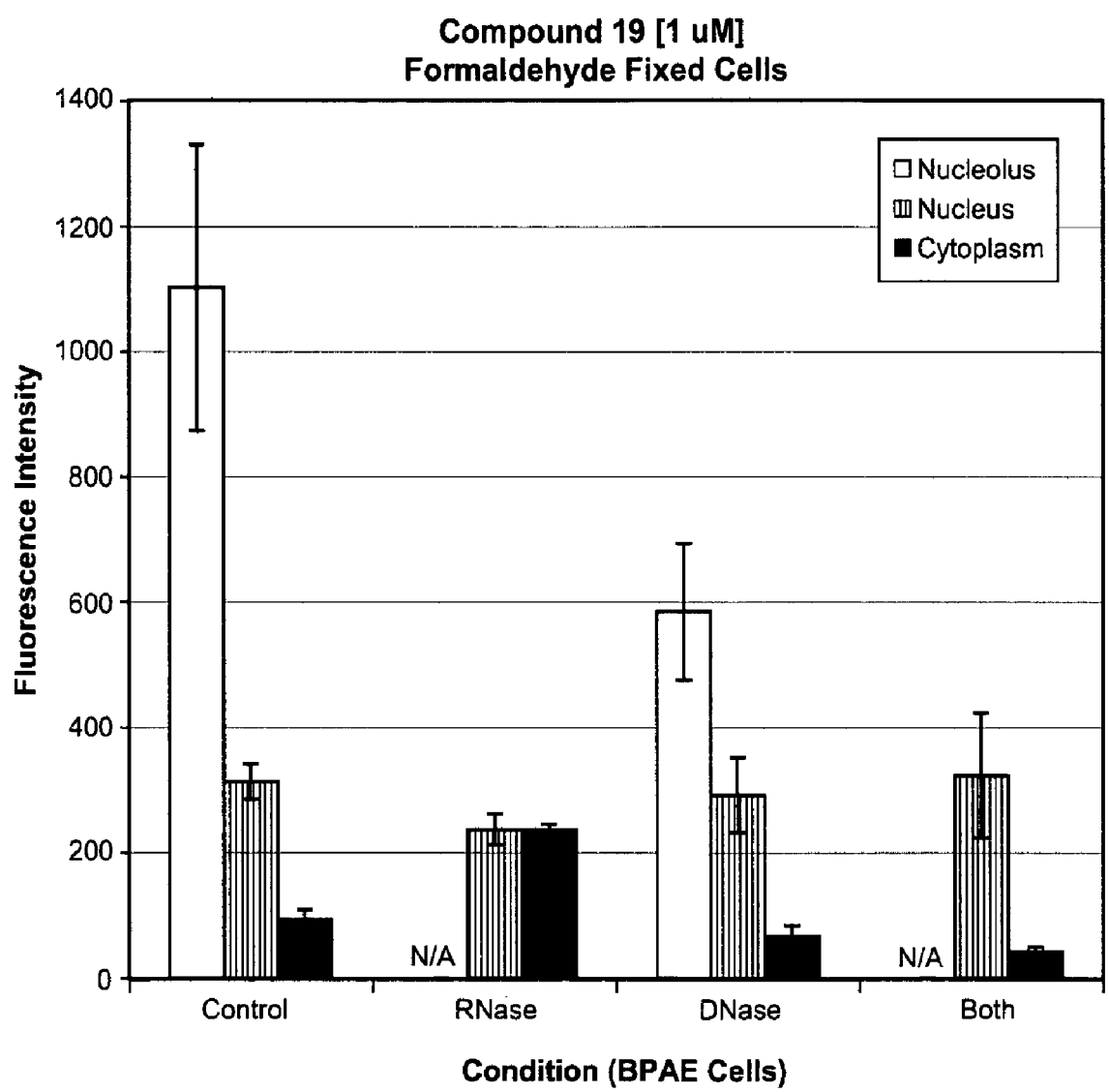

Nucleic Acid Binding of Compound 6 and Compound 19 on RNase and DNase treated Formaldehyde-Fixed Eukaryotic Cells Bovine pulmonary arterial endothelial cells were grown in media for one day after plating and then fixed fifteen minutes in 4% paraformaldehyde. Cells were washed 3×5 minutes in PBT (0.05M phosphate-buffered saline (PBS) containing 0.1% Triton X-100) and then treated with RNase (from Roche, at 1:500 dilution) or DNase (from Promega, at 1:100 dilution), or both for 2 hours at 37° C. Cells were washed again for 3×5 minutes in PBT and then labeled with Compound 6 at 687 nM concentration or Compound 19 at 1 µM concentration in PBS for 20 minutes. Cells were washed 3×10 minutes in PBS and mounted on microscope slides in ProLong antifade mounting medium (Molecular Probes, Inc.). After the mountant had hardened, slides were examined on a Nikon Eclipse 800 upright fluorescent microscope and imaged with a FITC filter set, a Princeton Instrument MicroMax cooled CCD camera, and Universal Imaging MetaMorph imaging software. Both by eye and through intensity quantification, results showed that RNase washing eliminated Compound 6 labeling of nucleoli (where RNA is most strongly localized). The same was true for Compound 19. DNase significantly reduced Compound 6 and Compound 19 nucleolar intensity. Nuclear labeling with Compound 6 was significantly reduced by both RNase and DNase. Nuclear labeling with Compound 19 was significantly reduced with RNase, but not DNase. For Compound 6, cytoplasmic label (which is more pronounced with paraformaldehyde-fixation than with methanol fixation) was significantly reduced by both RNase and DNase. With Compound 19, cytoplasmic label was not reduced at all with either RNase or DNase washing. See, FIG. 5.

Example 40

Nucleic Acid Binding of Compound 6 in Live Eukaryotic Cells Followed by Fixing of Cells Bovine pulmonary arterial endothelial cells were grown in media for one day after plating and then labeled before fixing with 687 nM Compound 6 for 20 minutes. Some cells were rinsed in media and separated for live imaging. The other cells were rinsed twice with media and then fixed in 4% paraformaldehyde for 15 minutes at room temperature, 0.5% glutaraldehyde for 5 minutes at room temperature, or 100% methanol for 10 minutes at −20° C. Cells were washed 3×10 minutes in phosphate-buffered saline and mounted on microscope slides in ProLong antifade mounting medium (Molecular Probes, Inc.). After the mountant had hardened, slides were examined on a Nikon Eclipse 800 upright fluorescent microscope and imaged with a FITC filter set, a Princeton Instrument MicroMax cooled CCD camera, and Universal Imaging MetaMorph imaging software. Live cells showed strong nucleolar label, strong punctate labeling in mitochondria consistent with mtDNA, and dimmer ubiquitous mitochondrial labeling. Fixation with either paraformaldehyde or glutaraldehyde removed all mitochondrial labeling. Nucleolar label remained, but nuclear label increased. General cytoplasmic labeling also increased significantly. Methanol-fixation had good nucleolar labeling, with only a slight increase in nuclear labeling. All mitochondrial labeling was removed. Cytoplasmic label increased slightly, but not nearly to the extent seen with other fixation. Results generally indicate that methanol-fixation is the recommended fixation technique.

Example 41

Nucleic Acid Binding of Compound 21 in Live Eukaryotic Cells

Bovine pulmonary arterial endothelial (BPEA) cells and HeLa human cervical cancer cells were grown in media for one day after plating on coverslips. Cells were labeled with 1 µM or 10 µM of Compound 21 for HeLa cells, or 10 µM in BPAE cells, in media at 37° C. for 20 minutes, then rinsed twice and mounted in warm medium. Coverslips were examined on a Nikon Eclipse 800 upright fluorescent microscope and imaged with a far red filter set, a Princeton Instruments MicroMax cooled CCD camera, and Universal Imaging MetaMorph imaging software. Compound 20 was cell permeable in live cells and in HeLa cells showed mitochondrial labeling, with stronger punctate spots within the mitochondria, typical of mitochondrial DNA staining. Also seen was very dim nucleolar labeling. The labeling in the cells was the same for the 1 µM or 10 µM concentration of Compound 20. In BPAE cells, there was no specific labeling evident, and much higher off-cell background. While Compound 20 demonstrated a fluorescence enhancement ratio (RNA/DNA) of 8.5 (See, Table 3), Compound 20 did not demonstrate selective detection of RNA in live cells.

Example 42

Figure 6:
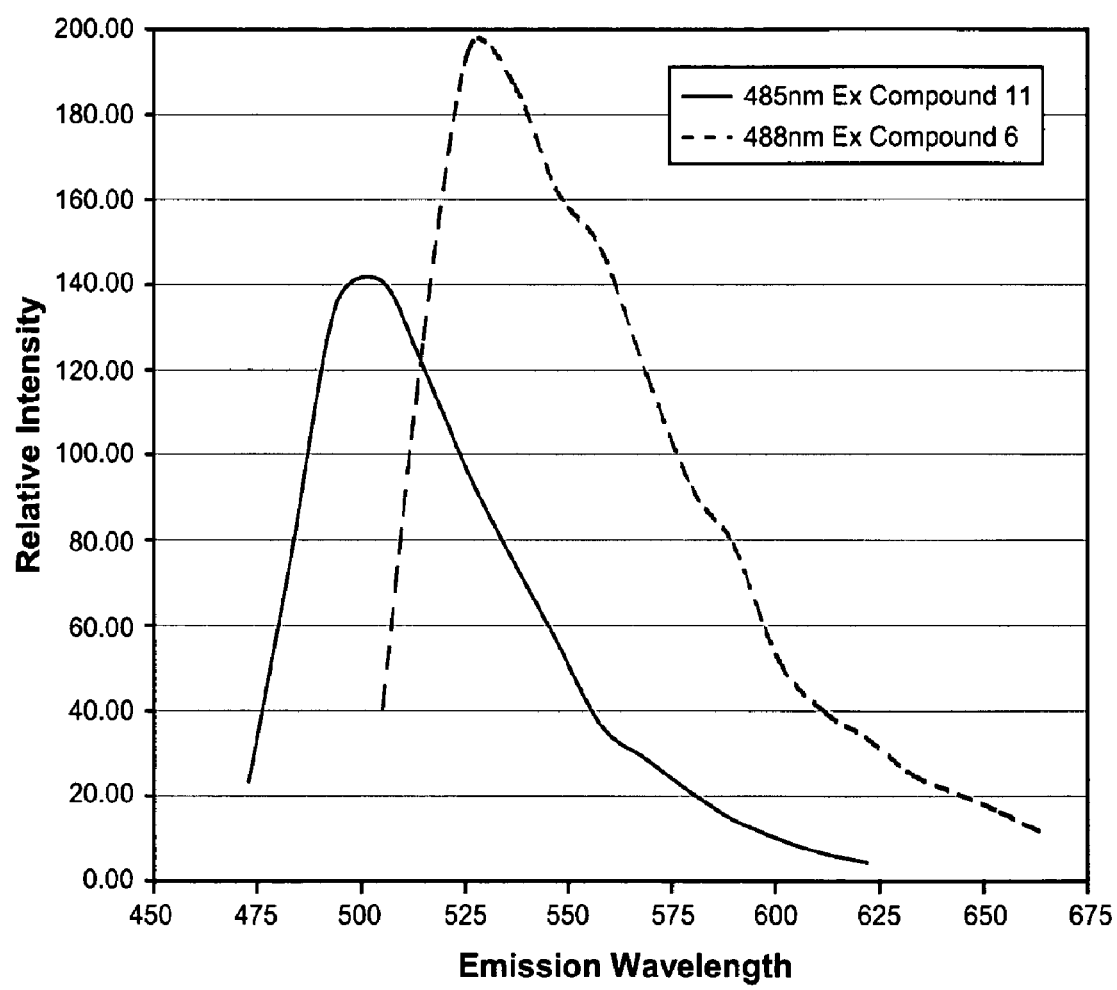
FIG. 6: Shows detection of intracellular nucleic acid with Compound 11 and Compound 6 with peak emission at a concentration of 500 nM for both compounds. See, Example 42

Nucleic Acid Binding of Compound 6 and Compound 11 Methanol-Fixed Eukaryotic Cells Bovine pulmonary arterial endothelial cells were grown in media for one day after plating on coverslips and then fixed 10 minutes in −20° C. 100% methanol. Cells were washed 3×5 minutes 50 mM phosphate buffered saline (PBS), pH 7.3. Cells were labeled with Compound 11 at 5 µM, 1 µM, or 500 nM concentration in PBS for 20 minutes, washed 3×10 minutes in PBS, and mounted in ProLong antifade mountant (Molecular Probes, Inc.). Cells were labeled with Compound 6 at 500 nM in PBS for 20 minutes. After the mountant had hardened, slides were examined on a Nikon Eclipse 800 upright fluorescent microscope and imaged with a blue-green filter set, a Princeton Instruments MicroMax cooled CCD camera, and Universal Imaging MetaMorph imaging software. Comparison of emission wavelength was made using a Zeiss 510 confocal microscope utilizing a META spectral unmixing system. The resultant staining pattern for both Compound 11 and Compound 6 showed strong nucleolar and cytoplasmic labeling, with dimmer nuclear labeling, indicating selective RNA staining. Optimal labeling for both compounds appeared to be about 500 µM. Spectral comparison of the emission wavelengths for Compound 11 showed a peak emission around 500 nm, while Compound 6 peaked around 530 nm. See, FIG. 6.

Example 43

Demonstration of Cell Permeability and Basic Nucleic Acid Label Pattern with a Concentration Series of Compound 1 in Live Cells Bovine pulmonary arterial endothelial cells were grown in media for one day after plating on coverslips, then labeled with 50 nM MitoTracker Red CMXRos (Molecular Probes, Inc., M7512) in Hank's balanced salt solution (HBSS) with HEPES for general mitochondrial labeling. After washing in HBSS, cells were then labeled with Compound 1 at various concentrations ranging from 100 nM up to 10 μM in media for 20 minutes at 370. Cells were washed well with HBSS. Coverslips were examined mounted in warm HBSS on a Nikon Eclipse 800 upright fluorescent microscope and imaged with a FITC filter set, a Princeton Instruments MicroMax cooled CCD camera, and Universal Imaging MetaMorph imaging software. At 100 nM to 500 nM, the resultant staining pattern showed what appeared to be mitochondrial DNA (mtDNA), with no nuclear label, or cytoplasmic background. The mtDNA signal was localized within mitochondria, as evidenced by MitoTracker Red labeling. When the concentration of Compound 1 was increased to 1 μM, nuclear labeling was seen as well as mtDNA. At 3 μM of Compound 1 or higher, mitochondrial morphology was disrupted, as evidenced with MitoTracker Red, and mtDNA labeling was lost, replaced with ubiquitous cytoplasmic labeling and strong nuclear labeling.

The preceding examples can be repeated with similar success by substituting the specifically described nucleic acid reporter molecules of the preceding examples with those generically and specifically described in the forgoing description. One skilled in the art can easily ascertain the essential characteristics of the present invention, and without departing from the scope thereof, can make various changes and modifications of the invention to adapt to various usages and conditions.

All publications, patents and patent applications mentioned in this specification are herein incorporated by reference to the same extent as if each individual publication, patent or patent application was specifically and individually indicated to be incorporated by reference.

What is claimed is:

1. A nucleic acid reporter molecule that has a RNA/DNA ratio of fluorescence enhancement greater than about one wherein the nucleic acid reporter molecule comprises a first monomethine unsymmetrical cyanine monomer moiety, a second monomethine unsymmetrical cyanine monomer moiety and a linker that is

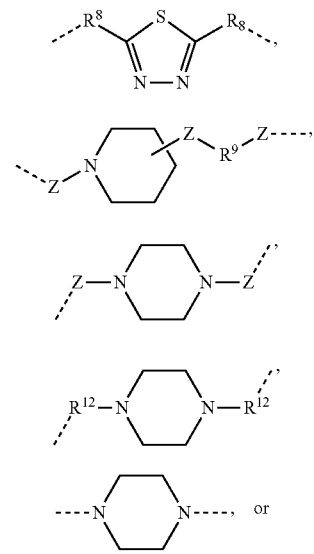

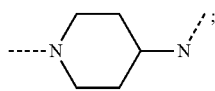

wherein $R^8$ is a substituted heteroatom or an unsubstituted heteroatom; $R^9$ is a substituted heteroatom or an unsubstituted heteroatom; $R^{12}$ is a substituted heteroatom or an unsubstituted heteroatom; each Z is —$(CH_2)_g$ wherein g is 0 or 1; and the first unsymmetrical cyanine monomer moiety is covalently attached to the linker; and the second unsymmetrical cyanine monomer moiety is covalently attached to the linker.

2. The reporter molecule according to claim 1, wherein
$R^8$ is —$NR^2$, —N= or S wherein $R^2$ is hydrogen, amine, substituted amine, substituted $C_1$-$C_6$ alkyl, unsubstituted $C_1$-$C_6$ alkyl, unsubstituted reactive group, substituted reactive group, unsubstituted carrier molecule, substituted carrier molecule, unsubstituted solid support, or substituted solid support;
$R^9$ is —$NR^2$, —N= or S wherein $R^2$ is hydrogen, amine, substituted amine, substituted $C_1$-$C_6$ alkyl, unsubstituted $C_1$-$C_6$ alkyl, unsubstituted reactive group, substituted reactive group, unsubstituted carrier molecule, substituted carrier molecule, unsubstituted solid support, or substituted solid support; and,
$R^{12}$ is —$NR^2$, —N= or S wherein $R^2$ is hydrogen, amine, substituted amine, substituted $C_1$-$C_6$ alkyl, unsubstituted $C_1$-$C_6$ alkyl, unsubstituted reactive group, substituted reactive group, unsubstituted carrier molecule, substituted carrier molecule, unsubstituted solid support, or substituted solid support.

3. The reporter molecule according to claim 1, wherein the monomethine unsymmetrical cyanine monomer moiety has the general formula:

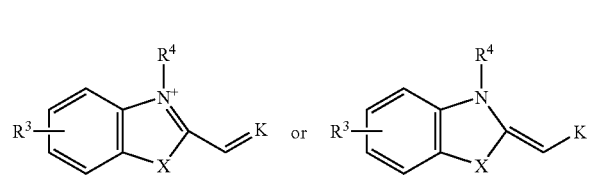

wherein $R^3$ is independently hydrogen, unsubstituted $C_1$-$C_6$ alkyl, substituted $C_1$-$C_6$ alkyl, unsubstituted $C_1$-$C_6$ alkoxy, substituted $C_1$-$C_6$ alkoxy, unsubstituted fused benzene, substituted fused benzene, unsubstituted trifluoromethyl, substituted trifluoromethyl, unsubstituted halogen, substituted halogen, unsubstituted reactive group, substituted reactive group, unsubstituted carrier molecule, substituted carrier molecule, unsubstituted solid support or substituted solid support;
$R^4$ is independently a unsubstituted $C_1$-$C_6$ alkyl, substituted $C_1$-$C_6$ alkyl, unsubstituted reactive group, substituted reactive group, unsubstituted carrier molecule, substituted carrier molecule, unsubstituted solid support or substituted solid support;
X is O, S, or $CR^6R^7$ wherein each $R^6$ and $R^7$ are independently a unsubstituted $C_1$-$C_6$ alkyl, substituted $C_1$-$C_6$ alkyl, unsubstituted reactive group, substituted reactive group, unsubstituted carrier molecule, substituted carrier molecule, unsubstituted solid support, substituted solid support or $R^6$ and $R^7$ taken together form a 5- or 6-membered saturated ring; and, K is substituted pyridinium, unsubstituted pyridinium, substituted quinolinium, or unsubstituted quinolinium wherein the first unsymmetrical cyanine monomer moiety is covalently attached to the linker at the K moiety; and the second unsymmetrical cyanine monomer moiety is covalently attached to the linker at the K moiety.

4. The reporter molecule according to claim 3, wherein the reactive group, solid support and carrier molecule comprise a linker that is a single covalent bond, or a covalent linkage that is linear or branched, cyclic or heterocyclic, saturated or unsaturated, having 1-20 nonhydrogen atoms selected from the group consisting of C, N, P, O and S; and are composed of any combination of ether, thioether, amine, ester, carboxamide, sulfonamide, hydrazide bonds and aromatic or heteroaromatic bonds.

5. The reporter molecule according to claim 4, wherein the reactive group is selected from the group consisting of an acrylamide, an activated ester of a carboxylic acid, a carboxylic ester, an acyl azide, an acyl nitrile, an aldehyde, an alkyl halide, an anhydride, an aniline, an amine, an aryl halide, an azide, an aziridine, a boronate, a diazoalkane, a haloacetamide, a haloalkyl, a halotriazine, a hydrazine, an imido ester, an isocyanate, an isothiocyanate, a maleimide, a phosphoramidite, a reactive platinum complex, a silyl halide, a sulfonyl halide, a thiol and a photoactivatable group.

6. The reporter molecule according to claim 5, wherein the reactive group is selected from the group consisting of carboxylic acid, succinimidyl ester of a carboxylic acid, hydrazide, amine and a maleimide.

7. The reporter molecule according to claim 4, wherein the carrier molecule is selected from the group consisting of an amino acid, a peptide, a protein, a polysaccharide, a nucleoside, a nucleotide, an oligonucleotide, a nucleic acid polymer, a hapten, a psoralen, a drug, a hormone, a lipid, a lipid assembly, a synthetic polymer, a polymeric microparticle, a biological cell or a virus.

8. The reporter molecule according to claim 7, wherein the carrier molecule is selected from the group consisting of an antibody or fragment thereof, an avidin or streptavidin, a biotin, a blood component protein, a dextran, an enzyme, an enzyme inhibitor, a hormone, an IgG binding protein, a fluorescent protein, a growth factor, a lectin, a lipopolysaccharide, a microorganism, a metal binding protein, a metal chelating moiety, a non-biological microparticle, a peptide toxin, a phosphotidylserine-binding protein, a structural protein, a small-molecule drug, or a tyramide.

9. The reporter molecule according to claim 4, wherein the solid support is selected from the group consisting of a microfluidic chip, a silicon chip, a microscope slide, a microplate well, silica gels, polymeric membranes, particles, derivatized plastic films, glass beads, cotton, plastic beads, alumina gels, polysaccharides, polyvinylchloride, polypropylene, polyethylene, nylon, latex bead, magnetic bead, paramagnetic bead, and superparamagnetic bead.

10. The reporter molecule according to claim 9, wherein the solid support is selected from the group consisting of Sepharose, poly(acrylate), polystyrene, poly(acrylamide), polyol, agarose, agar, cellulose, dextran, starch, FICOLL, heparin, glycogen, amylopectin, mannan, inulin, nitrocellulose, diazocellulose and starch.

11. The reporter molecule according to claim 3, wherein the linker is

12. The reporter molecule according to claim 11, wherein the reporter molecule is (Compound 6)

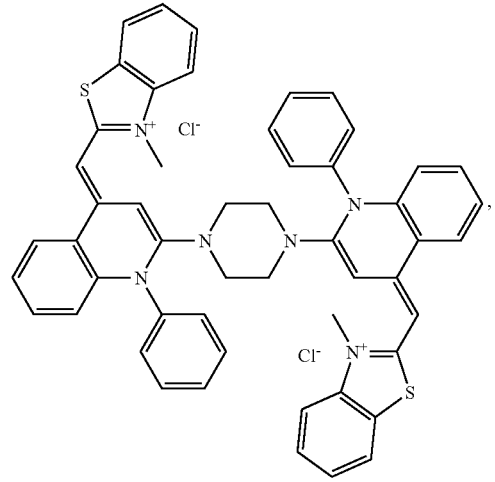

(Compound 11)

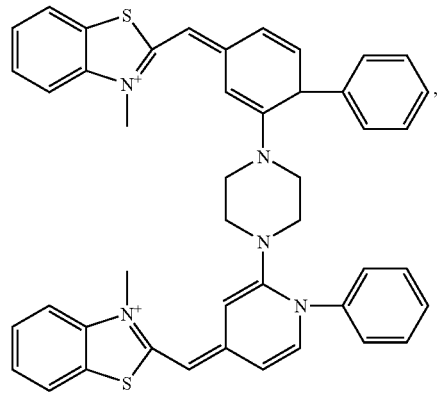

(Compound 13)

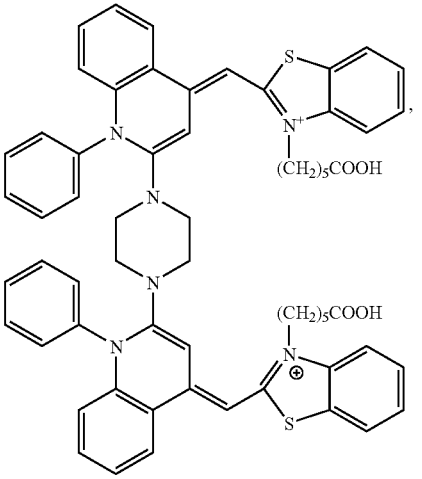

Compound 18
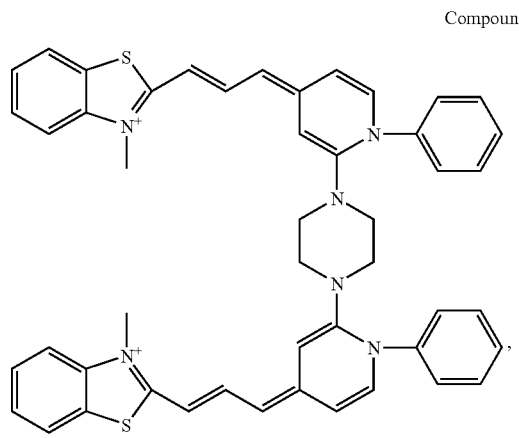
(Compound 19)
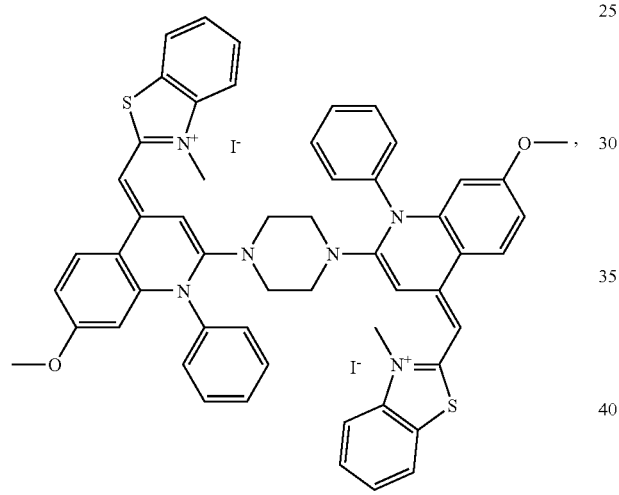
(Compound 20)
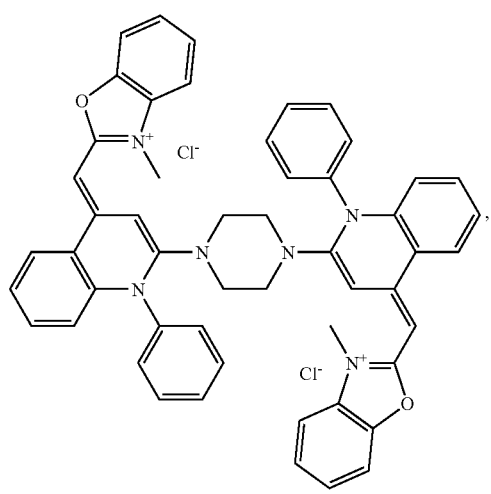
(Compound 23)
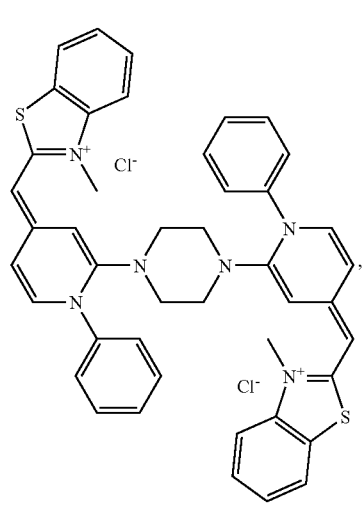
(Compound 32)
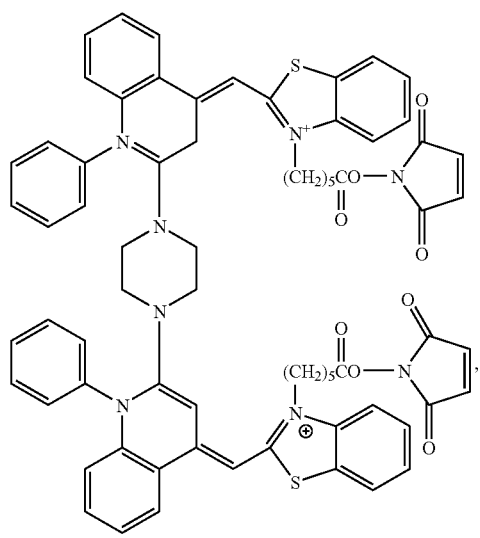
(Compound 33)
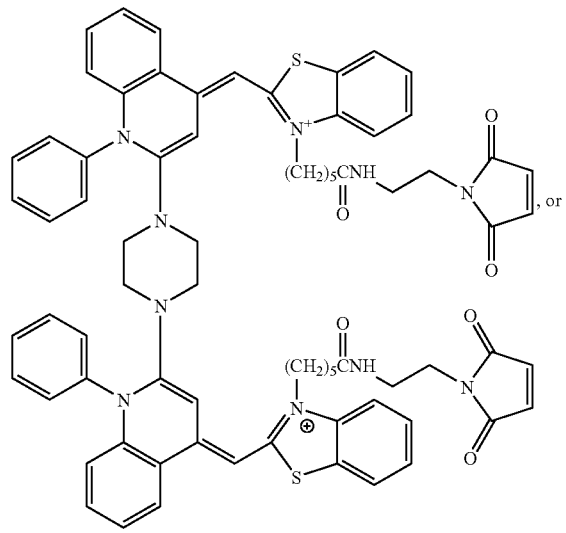

-continued (Compound 34)

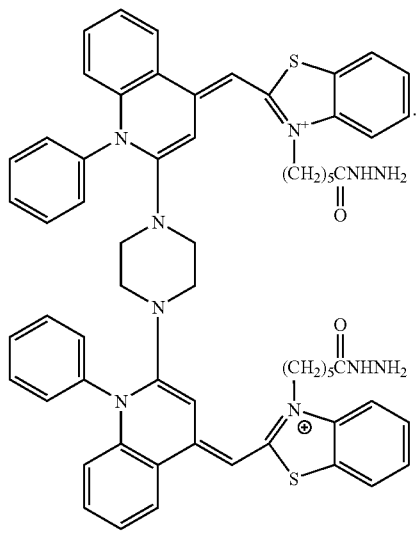

13. The reporter molecule according to claim 3, wherein $R^9$ is N or S and $R^{12}$ is N or S.

14. The reporter molecule according to claim 3, wherein the linker is

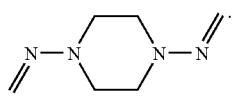

15. The reporter molecule according to claim 14, wherein the reporter molecule (Compound 9)

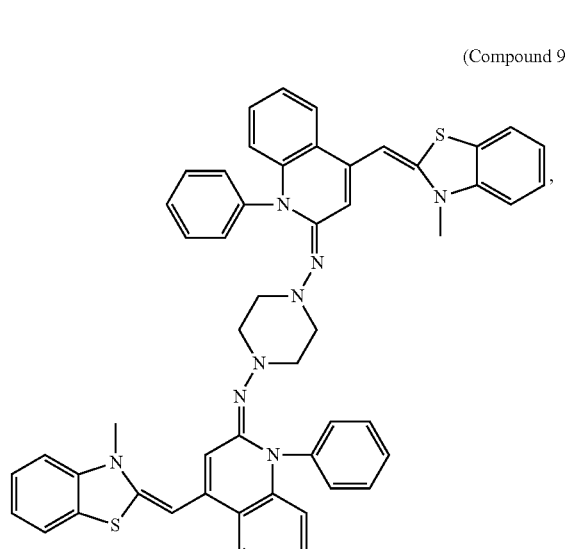

is or

-continued (Compound 25)

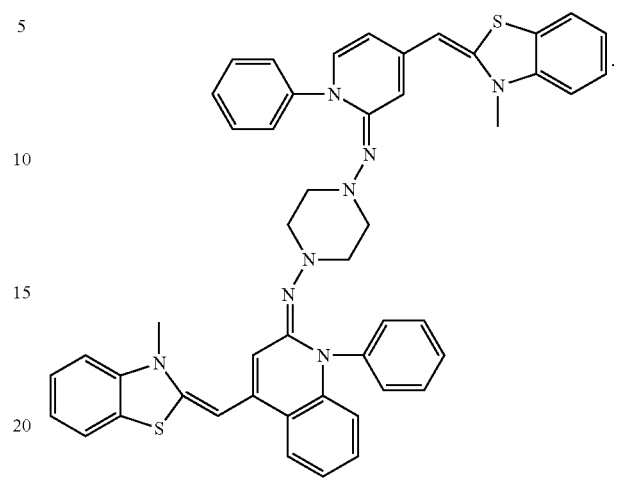

16. The reporter molecule according to claim 3, wherein the linker is

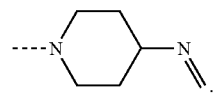

17. The reporter molecule according to claim 16, wherein said reporter molecule (Compound 21)

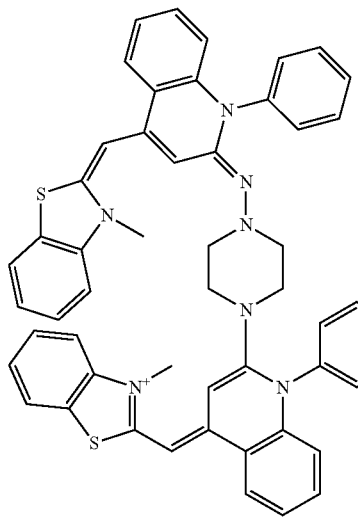

is or

-continued (Compound 30)

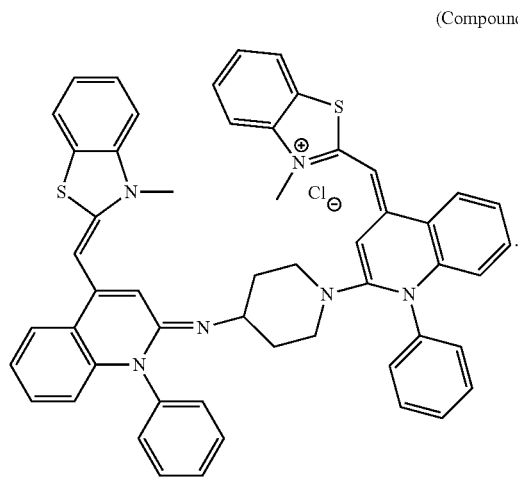

18. The reporter molecule according to claim 3, wherein the linker is

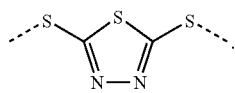

19. The reporter molecule according to claim 18, wherein the compound is (Compound 7)

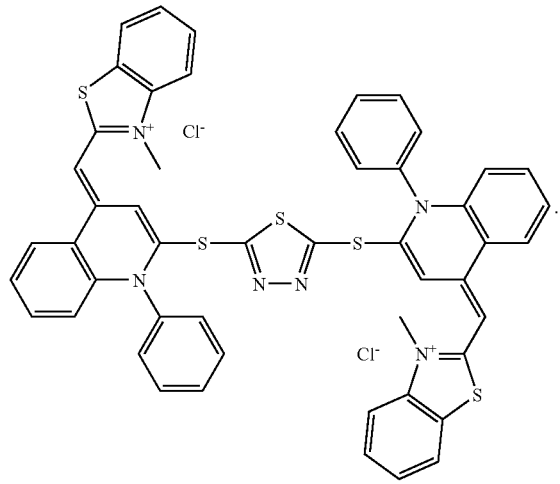

20. A nucleic acid reporter molecule that is

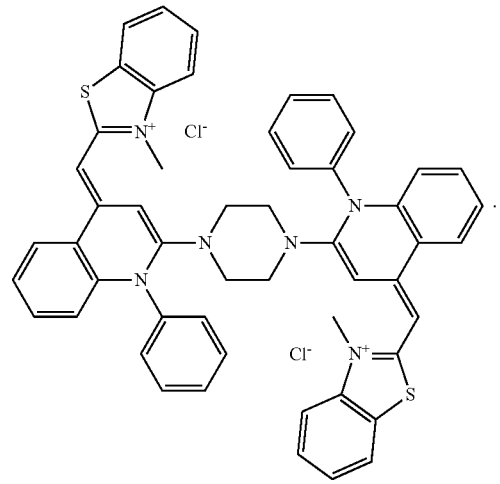

21. A kit for detecting nucleic acid in a sample, wherein the kit comprises: a nucleic acid reporter molecule comprising a first nucleic acid complexing monomer moiety, a second nucleic acid complexing monomer moiety and a linker that comprises at least one aromatic, heteroaromatic, cyclic or heterocyclic moiety comprising 3-20 non-hydrogen atoms selected from the group consisting of O, N, S, P and C, wherein the first nucleic acid complexing monomer moiety and the second nucleic acid complexing monomer moiety are covalently attached to the linker, and wherein the nucleic acid reporter molecule is

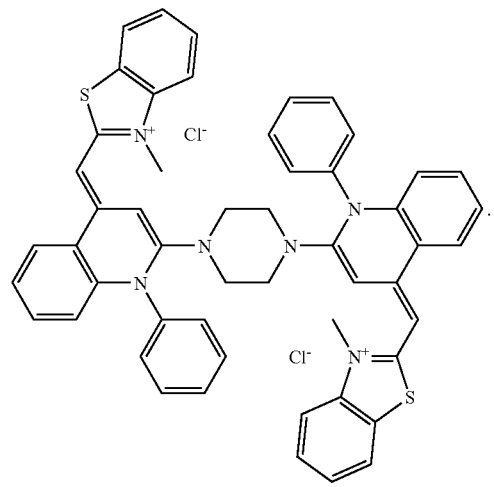

22. The kit according to claim 21, wherein the kit further comprises instructions for detecting the nucleic acid.

23. The kit according to claim 21, wherein the kit further comprises instruction for detecting intracellular RNA.

24. The kit according to claim 21, wherein the kit further comprises at least one component that is a sample preparation reagent, a buffer agent, an organic solvent or an addition nucleic acid reporter molecule.

25. A kit for detecting nucleic acid in a sample, wherein the kit comprises: a nucleic acid reporter molecule wherein the molecule is
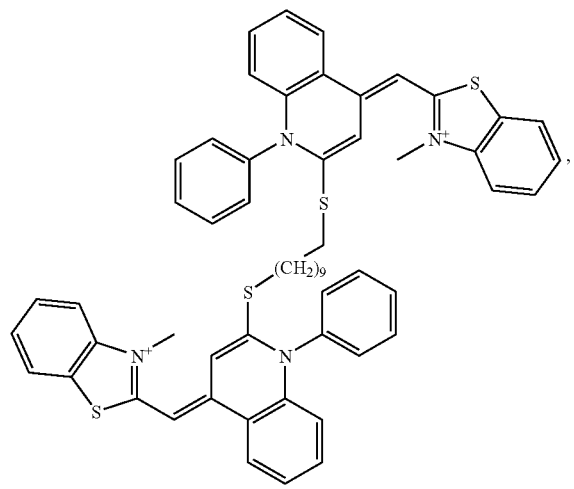
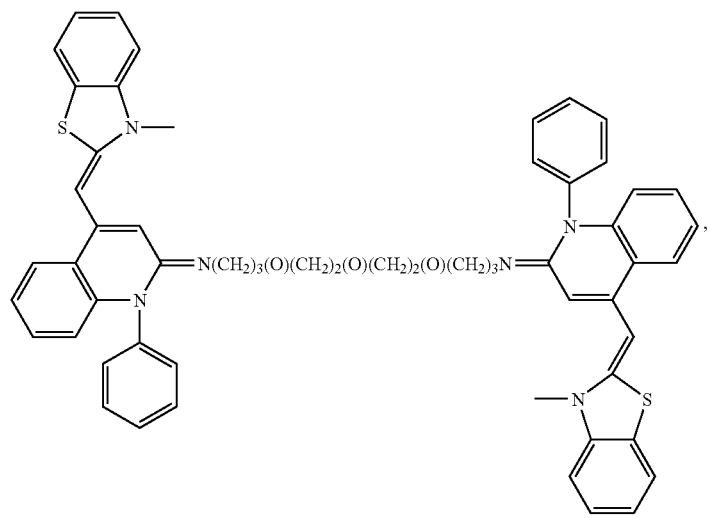
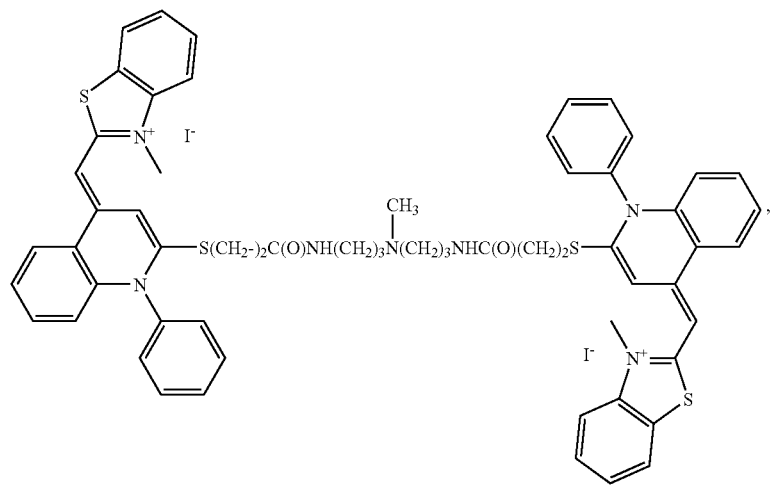

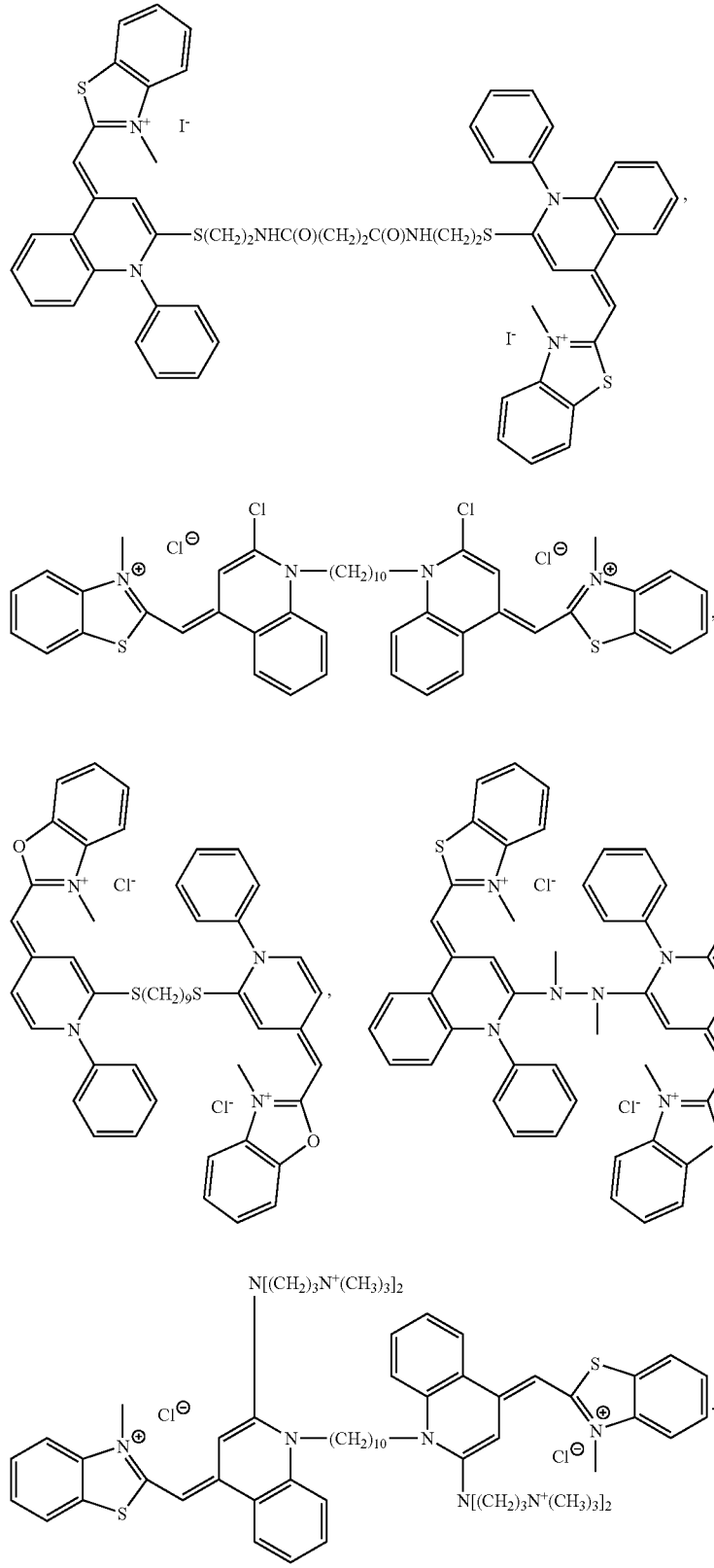
26. The kit according to claim 25, wherein the sample comprises biological fluids, buffer solutions, live cells, fixed cells, eukaryotic cells, prokaryotic cells, nucleic acid polymers, nucleotides, a polymeric gel or tissue sections.

27. The kit according to claim 26, wherein the nucleic acid is single stranded RNA, double stranded RNA, single stranded DNA or double stranded DNA.

28. A kit for detecting nucleic acid in a sample, wherein the kit comprises: a nucleic acid reporter molecule that is according to the formula

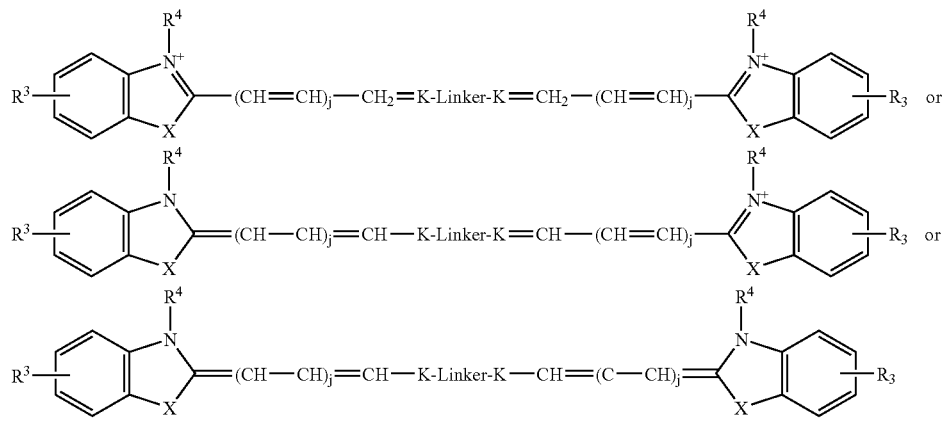

wherein each $R^3$ is independently hydrogen, unsubstituted $C_1$-$C_6$ alkyl, substituted $C_1$-$C_6$ alkyl, unsubstituted $C_1$-$C_6$ alkoxy, substituted $C_1$-$C_6$ alkoxy, unsubstituted fused benzene, substituted fused benzene, unsubstituted trifluoromethyl, substituted trifluoromethyl, unsubstituted halogen, substituted halogen, unsubstituted reactive group, substituted reactive group, unsubstituted carrier molecule, substituted carrier molecule, unsubstituted solid support or substituted solid support;

each $R^4$ is independently a unsubstituted $C_1$-$C_6$ alkyl substituted $C_1$-$C_6$ alkyl unsubstituted reactive group, substituted reactive group, unsubstituted carrier molecule, substituted carrier molecule, unsubstituted solid support or substituted solid support;

X is O, S or $CR^6R^7$ wherein each $R^6$ and $R^7$ are independently a unsubstituted $C_1$-$C_6$ alkyl, substituted $C_1$-$C_6$ alkyl unsubstituted reactive group substituted reactive group unsubstituted carrier molecule, substituted carrier molecule, unsubstituted solid support, substituted solid support or $R^6$ and $R^7$ taken together form a 5- or 6-membered saturated ring;

j is 0, 1, or 2;

linker is a series of stable covalent bonds comprising 1-30 nonhydrogen atoms selected from the group consisting of C, N, O, S and P; and, K is substituted pyridinium, unsubstituted pyridinium, substituted quinolinium, or unsubstituted quinolinium;

wherein the linker comprises at least one aromatic, heteroaromatic, cyclic or heterocyclic moiety comprising 3-20 nonhydrogen atoms selected from the group consisting of O, N, S, P and C.

29. The kit according to claim 28, wherein the linker has the formula (I) $-(Y)_r-(CH_2)_m-T_q-(CH_2)_n-E-(CH_2)_n-T_q-(CH_2)_m-(Y)_r-$;

wherein Y is a linear or branched moiety comprising 1-20 non-hydrogen atoms selected from the group consisting of C, N, O, P and S;

T is a unsubstituted heteroatom or a substituted heteroatom;

E is an aromatic, heteroaromatic, cyclic or heterocyclic moiety comprising 3-20 non-hydrogen atoms selected from the group consisting of O, N, S, P and C;

r is independently 0 or 1;

m is an integer of 0-6;

n is independently 0 or 1;

q is independently 0 or 1;

and wherein the first unsymmetrical cyanine monomer moiety is covalently attached to the linker; and the second unsymmetrical cyanine monomer moiety is covalently attached to the linker.

30. The kit according to claim 29, wherein E is

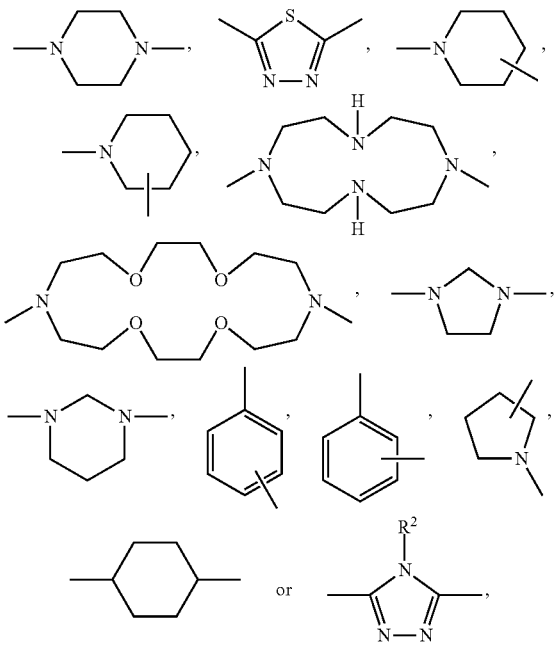

wherein $R^2$ is hydrogen, amine, substituted amine, substituted $C_1$-$C_6$ alkyl, unsubstituted $C_1$-$C_6$ alkyl, unsubstituted reactive group, substituted reactive group, unsubstituted carrier molecule, substituted carrier molecule, unsubstituted solid support, or substituted solid support.

31. The kit according to claim 29, wherein T, when present, is $-NR^2$, $-N=$ or S wherein the $R^2$ is hydrogen, amine, substituted amine, substituted $C_1$-$C_6$ alkyl, unsubstituted $C_1$-$C_6$ alkyl, unsubstituted reactive group, substituted reactive group, unsubstituted carrier molecule, substituted carrier molecule, unsubstituted solid support, or substituted solid support.

32. The kit according to claim 30, wherein the linker is

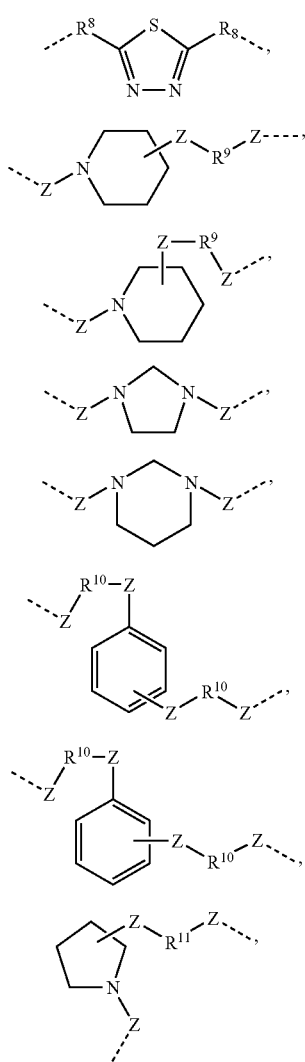

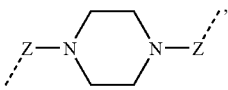

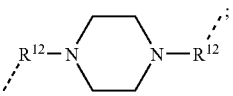

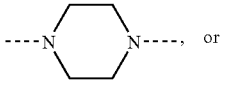

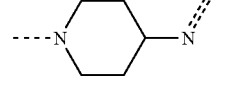

each $R^8$, $R^9$, $R^{10}$, $R^{11}$ and $R^{12}$ are independently a —$NR^2$, —N= or S wherein $R^2$ is hydrogen, amine, substituted amine, substituted $C_1$-$C_6$ alkyl, unsubstituted $C_1$-$C_6$ alkyl, unsubstituted reactive group, substituted reactive group, unsubstituted carrier molecule, substituted carrier molecule, unsubstituted solid support, or substituted solid support; each Z is independently —$(CH_2)_g$— wherein g is 0 or 1, wherein the dashed line is attached directly to the K moiety of the unsymmetrical cyanine monomer.

33. The kit according to claim 32, wherein $R^8$ is S.

34. The kit according to claim 32, wherein $R^{12}$ is —NH or —N=.

35. The kit according to claim 34, wherein the linker is

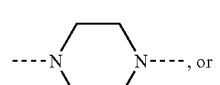

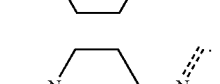

* * * * *